US012622809B2

(12) United States Patent
Herekar et al.

(10) Patent No.: US 12,622,809 B2
(45) Date of Patent: May 12, 2026

(54) SYSTEMS, METHODS, AND APPARATUS FOR PRESSURE-WAVE OCULAR THERAPY

(71) Applicant: SENOGEN GMBH, Rodgau (DE)

(72) Inventors: Rajeev Herekar, Palo Alto, CA (US);
Anjali Herekar, Palo Alto, CA (US);
Satish Herekar, Palo Alto, CA (US)

(73) Assignee: SENOGEN GMBH, Rodgau (DE)

( * ) Notice: Subject to any disclaimer, the term of this patent is extended or adjusted under 35 U.S.C. 154(b) by 723 days.

(21) Appl. No.: 17/633,899

(22) PCT Filed: Aug. 10, 2020

(86) PCT No.: PCT/US2020/045662
§ 371 (c)(1),
(2) Date: Feb. 8, 2022

(87) PCT Pub. No.: WO2021/026538
PCT Pub. Date: Feb. 11, 2021

(65) Prior Publication Data
US 2022/0287878 A1    Sep. 15, 2022

Related U.S. Application Data

(60) Provisional application No. 63/043,988, filed on Jun. 25, 2020, provisional application No. 62/979,097,
(Continued)

(51) Int. Cl.
*A61F 9/007* (2006.01)
*A61F 9/00* (2006.01)
(Continued)

(52) U.S. Cl.
CPC ........ *A61F 9/00781* (2013.01); *A61F 9/0017* (2013.01); *A61N 7/00* (2013.01);
(Continued)

(58) Field of Classification Search
None
See application file for complete search history.

(56) References Cited

U.S. PATENT DOCUMENTS 4,597,388 A    7/1986    Koziol et al.
5,301,659 A    4/1994    Brisson et al.
(Continued)

FOREIGN PATENT DOCUMENTS

CN    105377189 A    3/2016
CN    110198691 A    9/2019
(Continued)

OTHER PUBLICATIONS

"Vernier, Go Direct Platinum-Cell COnductivity Probe, 2024, Vernier Science Education" (Year: 2024).*
(Continued)

*Primary Examiner* — Michael T. Holtzclaw
(74) *Attorney, Agent, or Firm* — MARSHALL, GERSTEIN & BORUN LLP

(57) ABSTRACT

Apparatus, systems, and methods for treating an eye utilizing ab externo pressure wave generation. The shockwave generator comprises a housing comprising a fluid-filled chamber and an eye-contacting surface or chamber configured to contact a surface of the eye. First and second coaxially-aligned electrodes disposed within the housing are configured to generate an electric arc across a gap between the electrode tips when energized and thus produce a shockwave in a fluid of the fluid-filled chamber. The shockwave generator is coupled to the surface of the eye before focusing a shockwave to a pre-determined location on or below the surface of the eye. A plurality of shockwave generators may be disposed within a fluid-filled chamber of a contact lens, which may comprise a contact balloon.

13 Claims, 57 Drawing Sheets

Related U.S. Application Data filed on Feb. 20, 2020, provisional application No. 62/884,333, filed on Aug. 8, 2019.

(51) Int. Cl.
   *A61N 7/00* (2006.01)
   *A61F 9/008* (2006.01)

(52) U.S. Cl.
   CPC .............. *A61F 2009/00891* (2013.01); *A61F 2009/00895* (2013.01); *A61N 2007/0039* (2013.01); *A61N 2007/006* (2013.01); *A61N 2007/0086* (2013.01)

(56) References Cited

U.S. PATENT DOCUMENTS

| | | | | |
|---|---|---|---|---|
| 2007/0239082 A1* | 10/2007 | Schultheiss | ............ | A61B 46/17 601/4 |
| 2009/0281620 A1 | 11/2009 | Sacharoff et al. | | |
| 2011/0118728 A1 | 5/2011 | Heeren et al. | | |
| 2011/0144638 A1 | 6/2011 | Heeren et al. | | |
| 2013/0123779 A1* | 5/2013 | Auge, II | ................ | A61B 17/88 606/41 |
| 2014/0012276 A1 | 1/2014 | Alvarez | | |
| 2014/0243847 A1* | 8/2014 | Hakala | ................. | A61B 17/225 606/128 |
| 2014/0257144 A1 | 9/2014 | Capelli et al. | | |
| 2014/0364870 A1 | 12/2014 | Alvarez et al. | | |
| 2015/0051592 A1 | 2/2015 | Kintz | | |
| 2015/0224345 A1* | 8/2015 | Warlick | ................... | A61N 7/00 601/2 |
| 2016/0095752 A1* | 4/2016 | Srinivasan | .......... | A61F 9/00834 606/6 |
| 2016/0310766 A1 | 10/2016 | Cioanta | | |
| 2017/0087014 A1 | 3/2017 | Potter, Jr. et al. | | |
| 2017/0333132 A1* | 11/2017 | Grace | .................. | A61B 18/245 |
| 2018/0207029 A1 | 7/2018 | Herekar et al. | | |
| 2018/0287465 A1 | 10/2018 | Lin et al. | | |
| 2019/0040685 A1* | 2/2019 | Moeny | ................... | E21B 10/60 |

FOREIGN PATENT DOCUMENTS

| | | |
|---|---|---|
| DE | 4442931 A1 | 6/1996 |
| JP | H11169378 A | 6/1999 |
| WO | WO-2018134696 A1 | 7/2018 |

OTHER PUBLICATIONS

Search Report and Written Opinion, Singapore Application No. 11202201195W, dated Jun. 12, 2024.

International Search Report for Application No. PCT/US2020/045662, dated Nov. 6, 2020.

Communication pursuant to Article 94(3) EPC for European Application No. 20850917.4, dated May 10, 2024.

Office Action, Japanese Application No. 2022-508462, mailed Jul. 9, 2024, 14 pages.

Office Action, Indian Application No. 202217012440, mailed Apr. 17, 2025.

Office Action, Chinese Application No. 202080068195.7, mailed Apr. 17, 2025.

Office Action, Chinese application No. 202080068195.7, dated Dec. 19, 2025.

\* cited by examiner

100

108

109

102

106

110

112

116

116

114

104

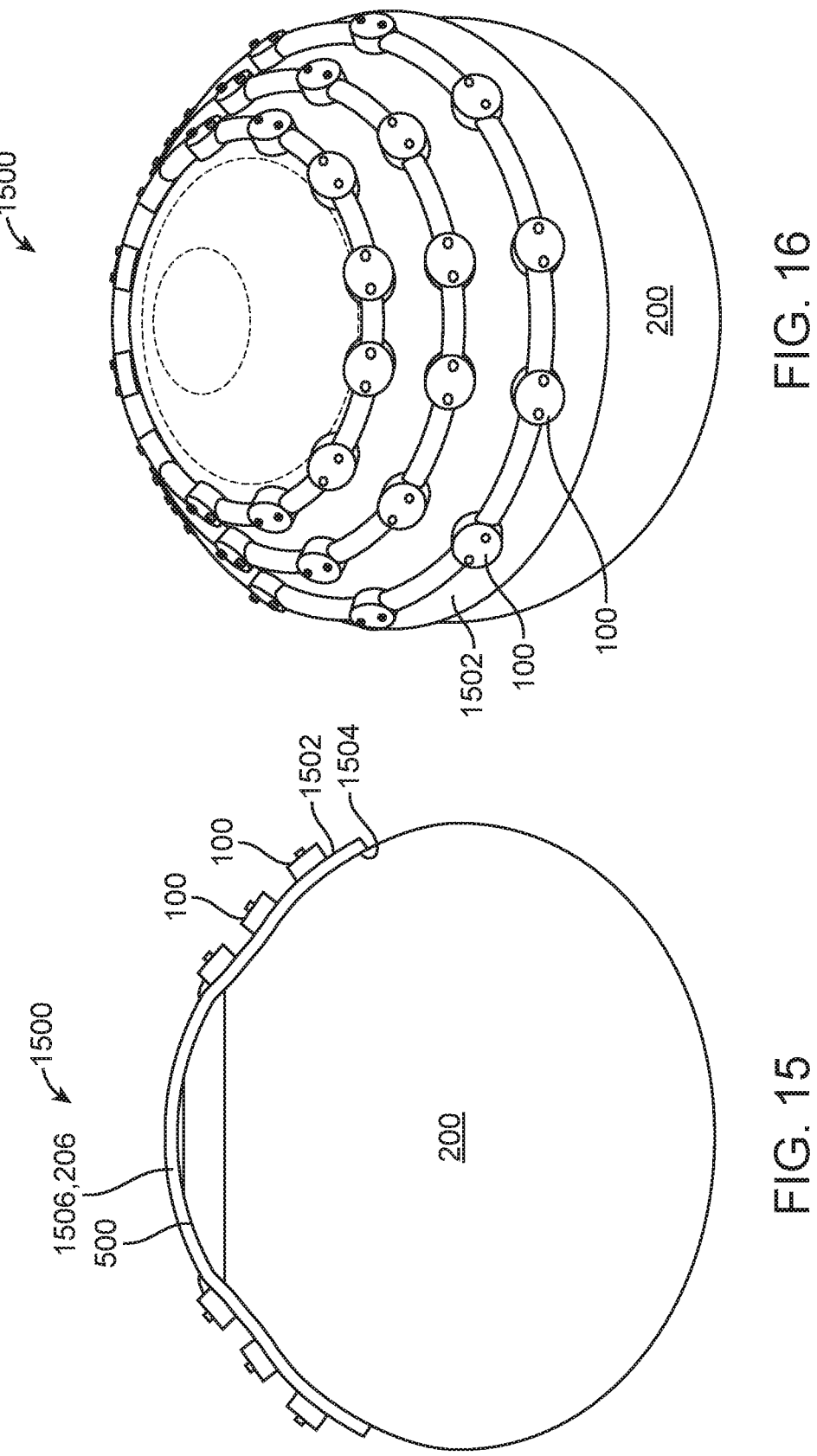

SYSTEMS, METHODS, AND APPARATUS FOR PRESSURE-WAVE OCULAR THERAPY

CROSS-REFERENCE

The subject matter of the present application is related to U.S. Provisional Patent Application No. 62/884,333, filed Aug. 8, 2019, entitled "Systems, Methods, and Apparatus for Pressure-Wave Ocular Therapy"; U.S. Provisional Patent Application No. 62/979,097, filed Feb. 20, 2020, entitled "Systems, Methods, and Apparatus for Pressure-Wave Ocular Therapy"; and U.S. Provisional Patent Application No. 63/043,988, filed Jun. 25, 20200, entitled "Systems, Methods, and Apparatus for Pressure-Wave Ocular Therapy"; the entire content of which is incorporated herein by reference.

BACKGROUND

Existing methods and apparatus for treating glaucoma, presbyopia, age-related macular degeneration (AMD), dry eye disease, and other ophthalmic conditions can produce less than ideal results.

For example, many prior approaches to treating glaucoma focus on reducing intraocular pressure (TOP) of the eye and can be more complex and/or invasive than would be ideal. Current glaucoma interventions include, for example, paralimbal delivery of drugs (such as prostaglandins), stents (such as minimally-invasive glaucoma surgery (MIGS) or canaloplasty), laser-based treatments (such as selective laser trabeculoplasty (SLT) or micropulse laser trabeculoplasty (MLT)), transscleral cyclophotocoagulation (TS-CPC), ultrasound CPC, trabeculoplasty, or trabeculectomies. Complications from such therapies can include hypotony, hyphema, hemorrhage, high TOP spike rate, decreased visual acuity, and cataract formation. For example, therapies such as trabeculectomy surgery or implantation of glaucoma drainage devices can require invasive surgical intervention and potentially have adverse safety risks in some instances. Other non-penetrating therapies often lose efficacy over time. Treatment to reduce TOP with medicated eye drops can be less than ideal due to lack of patient compliance, side effects in some instances, and variations between patients which can lead to variations in dosing and bioavailability of such medications. In light of the above, improved methods and apparatus of treating glaucoma are needed. Ideally, such methods and apparatus would be less invasive than some of the prior treatments and provide successful reduction in TOP.

Prior approaches for treating presbyopia focus on improving accommodative amplitude and/or replacing or repairing near acuity function in patients and can be more complex and/or invasive than would be ideal. Current presbyopia interventions include near acuity wearables (such as spectacles or contact lenses), lens or strut implants, drugs for miosis and lens-disaggregation, and incisional methods. Complications from such therapies can include complications of invasiveness, drug side effects, and the like in some instances. Additionally, such therapies often target only one possible source of reduced accommodation out of many, which may limit the overall efficacy of such therapies as singular treatment modalities. In light of the above, improved methods and apparatus of treating presbyopia are needed. Ideally, such methods and apparatus would be less invasive than some of the prior treatments and provide successful augmentation of accommodative amplitude.

Prior approaches for treating AMD focus on delaying onset of dry AMD and/or sealing leaking vasculature to limit degeneration in wet AMD and can be less effective than desired and/or incapable of reversing degeneration that has already occurred. Current interventions include nutritional interventions such as high antioxidant diets for dry AMD, laser photocoagulation for wet AMD, and intraocular anti-vascular endothelial growth factor (VEGF) therapies for wet AMD. Complications from such therapies can include continued degeneration of vision, a high rate of recurrence of leakage in wet AMD cases, scarring of the macula, eye infections, increased TOP, retinal detachment, and systemic vascular effects (e.g. hemorrhage, stroke, etc.) in some instances. Additionally, such therapies are rarely able to restore vision once it has been lost. In light of the above, improved methods and apparatus of treating AMD are needed. Ideally, such methods and apparatus would be less risky than some of the prior treatments and provide successful delay of degeneration and/or restoration of previously degenerated tissues.

Prior approaches for treating dry eye disease focus on improving, supplementing, and/or replacing natural tear formation and can be less effective than would be ideal. Current interventions include over-the-counter eyedrops (artificial tears), antibiotics, immune-suppressing eyedrops, corticosteroid eyedrops, eye inserts, scleral lenses, light therapy and eyelid massage, tear-stimulating eye drops, tear duct plugs, and tear duct thermal cautery. Complications from such therapies include continued dryness, increased irritation, sweating, corneal abrasion, and other drug side effects. Additionally, such therapies often require prolonged usage which can be less than ideal due to lack of patient compliance, side effects in some instances, and variations between patients which can lead to variations in dosing and bioavailability of eyedrop-dosed medications In light of the above, improved methods and apparatus of treating dry eye disease are needed. Ideally, such methods and apparatus would be more efficacious and provide more long-term improvements in eye lubrication for patients.

SUMMARY

It would therefore be desirable to provide improved methods and apparatus for treating glaucoma, presbyopia, age-related macular degeneration, dry eye disease, and other ophthalmic conditions. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure generally relates to medical devices, and methods and more particularly relates to methods and apparatus for treating the eye.

In a first aspect, an apparatus for treating an eye is provided. The apparatus comprises a housing comprising a fluid-filled chamber and an eye-contacting surface configured to contact a surface of an eye, a first electrode disposed within the housing, and a second electrode disposed within the housing and coaxially aligned with the first electrode, wherein a distal tip of the first electrode and a distal tip of the second electrode are separated by a gap. The first electrode and the second electrode are configured to generate an electric arc across the gap when energized and produce a shockwave in a fluid of the fluid-filled chamber.

In some embodiments, an inner surface of the housing may be configured to focus the shockwave to a predetermined location on or below the surface of the eye.

In some embodiments, the apparatus may further comprise a reflector disposed within the housing and configured to focus the shockwave to a predetermined location on or below the surface of the eye.

In some embodiments, the apparatus may further comprise a fluid inlet and a fluid outlet in fluid communication with the fluid-filled chamber.

In some embodiments, the apparatus may further comprise one or more wires coupled to the first electrode or second electrode and configured to provide energy thereto.

In some embodiments, the first electrode and the second electrode may comprise a first tip of a first wire and a second tip of a second wire.

In some embodiments, the fluid may comprise saline or water.

In some embodiments, the first and second electrodes may be coated with graphene to reduce erosion during use shockwave production.

In some embodiments, the housing may be ellipsoidal.

In some embodiments, the housing further may further a fluid-filled wave guide disposed between the fluid-filled chamber and the eye-contacting surface. The fluid-filled wave guide may be configured to fluidly couple the fluid-filled chamber and the eye-contacting surface.

In some embodiments, the apparatus may further comprise an acoustic lens disposed within the housing. The acoustic lens may be configured to focus the shockwave to one or more predetermined locations on or below the surface of the eye.

In some embodiments, the apparatus may further comprise a conductivity sensor at least partially disposed within the fluid-filled chamber. The conductivity sensor may be configured to measure a conductivity of the fluid within the fluid-filled chamber. In some embodiments, the conductivity sensor may comprise a pair of platinum electrodes.

In some embodiments, the apparatus may further comprise a light source at least partially disposed within the fluid-filled chamber and configured to emit light towards the surface of the eye. The light source may be configured to emit light having a wavelength sufficient to cross-link tissue.

In another aspect, a system for treating an eye is provided. The system comprises any of the shockwave-generating apparatuses described herein and an energy source. The energy source may be operably coupled to the first electrode and the second electrode of an electrode-based apparatus by one or more wires. The energy source may comprise a laser for an optical fiber-based apparatus.

In some embodiments, the first electrode may be coupled to a positive terminal of the energy source and the second electrode may be coupled to a negative terminal of the energy source.

In some embodiments, the energy source may comprise a high voltage pulse generator.

In some embodiments, the system may further comprise a current sensor coupled to the first electrode or the second electrode configured to determine a current level flowing to the first electrode or the second electrode.

In some embodiments, the system may further comprise a conductivity sensor fluidly coupled to the fluid outlet and configured to measure a conductivity of the fluid as it flows out of the fluid outlet.

In some embodiments, the system may further comprise a fluid recirculation system fluidly coupled to the fluid outlet and the fluid inlet and configured to recirculate fluid from the fluid-filled chamber and remove cavitation bubbles from the fluid.

In some embodiments, the system may further comprise a reservoir disposed on or under the eye-contacting surface. In some embodiments, the reservoir may comprise oxygen. Alternatively, or in combination, the reservoir may comprise riboflavin. Alternatively, or in combination, the reservoir may comprise a therapeutic agent or drug.

In another aspect, an apparatus for treating an eye is provided. The apparatus comprises a housing comprising a fluid-filled chamber and an eye-contacting surface configured to contact a surface of an eye, and an optical fiber disposed within the housing. The optical fiber is configured to generate shockwave in a fluid of the fluid-filled chamber when optical energy is emitted therefrom.

In some embodiments, an inner surface of the housing may be configured to focus the shockwave to a predetermined location on or below the surface of the eye.

In some embodiments, the apparatus may further comprise a reflector disposed within the housing and configured to focus the shockwave to a predetermined location on or below the surface of the eye.

In some embodiments, the apparatus may further comprise a fluid inlet and a fluid outlet in fluid communication with the fluid-filled chamber.

In some embodiments, the fluid may comprise saline or water.

In some embodiments, the fluid may comprise graphene in order to reduce light emission from the housing when the shockwave is generated.

In some embodiments, the housing may be ellipsoidal.

In some embodiments, the housing further may further a fluid-filled wave guide disposed between the fluid-filled chamber and the eye-contacting surface. The fluid-filled wave guide may be configured to fluidly couple the fluid-filled chamber and the eye-contacting surface.

In some embodiments, the apparatus may further comprise an acoustic lens disposed within the housing. The acoustic lens may be configured to focus the shockwave to one or more predetermined locations on or below the surface of the eye.

In another aspect, a system for treating an eye is provided. The system comprises a plurality of shockwave generators, and a contact lens disposed around the plurality of shockwave generators, the contact lens comprising a fluid-filled chamber and an eye-contacting surface configured to contact a surface of an eye.

In some embodiments, the contact lens may further comprise a suction mechanism configured to contact the surface of the eye and maintain contact between the surface of the eye and the eye-contacting surface.

In some embodiments, each of the plurality of shockwave generators may comprise an optical fiber.

In some embodiments, each of the plurality of shockwave generators may comprise a pair of coaxially-arranged electrodes and a reflector.

In some embodiments, the contact lens may comprise an inflatable outer housing comprising the eye-contacting surface.

In some embodiments, the contact lens may comprise an imaging port configured to receive an imaging apparatus.

In some embodiments, the plurality of shockwave generators may comprise a plurality of electrohydraulic, piezoelectric, laser, or magneto-electric shockwave generators.

In another aspect, a method for treating an eye is provided. The method comprises coupling an eye-contacting surface of a shockwave generator to a surface of an eye; generating a shockwave with the shockwave generator; and focusing the shockwave to a pre-determined location on or below the surface of the eye.

In some embodiments, the method may further comprise inducing microporation, cavitation, vasodilation, neovascularization, disaggregation, and upregulated growth factor production at the pre-determined location with the focused shockwave.

In some embodiments, the pre-determined location may comprise one or more of trabecular meshwork, Schlemm's canal, limbus, eyelid, meibomian gland, retina, and perifovea.

In some embodiments, the method may further comprise seeding microbubbles at the pre-determined location prior to generating the shockwave.

In some embodiments, the shockwave generator may comprise an optical fiber. Generating the shockwave may comprise emitting optical energy from the optical fiber into a fluid surrounding the optical fiber.

In some embodiments, the shockwave generator may comprise a first electrode and a second electrode. Generating the shockwave may comprise energizing the first and second electrodes to form an electrical arc across a gap between tips thereof.

In some embodiments, the method may further comprise coupling an eye-contacting surface of a second shockwave generator to the surface of the eye, generating a second shockwave with the second shockwave generator, and focusing the second shockwave to a second pre-determined location on or below the surface of the eye.

In some embodiments, the shockwave generator may be disposed within a fluid-filled chamber of a contact lens.

In some embodiments, the shockwave generator may be coupled to a trial frame.

In another aspect, a system for treating an eye is provided. The system comprises a shockwave generator configured to generate shockwave and a fluid-filled wave guide fluidly coupled to the shockwave generator and configured to direct the shockwave to an eye-contacting surface configured to contact a surface of an eye.

In some embodiments, the wave guide may comprise a stainless steel tube.

In some embodiments, the wave guide may have a length of about 12 mm or more.

In some embodiments, the wave guide may have a diameter within a range of about 1 mm to about 8 mm. For example, the wave guide may have a diameter of about 3 mm or about 8 mm.

In some embodiments, the system may further comprise a contact lens coupled to a distal end of the wave guide, the contact lens comprising a fluid-filled chamber and the eye-contacting surface.

In some embodiments, the shockwave generator and at least a portion of the wave guide may be coupled to a trial frame.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIG. 15 shows a side cross-sectional view of a plurality of shockwave generators coupled to an eye with a contact balloon, in accordance with embodiments;

FIG. 16 shows a perspective view of the system of FIG. 15 coupled to an eye, in accordance with embodiments;

DETAILED DESCRIPTION

Figure 1:
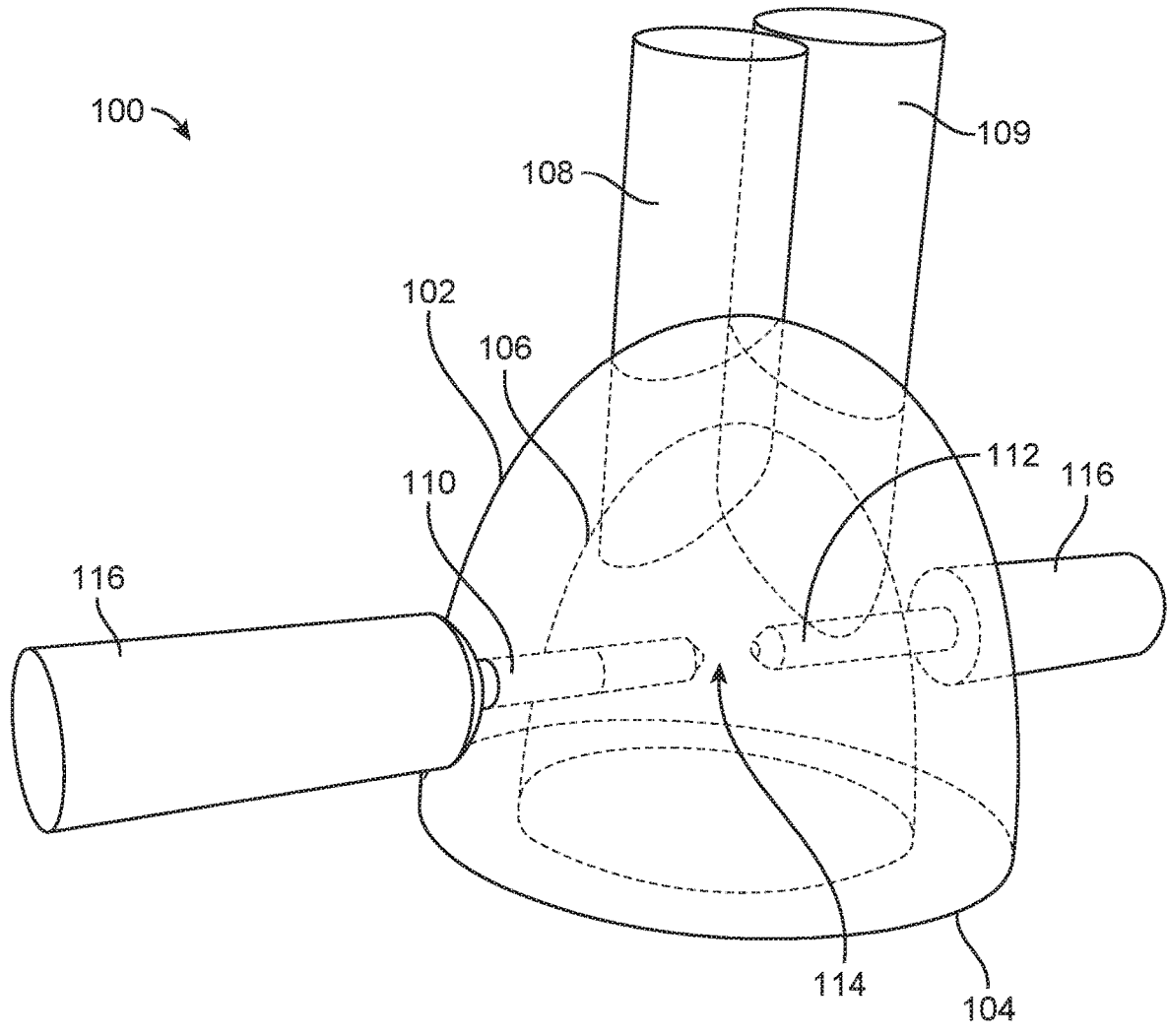
FIG. 1 shows a perspective view of a shockwave generator, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. It will be understood by one of ordinary skill in the art that the illustrations in the figures are not necessarily to scale and many elements may be enlarged or exaggerated for clarity and to facilitate understanding of the described embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The present disclosure is described in relation to deployment of systems, devices, or methods for treatment of an eye of a patient. However, one of skill in the art will appreciate that this is not intended to be limiting and the devices and methods disclosed herein may be used in other anatomical areas and in other surgical procedures.

The embodiments disclosed herein can be combined in one or more of many ways to provide improved methods and apparatus for treating the eye. The treated ocular tissue, membranes, or pathological transformations thereof, may comprise one or more of trabecular meshwork, sclera, vitreous, retina, meibomian gland ducts, zonules (e.g., posterior vitreous zonules (PVZ), etc.), ciliary body, lens, and diseased regions therein.

The embodiments as disclosed herein provide improved methods and apparatus for the treatment of one or more of presbyopia, glaucoma, AMD, dry eye disease, other ophthalmic conditions, or combinations thereof. For example, presbyopia treatments as disclosed herein can have a beneficial effect on a patient's intraocular pressure (hereinafter "iOP"). Alternatively, or in combination, the treatment can be directed to the treatment of glaucoma, for example. The treatments and apparatus disclosed herein can be combined with many known methods and apparatus for treatment. For example, the restoration of accommodation as described herein can be combined with one or more of many known prior accommodating intraocular lenses (IOLs), for example. Alternatively, or in combination, the methods and apparatus as disclosed herein can be combined with one or more known glaucoma therapies. Although many embodiments are described with reference to a natural lens of the eye, the embodiments disclosed herein can be used to improve vision with IOLs.

As used herein, the term "shockwave" refers to an acoustic wave having a high energy peak, a jump/step change in pressure, a fast rise time (e.g., on the order of 10 nsec), a high amplitude, and non-periodicity/short duration (e.g., about 10 μsec). A shockwave may also be referred to as a pressure wave. Shockwaves are distinct from ultrasound or high-intensity focused ultrasound waves in that they typically travel at significantly faster speeds with much higher intensities, and without the periodicity of an ultrasound wave. Shockwaves may be generated by electrohydraulic, piezo-electric, laser, or magneto-electric means, as will be understood by one of ordinary skill in the art based on the description herein.

Extracorporeal shockwave therapy (ESWT) is a non-invasive method for treatment of musculoskeletal disorders and is primarily used in the treatment of sports-related overuse tendinopathies. ESWT has also been employed in the treatment of non-union of long bone fracture, avascular necrosis of the femoral head, chronic diabetic and non-diabetic ulcers, and ischemic heart disease. The shockwaves used in ESWT has been shown to have mechanical and cellular effects on the treated tissues. For example, shock-wave treatment can have an analgesic effect on treated tissues. Shockwave treatment has also been shown to stimu-late production of growth factors, including eNOS, nNOS, and VEGF, which promote neovascularization and cellular regeneration. Shockwave treatment can also be used to generate free radicals, which can promote cell destruction when desired.

FIG. 1 shows a perspective view of a shockwave genera-tor 100. The shockwave generator 100 may comprise a first electrode 110 and a second electrode 112 disposed within housing 102. The housing 102 may comprise a fluid-filled chamber 106 and an eye-contacting surface 104. The eye-contacting surface 104 may be configured to be coupled to a surface of an eye of a patient. The first and second electrodes 110, 112 may be co-axially aligned with one another such that a gap 114 is formed between the distal tips of the electrodes 110.

The shockwave generator 100 may be configured to generate one or more shockwaves. The shockwave generator 100 may be configured to treat one or more tissues or structures on or below the surface of the eye with the shockwaves it generates. Treatment may be non-thermal. The shockwaves may be focused to a pre-determined loca-tion or unfocused as described herein. Shockwaves may be used to locally fractionate, microporate, dilate, and/or sen-solyse desired ocular tissues. In some embodiments, shock-waves may be used to produce biomechanical effects (such as vasodilation, microporation, softening, etc.) and/or or biochemical effects (such as neovascularlization, etc.) as described herein. In some embodiments, shockwaves may be used for drug delivery to ocular tissues.

For example, shockwave application to the eye may be used to (i) augment fluidic outflow of ischemic peri-limbal sclera and meibomian gland ducts via upregulation of VEGF and TGFβ2 (e.g., neovascularization) and/or eNOS and nNOS (e.g., vasodilation), (ii) induce stem cell differentia-tion (e.g., upregulation of $Ca^{2+}$), (iii) improve visual acuity and accommodative amplitude by fractionating viterous lacunae proximal to the pars plana, (iv) improve lenticular compliance by disagglomeration, and/or (v) deliver medi-caments (e.g., glaucoma, anti-VEGF, steroidal medications, etc. via sonoporation and/or sonophoresis). In some embodi-ments, shockwave therapy may reduce thermal tissue coagu-lations, perforations, lens or corneal translocations, cataract induction, and/or other undesirable aberrations which may be the results of other treatment methods and systems.

The eye-contacting surface 104 (also referred to herein as a tissue interface) may be shaped to correspond to a surface of an eye in order to create a seal when placed thereon. The eye-contacting surface 104 may comprise a pliable material configured to adapt its shape to the surface of an eye when placed thereon. The eye-contacting surface 104 may com-prise nylon, polyethylene terephthalate (PET), biaxially-oriented polyethylene terephthalate (BoPET), or the like.

The eye-contacting surface 104 may have a thickness within a range of about 12 μm to about 100 μm.

The eye-contacting surface 104 may have a diameter within a range of about 1 mm to about 8 mm, for example about 1 mm, about 2 mm, about 3 mm, about 5 mm, about 7 mm, or about 8 mm.

The eye-contacting surface 104 may comprise a suitable polymer such as polytetrafluoroethylene (PTFE), ethylene tetrafluoroethylene (ETFE), fluorinated ethylene propylene (FEP), polyoxymethylene (POM, e.g., DELRIN® available from DuPont), polyether block ester, polyurethane (e.g., Polyurethane 85A), polypropylene (PP), polyvinylchloride (PVC), polyether-ester (e.g., ARNITEL® available from DSM Engineering Plastics), ether or ester based copolymers (for example, butylene/poly(alkylene ether) phthalate and/or other polyester elastomers such as HYTREL® available from DuPont), polyamide (e.g., DURETHAN® available from Bayer or CRISTA D® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyeth-ylene, Marlex low-density polyethylene, linear low density polyethylene (e.g., REXELL®), polyester, polybutylene terephthalate PBT), polyethylene terephthalate (PET), poly-trimethylene terephthalate, polyethylene naphthalate (PEN), polyetheretherketone (PEEK), polyimide (PI), polyetherini-ide (PEI), polyphenylene sulfide (PPS), polyphenylene oxide (PPO), poly paraphenylene terephthalamide (e.g., KEVLAR®), polysulfone, nylon, nylon-2 (such as GRK.A-MID® available from EMS American Grilon), perfluoro (propyl vinyl ether) (PFA), ethylene vinyl alcohol, poly-olefin, polystyrene, epoxy, polyvinylidene chloride (PVdC), poly(styrene-A-isobutylene-A-styrene) (for example, SIBS and/or SIBS 50A), polycarbonates, ionomers, biocompatible polymers, other suitable materials, or mixtures, combina-tions, copolymers thereof, polymer/metal composites, and the like. In some embodiments, the eye-contacting surface 104 may comprise a mixture blended with a liquid crystal polymer (LCP) (e.g., up to about 6% LCP).

The fluid-filled chamber 106 may comprise a fluid dis-posed therein. The fluid may comprise a conductive (e.g., about 0.6 mS conductivity), biocompatible liquid. The fluid may comprise water or saline. The fluid may comprise a suspension of graphene in saline. The fluid may be chilled (e.g., about 10 degrees C.). In some embodiments, the shockwave generator 100 may further comprise a fluid inlet 108 and a fluid outlet 109 in fluid communication with the fluid-filled chamber 106. The fluid may be used to couple the shockwave generated in the gap 114 to the surface of the eye. The fluid may be circulated within the fluid-filled chamber 106 via the fluid inlet 108 and the fluid outlet 109. Fluid circulation may enable continuous extraction of metallic ions shed from the electrodes 110, 112 and cavitation bubbles generated during shockwave formation as pulsed delivery of the shockwaves is ongoing.

In some embodiments, the fluid flowing out of the fluid-filled chamber 106 via the fluid outlet 109 may be sampled periodically or continuously in order to determine the extent of electrode erosion. For example, saline conductivity may be sampled (e.g., as a proxy for measuring the gap 114 distance between the electrodes 110, 112 as the electrodes erode and metallic ions are released into the saline) and the voltage delivered to the electrodes 110, 112 may be adjusted to account for any changes in conductivity sensed.

The fluid-filled chamber 106 may be configured to act as a reflector in order to focus the shockwaves towards a desired pre-determined location. Alternatively, or in combi-nation, one or more reflectors may be coupled to an internal surface of the fluid-filled chamber 106 in order to focus the shockwaves. An inner wall of the fluid filled chamber 106 or a reflector coupled to an internal surface of the fluid-filled chamber 106 may be ellipsoidal in shape. Other exemplary shapes may blend between spherical and ellipsoidal, ellipsoidal with an offset stand-off, no reflector included with electrodes for radial wave transmission, coaxial wires with two insulation-exposed electrodes, ellipsoidal with flat-end reflectors for a non-symmetric shape, ellipsoidal-toroid, conical, S-shaped, contact lens with multiple reflectors and electrodes, meibomian ducts-coupled shapes, drug depots/reservoirs coupled to pressure wave generators, with suction ring features for stable intraoperative delivery, or the like as will be understood by one of ordinary skill in the art based on the disclosure herein.

The reflector may comprise sapphires, PMMA, graphene-coated polymers, a shockwave-reflecting polymer, stainless steel, aluminum, or the like. Some examples of suitable metals and metal alloys include stainless steel, such as 304V, 304L, and 316LV stainless steel; mild steel; nickel-titanium alloy such as linear elastic and/or super-elastic nitinol; other nickel alloys such as nickel-chromium molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In some embodiments, an aluminum dome structure positioned near a shockwave generator may be used to direct shockwave energy to a second focus with an ellipsoidal dome or into the tissue in a parallel direction with a parallel dome. The depth of focus of the dome structure may be within a range of about 3 mm to about 3 cm past the first focus shockwave generator.

It will be understood by one of ordinary skill in the art that the reflector (e.g., the shape of the fluid-filled chamber 106 and/or other reflectors coupled thereto) may be shaped to provide for a desired focus point, shape of the shockwave pattern, or the like.

The first and second electrodes 110, 112 may be operably coupled to a power source. In some embodiments, the first and second electrodes 110, 112 may be coupled to the power source by one or more wires 116. The one or more wires 116 may be insulated. In some embodiments, the first and second electrodes 110, 112 may comprise the distal ends of one or more wires 116. In some embodiments, the first and second electrodes 110, 112 may comprise pins coupled to the wires 116. In some embodiments, the first and second electrodes 110, 112 may comprise platinum, tungsten titanium, aluminum, titanium alloy (Ti-3Al), stainless steel, silver, gold, copper, nickel-chromium alloy, iron, brass, copper-Pt, copper, or combinations thereof, or the like.

In some embodiments, the first and/or second electrodes 110, 112 may be coated with graphene, gold, or another material in order to reduce erosion of the electrodes 110, 112 during use.

The first and second electrodes 110, 112 may have an outer diameter of about 0.5 mm. The first and second electrodes 110, 112 may have an outer diameter within a range of about 0.00785 mm to about 0.8118 mm. In some embodiments, the first and second electrodes 110, 112 may have an outer diameter within a range bounded by any two of the following values: about 0.005 mm, about 0.01 mm, about 0.015 mm, about 0.02 mm, about 0.025 mm, about 0.03 mm, about 0.035 mm, about 0.04 mm, about 0.045 mm, about 0.05 mm, about 0.055 mm, about 0.06 mm, about 0.07 mm, about 0.08 mm, about 0.09 mm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, and about 0.9 mm.

The first and second electrodes 110, 112 may have an outer diameter within a range of about 20 American Wire Gauge (AWG) to about 60 AWG. In some embodiments, the first and second electrodes 110, 112 may have an outer diameter within a range bounded by any two of the following values: about 20 AWG, about 25 AWG, about 30 AWG, about 35 AWG, about 40 AWG, about 45 AWG, about 50 AWG, about 55 AWG, and about 60 AWG.

In some embodiments, the first electrode 110 may be connected (e.g., via wire 116) to a positive terminal of a high voltage pulse generator and the second electrode 112 may be connected to a negative terminal of the high voltage pulse generator to generate a shockwave within the gap 114 between the two electrodes.

In some embodiments, the polarity of the first electrode 110 and the second electrode 112 may be reversible. Polarity reversal during therapy may help to extend the life of the first and second electrodes 110, 112, which may result in added repeatability of treatment across patients and devices.

The gap 114 between the first and second electrodes 110, 112 may be defined by the distance between the tips of the first and second electrodes 110, 112. In some embodiments, the distance between electrode tips may be within a range of about 0.05 mm to about 0.5 mm, for example within a range of about 0.1 mm to about 0.15 mm. For example, the distance may be about 0.05 mm, about 0.06 mm, about 0.07 mm, about 0.08 mm, about 0.09 mm, about 0.1 mm, about 0.11 mm, about 0.12 mm, about 0.13 mm, about 0.14 mm, or about 0.15 mm, about 0.16 mm, about 0.17 mm, about 0.18 mm, about 0.19 mm, about 0.2 mm, about 0.25 mm, about 0.3 mm, about 0.35 mm, about 0.4 mm, about 0.45 mm, or about 0.5 mm.

The gap 114 between the first and second electrodes 110, 112 may be sufficient to generate a shockwave using voltage pulses within a range of about 3 kilovolts (kV) to about 4 kV. These voltages may be stepped/combined and/or pre-pulsed and may be within a range of about 0-500V, 0-1000V, 0-1500V, 0-2000V, 0-2500V, 0-3000V, 0-3500V, or 0-4000V. The system may be configured to alternate between voltage polarities in order to extend electrode lifetimes.

The gap 114 between the first and second electrodes 110, 112 may be sufficient to generate a shockwave using a current of about 50 amperes.

The system may comprise one or more sensors. For example, a sensor may be coupled to one or more of the electrodes in order to determine the current flowing to the electrode(s). Alternatively, or in combination, a sensor may be provided to measure the conductivity of the saline flowing out of the fluid outlet as described herein. Temperature, sono-cavitational (i.e., bubble-making) efficiency, and/or fluid pressure sensors may be disposed within the shockwave-generating flow chamber (also referred to herein as a fluid-filled chamber) and may be used for intraoperative shockwave amplitude and focusing adjustment. The one or more sensors may be employed to provide for uniform, stable delivery of the shockwaves during treatment.

In some embodiments, the one or more sensors may be configured to do elastography measurements of various ocular tissues (e.g., the cornea, lens, and/or retina) based on the pressure waves generated by the shockwave generator(s) 100.

In some embodiments, the system may comprise one or more pressure sensors configured to provide pressure feedback for the shockwave generator(s) 100.

In some embodiments, the housing 102 may be molded or 3-D printed or the like.

In some embodiments, the shockwave generator 100 may be disposed on a distal end of a handheld probe.

Figure 2:
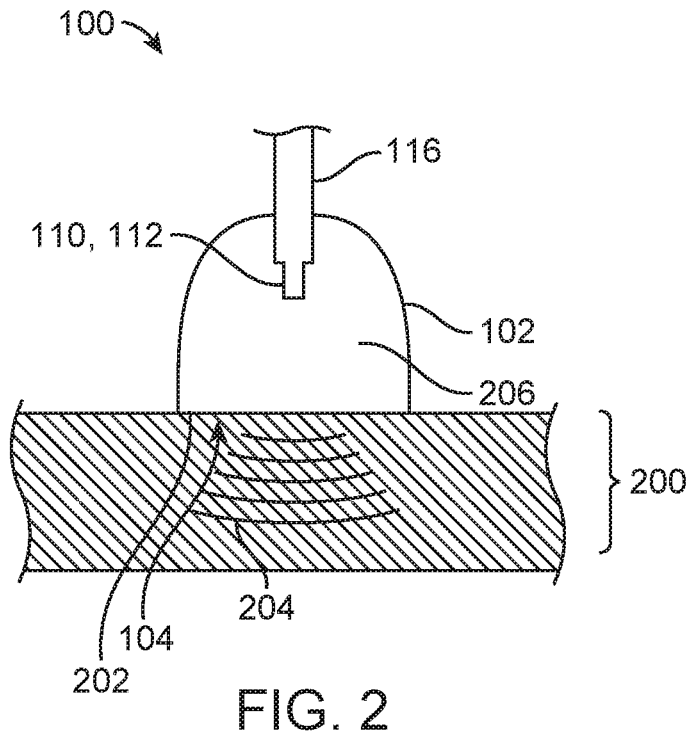
FIG. 2 shows a side view of an exemplary shockwave generator adjacent an eye, in accordance with embodiments.

FIG. 2 shows a side view of an exemplary shockwave generator 100 adjacent an eye 200. The shockwave generator 100 may be substantially similar the shockwave generator 100 shown in FIG. 1. The shockwave generator 100 may comprise a first electrode 110 and a second electrode 112 disposed within housing 102. The electrodes 110, 112 may, for example, comprise gold-coated pins coupled to one or more insulated wires 116 as described herein. The housing 102 may, for example, be ellipsoidal in order to facilitate focusing of the shockwave 204 in a desired direction and to a desired location on or below the surface of the eye. The housing 102 may comprise a fluid-filled chamber 106 and an eye-contacting surface 104 (also referred to herein as a tissue interface). The fluid-filled chamber 106 may, for example, be filled with a fluid such as saline 206. The eye-contacting surface 104 may be configured to be coupled to a surface of an eye of a patient. The first and second electrodes 110, 112 may be co-axially aligned with one another with a gap therebetween as described herein.

The shockwave generator 100 may be configured to focus a shockwave to a pre-determined location on or below the surface of the eye. The shockwave generator 100 may be configured to focus the shockwave in a trans-scleral, trans-limbal, trans-corneal manner to the pre-determined location within the tissue 200 of the eye. The pre-determined location may, for example, comprise one or more of the circumferential (i.e., 360 degrees) trabecular meshwork, Schlemm's canal, ciliary body (e.g., ciliary processes, muscle, selected parts anterior/posterior/equatorial of ciliary body, etc.), pars plana, pars plicata, cornea, sclera, lens, retina, fovea, peri-fovea, intermediate vitreous zonule (IVZ), posterior vitreous zonule (PVZ), vitreous, eyelids, and/or meibomian gland.

In some embodiments, the pre-determined location may be on the surface of the eye. In some embodiments, the pre-determined location may be at a tissue depth within a range of about sub-surface (e.g., 0.1 mm below the surface) to about 30 mm below the surface of the eye.

In some embodiments, the shockwaves may generate pressures within the eye at the pre-determined location up to about 100 MPa, for example within a range of about 0.1 MPa to about 100 MPa. In some embodiments, the shockwaves may generate pressures within the eye at the pre-determined location within a range of about 0.05 MPa to about 5 MPa.

In some embodiments, a coupling fluid or gel 202 may be on the eye-contacting surface 104 in order to facilitate contact between the eye-contacting surface 104 and the surface of the eye and/or in order to facilitate transmission of the shockwave from the shockwave generator to the eye. The coupling fluid or gel 202 may help to prevent energy misdirection due to unwanted reflections caused by air gaps between the shockwave generator 100 and the surface of the eye. In some embodiments, the coupling fluid or gel 202 may comprise one or more therapeutic substances.

In some embodiments, the shockwave generator 100 may be configured to delivery energy to the eye within a range of about 0.1 mJ/mm$^2$ to about 10 mJ/mm$^2$. For example, the shockwave generator 100 may be configured to deliver energy to the eye within a range bounded by any two of the following values: 0.1 mJ/mm$^2$, 0.2 mJ/mm$^2$, 0.3 mJ/mm$^2$, 0.4 mJ/mm$^2$, 0.5 mJ/mm$^2$, 0.6 mJ/mm$^2$, 0.7 mJ/mm$^2$, 0.8 mJ/mm$^2$, 0.9 mJ/mm$^2$, 1 mJ/mm$^2$, 1.5 mJ/mm$^2$, 2 mJ/mm$^2$, 2.5 mJ/mm$^2$, 3 mJ/mm$^2$, 3.5 mJ/mm$^2$, 4 mJ/mm$^2$, 4.5 mJ/mm$^2$, 5 mJ/mm$^2$, 5.5 mJ/mm$^2$, 6 mJ/mm$^2$, 6.5 mJ/mm$^2$, 7 mJ/mm$^2$, 7.5 mJ/mm$^2$, 8 mJ/mm$^2$, 8.5 mJ/mm$^2$, 9 mJ/mm$^2$, 9.5 mJ/mm$^2$, or 10 mJ/mm$^2$.

In some embodiments, the shockwave generator 100 may be configured to deliver shockwaves with an energy rise time within a range of about 10 nsec to about 100 μsec. In some embodiments, the shockwave generator 100 may be configured to deliver shockwaves with an energy rise time within a range bounded by any two of the following values: 10 nsec, 50 nsec, 100 nsec, 200 nsec, 300 nsec, 400 nsec, 500 nsec, 600 nsec, 700 nsec, 800 nsec, 900 nsec, 1 μsec, 10 μsec, 20 μsec, 30 μsec, 40 μsec, 50 μsec, 60 μsec, 70 μsec, 80 μsec, 90 μsec, or 100 μsec.

In some embodiments, the shockwave generator 100 may have a pulse duration within a range of about 10 nsec to about 10 μsec. In some embodiments, the shockwave generator 100 may have a pulse duration within a range bounded by any two of the following values: 10 nsec, 50 nsec, 100 nsec, 200 nsec, 300 nsec, 400 nsec, 500 nsec, 600 nsec, 700 nsec, 800 nsec, 900 nsec, 1 μsec, 10 μsec, 20 μsec, 30 μsec, 40 μsec, 50 μsec, 60 μsec, 70 μsec, 80 μsec, 90 μsec, or 100 μsec.

In some embodiments, the shockwave generator 100 may deliver shockwaves with a repetition rate within a range of about 1 Hz to about 50 KHz, for example within a range of about 1 Hz to about 1 KHz, for example within a range of about 1 to about 5 Hz. The shockwaves may be generated at a frequency of about 10 kHz. In some embodiments, the shockwave generator 100 may deliver shockwaves with a repetition rate within a range bounded by any two of the following values: 1 Hz, 5 Hz, 10 Hz, 50 Hz, 100 Hz, 200 Hz, 300 Hz, 400 Hz, 500 Hz, 600 Hz, 700 Hz, 800 Hz, 900 Hz, 1 kHz, 10 kHz, 20 kHz, 30 kHz, 40 kHz, or 50 kHz.

In some embodiments, the number of shockwaves delivered by the shockwave generator 100 may be within a range of about 1 to about 10,000 shockwaves. It will be understood by one of ordinary skill in the art the number of shockwaves delivered may depend on the desired tissue transformation result of the treatment.

In some embodiments, the total time for treatment of the target tissue at the pre-determined location may be within a range of about 30 seconds to about 30 minutes, for example within a range of about 2 to about 5 minutes. In some embodiments, the total time for treatment of the target tissue at the pre-determined location may be within a range bounded by any two of the following values: 30 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes.

In some embodiments, the RF frequencies of the electrodes 110, 112 may be within a range of about 3-30 Hz and from 300 GHz to 3 THz. Lower power pre-pulsing may be incorporated for tissue seeding.

The shockwaves may be focused or unfocused. In some instances, focused shockwaves may be preferred for delivery of larger amounts of energy to the target tissue in order to produce biomechanical effects in the tissue. In some instances, unfocused shockwaves may be preferred for delivery of lower levels of energy to the target tissue in order to provide gentle biochemical stimulation of the tissue.

In some embodiments, the shockwaves may be focused to a pre-determined location on or below the surface of an eye. Propagation of the focused wave may be non-linear and steepening may occur. The shockwaves may have a rise time of about 0.01 µsec, a compression of about 0.3 µsec, a positive peak pressure within a range of about 0 to about 100 MPa, and an energy flux density at the pre-determined location of about 0 to about 3 mJ/mm².

In some embodiments, the shockwaves may be delivered to the pre-determined location on or below the surface of an eye without focusing. The unfocused waves may be divergent, convergent, or planar waves. Propagation of the unfocused wave may be linear and steepening may not occur. The shockwaves may have a rise time of about 50 nsec, a compression of about 200 nsec to about 10 µsec, a positive peak pressure within a range of about 0 to about 10 MPa, and an energy flux density at the pre-determined location of about 0 to about 0.3 mJ/mm².

Figure 3:
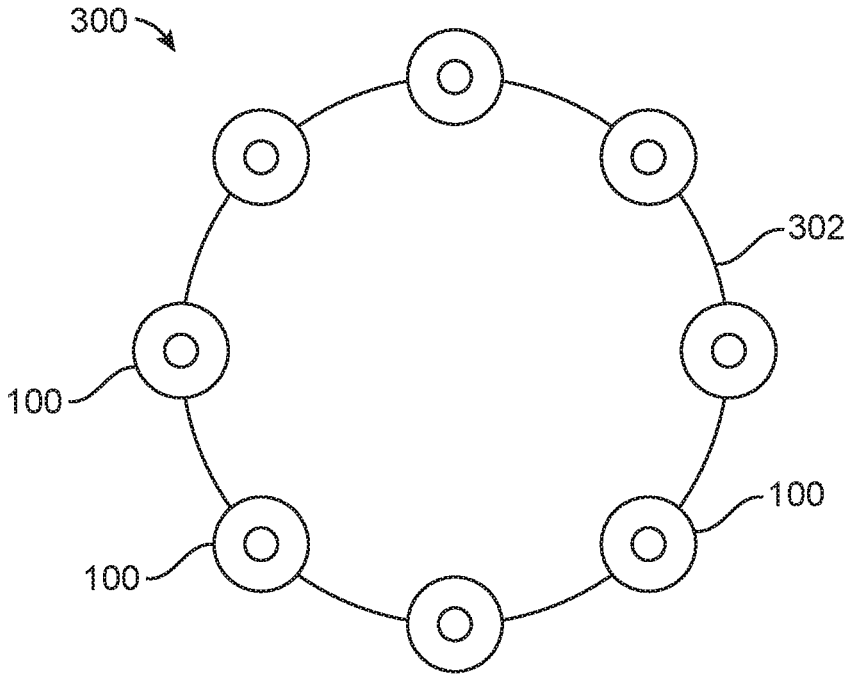
FIG. 3 shows a top view of an array of shockwave generators, in accordance with embodiments.

FIG. 3 shows a top view of an array 300 of shockwave generators 100. In some embodiments, the array 300 may comprise eight shockwave generators 100 disposed at equal distances in an annulus around the limbus 302 at a diameter of about 10 to about 15 mm for limbus-guided glaucoma treatment. Limbus-guided glaucoma treatment may be focused towards the trabecular meshwork and/or Schlemm's canal as described herein. Focusing the shockwaves to multiple locations along the trabecular meshwork and/or Schlemm's canal may result in dilation of the treated tissue and improved fluid outflow, which may reduce IOP in glaucomatous eyes.

An array of shockwave generators may comprise two or more shockwave generators 100. For example, an array may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 37, 38, 40, 41, 42, 43, 44, 45, 46, 47, 48, 49, 50, or more shockwave generators. The array of shockwave generators may comprise any number of shockwave generators desired.

The shockwave generators 100 may be connected in parallel or in series.

The shockwave generators 100 may be configured to be energized independently of or simultaneously with one another. In some embodiments, all of the shockwave generators 100 may be fired at the same time. In some embodiments, none of the shockwave generators may be fired at the same time. In some embodiments, at least two shockwave generators 100 may be fired simultaneously. In some embodiments, the shockwave generators may be independently-controlled.

In some embodiments, the shockwave generators 100 may be configured to be energized circumferentially in sequence. In at least some instances, it may be preferable to fire the shockwaves one at a time in order to avoid any unexpected constructive shockwave formation within the eye, which could result in undesired tissue effects at or outside of the pre-determined target location.

Figure 4:
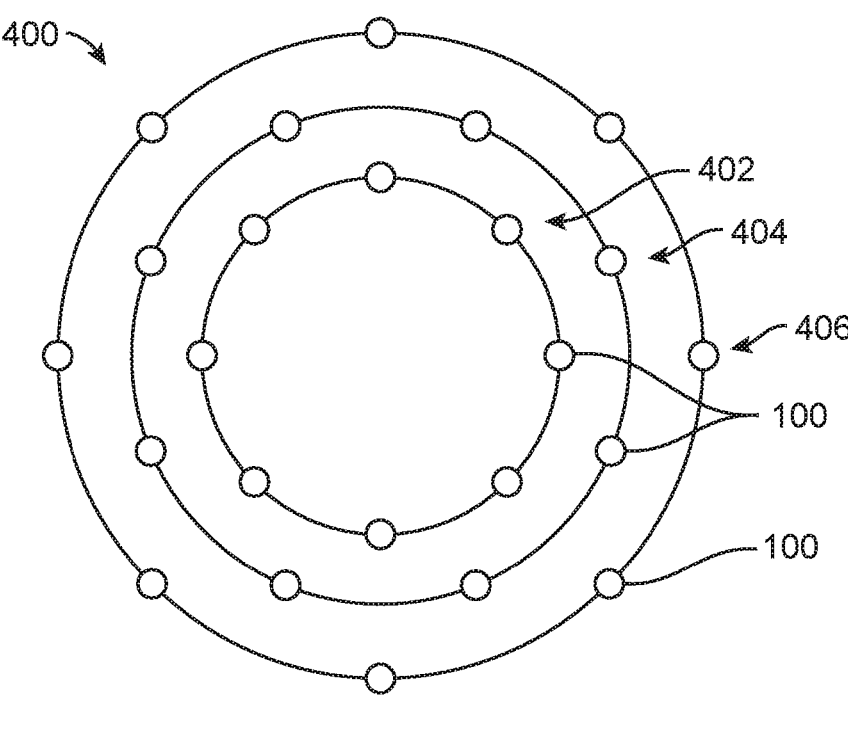
FIG. 4 shows a top view of an array of shockwave generator arranged in multiple rows, in accordance with embodiments.
Figure 5:
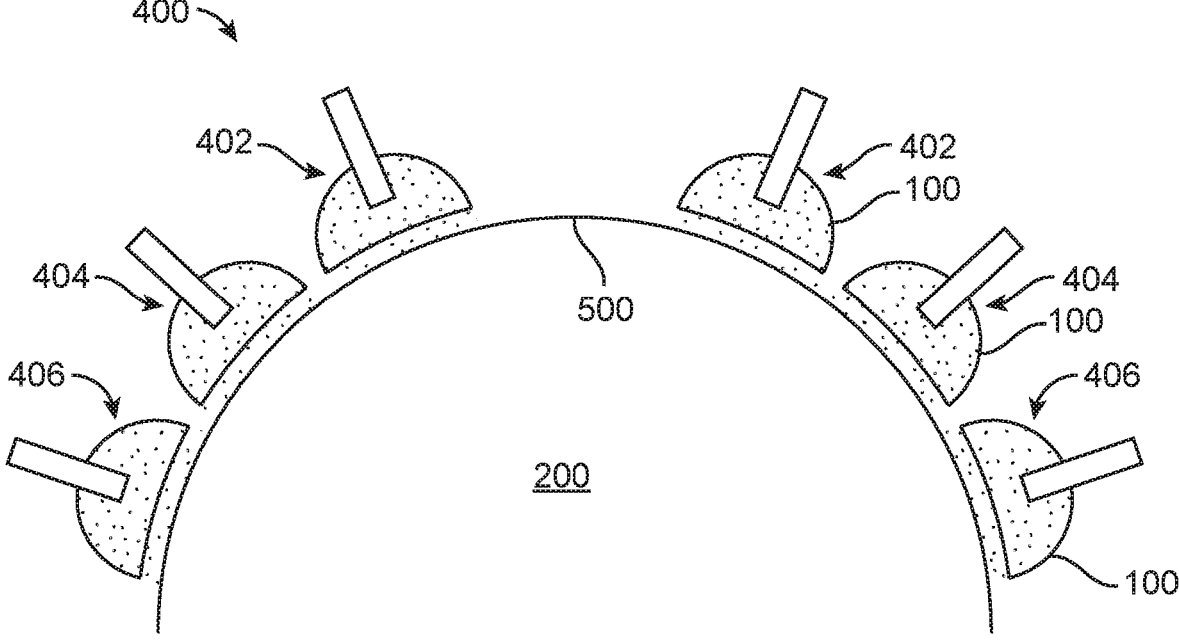
FIG. 5 shows a side view of the array of FIG. 4, in accordance with embodiments.

FIG. 4 shows a top view of an array 400 of shockwave generators 100 arranged in multiple rows. FIG. 5 shows a side view of the array 400 disposed on a surface 500 of an eye 200. The array 400 may comprise at least two rows of shockwave generators 100. For example, the array 400 may comprise a first row 402, a second row 404, and a third row 406. The rows may be positioned such that the shockwaves generated at each row target different locations on or below the surface of the eye.

For example, the first row 402 may be arranged around the limbus as shown in FIG. 3 so as to treat and dilate the trabecular meshwork and/or Schlemm's canal, the second row 404 may be arranged radially outward from the first row 402 and positioned above the pars plicata so as to treat the sclera tissue and/or ciliary body therebelow, and the third row 406 may be arranged radially outward from the second row 404 and positioned above the pars plana so as to treat the scleral tissue and/or ciliary body therebelow, for example to increase porosity. Increased porosity in the mid-stromal near the pars plana and/or pars plicata may, for example, enhance hydraulic conductivity/transport of the supra-choroidal, ciliary, and/or lymphatic fluid outflow pathways of the eye and reduce IOP for glaucoma treatment.

It will be understood by one of ordinary skill in the art based on the teachings herein that the number of rows, spacing between shockwave generators, and position of rows may be configured to treat one or more indications as desired. In some embodiments, the rows may be equally spaced apart from one another. In some embodiments, the rows may be spaced at different distances from one another. In some embodiments, each of the shockwave generators within a row may be spaced the same distance from one another (i.e., equidistant). In some embodiments, one or more of the shockwave generators may be spaced at unequal distances from one or more of the other shockwave generators. In some embodiments, an array of shockwave generators may comprise 1, 2, 3, 4, 5, 6, 7, 8, 9, 10, or more rows as desired. The number of rows may or may not correspond to the number of ophthalmic conditions to be treated in the eye.

Figure 6:
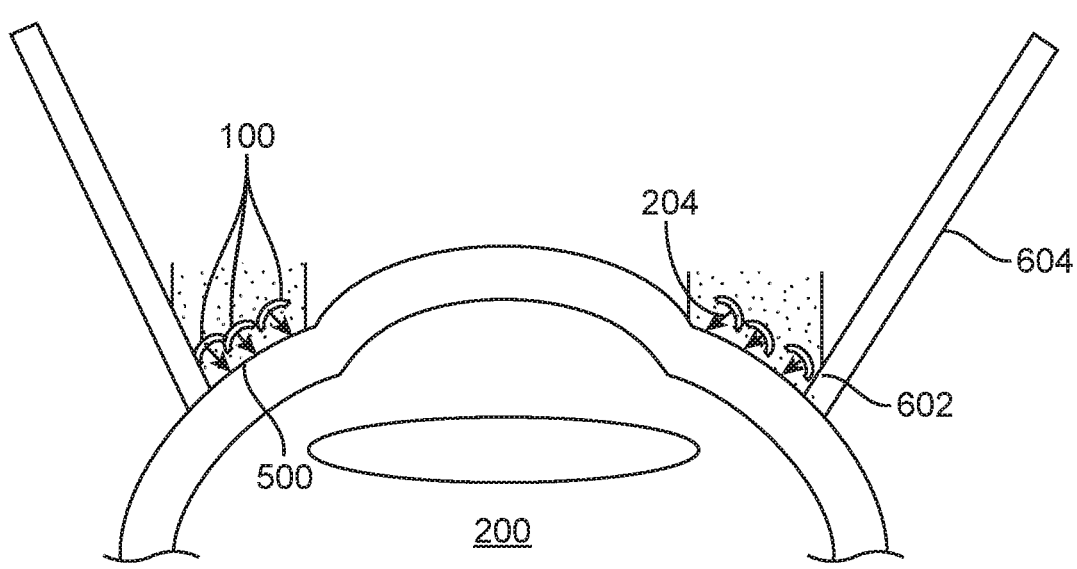
FIG. 6 shows a side cross-sectional view of an exemplary shockwave generator array system comprising a cone coupled to an eye, in accordance with embodiments.

FIG. 6 shows a side cross-sectional view of an exemplary shockwave generator array system 600 comprising a cone coupled to an eye. The system 600 may comprise an array of shockwave generators which may be substantially similar to any of the shockwave generator arrays described herein. For example, the system 600 may comprise an array of shockwave generators 100 disposed in three annular rows spaced as described in FIGS. 4-5. The shockwave generators 100 may be coupled to the surface 500 of the eye 200, for example a sclera or limbus of the eye. In some embodiments, the shockwave generators 100 may comprise individual housings defining fluid-filled chambers as shown in FIG. 1. Alternatively, one or more of the shockwave generators 100 may share a fluid-filled chamber or housing. For example, the shockwave generators 100 may be disposed within a housing configured to create a water channel 602 to bathe the shockwave generators 100 with fluid instead of individual housings. The walls of the water channel 602 may comprise PET. The system 600 may further comprise a cone 604 disposed around the walls of the water channel 602 which may comprise a speculum and a suction ring.

Figure 7:
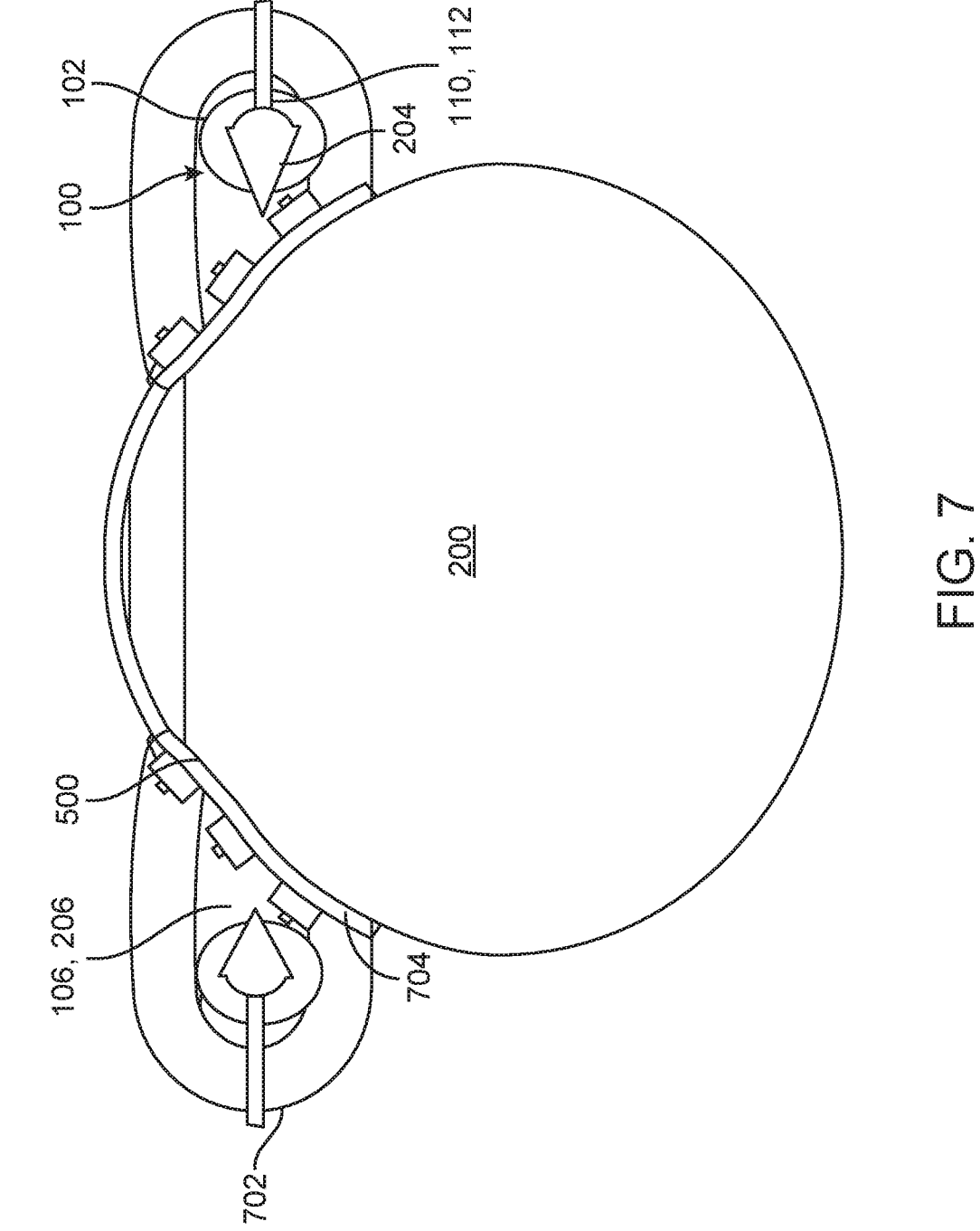
FIG. 7 shows a side cross-sectional view of an exemplary shockwave generator array system comprising a contact lens coupled to an eye, in accordance with embodiments.

FIG. 7 shows a side cross-sectional view of an exemplary shockwave generator array system 700 comprising a contact lens 702 coupled to a surface 500 of an eye 200. The system may comprise one or more shockwave generators 100, which may be substantially similar to any of the shockwave generators described herein. For example, the shockwave generators 100 may comprise a pair of electrodes 110, 112 as described herein. The shockwave generators 100 may be disposed under a contact lens 702. A film 704 may be disposed across the bottom of the contact lens 702 in order to form a fluid-filled chamber 106 around the shockwave generators 100. The film 704 may comprise an eye-contacting surface configured to be coupled to a surface of the eye, which may be substantially similar to any of the eye-contacting surfaces described herein. The fluid-filled chamber 106 may be filled with saline 206 as described herein. In some embodiments, the shockwave generator 100 may further comprise a fluid inlet and a fluid outlet in fluid communication with the fluid-filled chamber 106 as described herein.

In some embodiments, the contact lens 702 may be configured to act as a reflector in order to focus the shockwaves towards a desired pre-determined location. Alternatively, or in combination, one or more reflectors may be coupled to an internal surface of the fluid-filled chamber 106 in order to focus the shockwaves. An inner wall of the fluid filled chamber 106 or a reflector coupled to an internal surface of the fluid-filled chamber 106 may be ellipsoidal in shape.

In some embodiments, the system 700 may comprise an array of shockwave generators 100. For example, the system 700 may comprise eight shockwave generators 100 disposed every 45 degrees along an annular pattern over the surface of the eye.

In some embodiments, the system 700 may be securely coupled to the eye with suction (e.g., with suction rings) on the inner and outer edges of the annular contact lens 702.

In some embodiments, the film may comprise PET.

The film may comprise nylon, polyethylene terephthalate (PET), biaxially-oriented polyethylene terephthalate (Bo-PET), or the like. The film may comprise a suitable polymer such as polytetrafluoroethylene (PTFE), ethylene tetrafluoroethylene (ETFE), fluorinated ethylene propylene (FEP), polyoxymethylene (POM, e.g., DELRIN® available from DuPont), polyether block ester, polyurethane (e.g., Polyurethane 85A), polypropylene (PP), polyvinylchloride (PVC), polyether-ester (e.g., ARNITEL® available from DSM Engineering Plastics), ether or ester based copolymers (for example, butylene/poly(alkylene ether) phthalate and/or other polyester elastomers such as HYTREL® available from DuPont), polyamide (e.g., DURETHAN® available from Bayer or CRISTA D® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (e.g., REXELL®), polyester, polybutylene terephthalate PBT), polyethylene terephthalate (PET), polytrimethylene terephthalate, polyethylene naphthalate (PEN), polyetheretherketone (PEEK), polyimide (PI), polyetherinide (PEI), polyphenylene sulfide (PPS), polyphenylene oxide (PPO), poly paraphenylene terephthalamide (e.g., KEVLAR®), polysulfone, nylon, nylon-2 (such as GRK.A-MID® available from EMS American Grilon), perfluoro (propyl vinyl ether) (PFA), ethylene vinyl alcohol, polyolefin, polystyrene, epoxy, polyvinylidene chloride (PVdC), poly(styrene-A-isobutylene-A-styrene) (for example, SIBS and/or SIBS 50A), polycarbonates, ionomers, biocompatible polymers, other suitable materials, or mixtures, combinations, copolymers thereof, polymer/metal composites, and the like. In some embodiments, the film may comprise a mixture blended with a liquid crystal polymer (LCP) (e.g., up to about 6% LCP).

Figures 8, 9, 10:
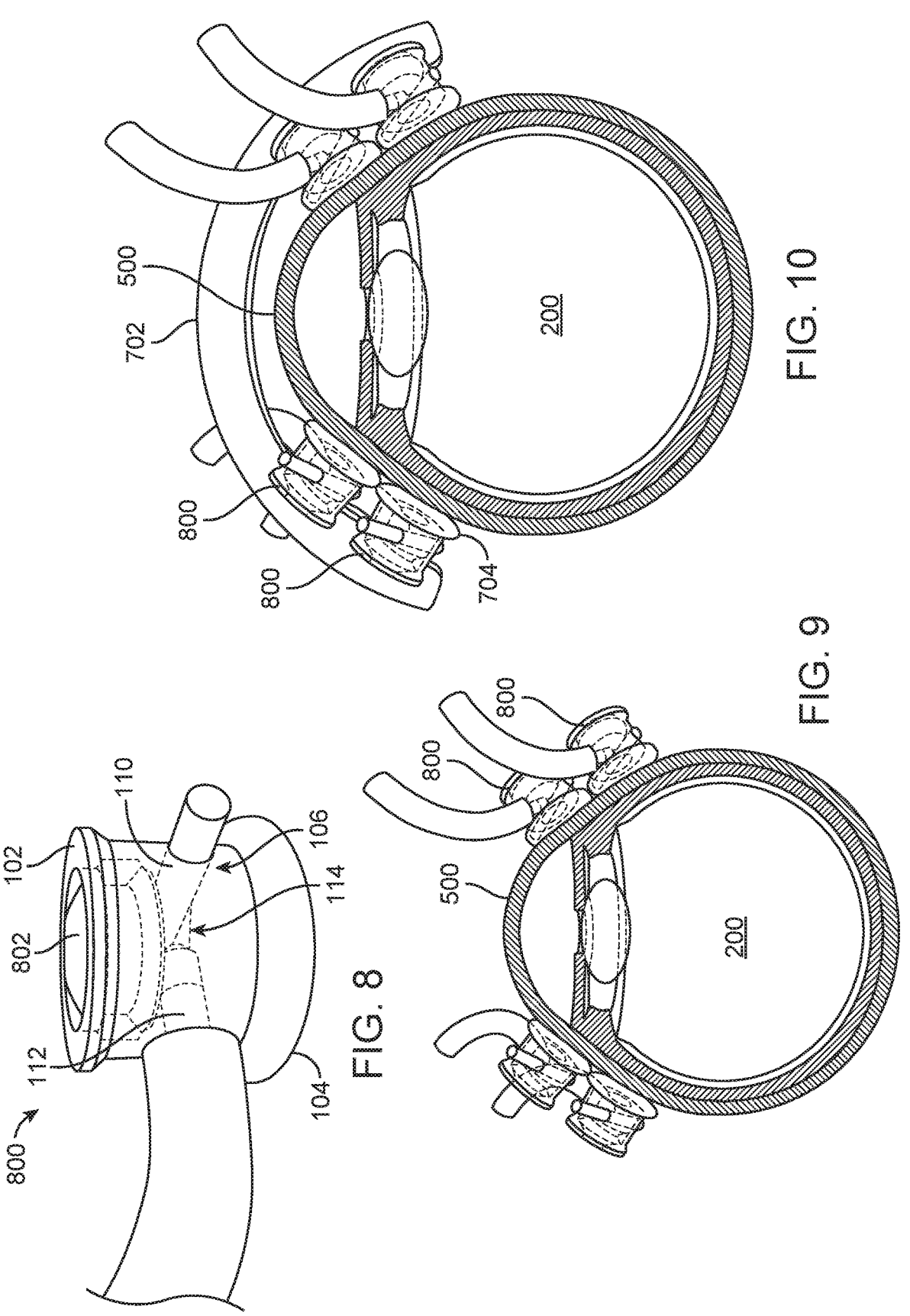
FIG. 8 shows a perspective view of a shockwave generator, in accordance with embodiments.
FIG. 9 shows a side view of a plurality of shockwave generators coupled to an eye, in accordance with embodiments.
FIG. 10 shows a side view of a plurality of shockwave generators coupled to an eye with a contact lens, in accordance with embodiments.

FIG. 8 shows a perspective view of a shockwave generator 800. The shockwave generator 800 may be substantially similar to shockwave generator 100 described herein expect that housing 102 may contain a reflector 802 disposed therein instead of having an inner wall of the housing 102 acting as a reflector. The shockwave generator 100 may comprise a pair of electrodes 110, 112 disposed within housing 102 as described herein. The housing 102 may comprise a fluid-filled chamber 106 and an eye-contacting surface 104. The eye-contacting surface 104 may be configured to be coupled to a surface of an eye of a patient. The first and second electrodes 110, 112 may be co-axially aligned with one another such that a gap 114 is formed between the distal tips of the electrodes 110. The fluid-filled chamber 106 may be filled with saline 206 as described herein. In some embodiments, the shockwave generator 100 may further comprise a fluid inlet and a fluid outlet in fluid communication with the fluid-filled chamber 106 as described herein. The reflector 802 may be configured to help focus the shockwave towards a pre-determined location on or under the surface 500 of the eye 200 as described herein.

FIG. 9 shows a side view of a plurality of shockwave generators 800 coupled to a surface 500 of an eye 200. In some embodiments, a plurality of shockwave generators 800 may be disposed on the surface 500 of the eye at the same time. For example, the plurality of shockwave generators 800 may comprise a plurality of individual shockwave generators or an array of shockwave generators. In some embodiments, the plurality of shockwave generators 800 may comprise a plurality of shockwave generators disposed at a distal end of a handheld probe.

FIG. 10 shows a side view of a plurality of shockwave generators 800 coupled to a surface 500 of an eye with a contact lens 1000. The shockwave generators 800 may be disposed under a contact lens 702. A film 704 may be disposed across the bottom of the contact lens 702 in order to form a fluid-filled chamber 106 around the shockwave generators 800. The film 704 may comprise an eye-contacting surface configured to be coupled to a surface of the eye, which may be substantially similar to any of the eye-contacting surfaces described herein. The fluid-filled chamber 106 may be filled with saline 206 as described herein. In some embodiments, the shockwave generator 800 may further comprise a fluid inlet and a fluid outlet in fluid communication with the fluid-filled chamber 106 as described herein. Alternatively, or in combination, one or more of the plurality of shockwave generators 800 may comprise its own fluid-filled chamber independent of one or more of the other shockwave generators 800. The film 704 may be disposed across the bottom of the contact lens 702 in order to form the individual fluid-filled chambers 106 of the shockwave generators 800 and each shockwave generator 800 may have a dedicated fluid inlet and fluid outlet.

Figure 11:
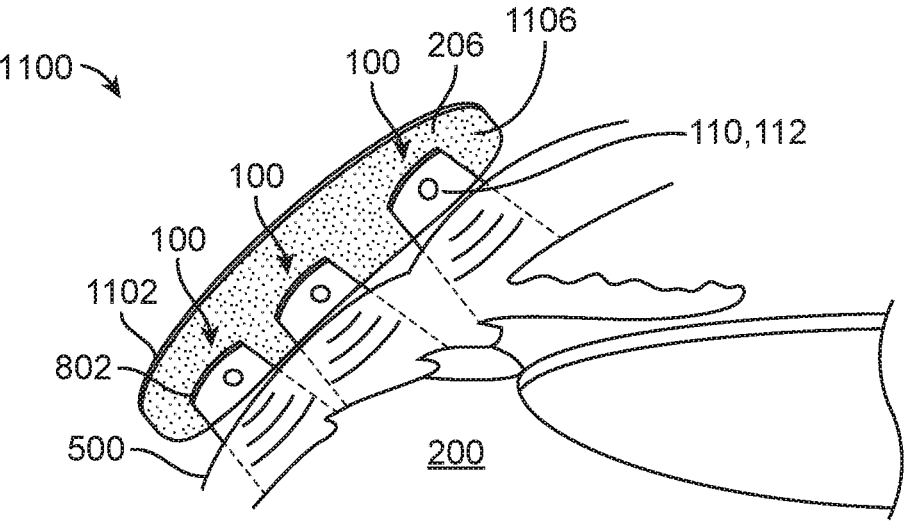
FIG. 11 shows a side cross-sectional view of a plurality of shockwave generators coupled to an eye with a contact balloon, in accordance with embodiments.

FIG. 11 shows a side cross-sectional view of a plurality of shockwave generators 100 coupled to a surface 500 of an eye 200 with a contact balloon (also referred to herein as a fluidic cushion) 1100. The contact balloon 1100 may comprise an inflatable outer housing 102 with a plurality of shockwave generators 100 embedded therein. The outer housing 1102 may define an inner chamber 1106 which may be filled with a fluid such as saline 206 in order to inflate the outer housing 1102 prior to, during, or after placement of the contact balloon 1100 on a surface 500 of the eye 200 (e.g, adjacent the limbus, sclera, eyelids, etc. as described herein). Each shockwave generator 100 may comprise a pair of coaxially-aligned electrodes 110, 112 and a reflector 802 as described herein. The electrodes 110, 112 may be coupled to a voltage pulse generator as described herein. The reflector 802 may be configured to help focus the shockwave towards a pre-determined location on or under the surface 500 of the eye 200 as described herein. In some embodiments, the shockwave generators 100 may be arranged in a plurality of annular rows as described herein in order to target multiple locations of the eye. For example, a first row of shockwave generators may be disposed adjacent the limbus and configured to focus shockwaves to the trabecular meshwork and Schlemm's canal. A second row of shockwave generators may be disposed radially outward therefrom adjacent the pars plicata and a third row of shockwave generators may be radially outward from the second row adjacent the pars plana. The second and/or third row of shockwave generators may be configured to focus shockwaves to the sclera, the pars plicata, the pars plana, the ciliary body, the IVZs, and/or the PVZs, for example.

In some embodiments, the fluid filling the inner chamber 1106 of the contact balloon 1100 may be a chilled or temperature controlled-liquid.

The outer housing 1102 may comprise a compliant material. Alternatively, or in combination, at least a portion of the outer housing 1102 may comprise a non-compliant material.

The outer housing 1102 may comprise any biocompatible plastic known to one of skill in the art.

In some embodiments, a coupling fluid or gel may be on the eye-contacting surface of the outer housing in order to facilitate contact between the eye-contacting surface and the surface of the eye and/or in order to facilitate transmission of the shockwave from the shockwave generator to the eye.

In some embodiments, a therapeutic substance may be disposed between the eye-contacting surface and the surface of the eye. The therapeutic substance may, for example, be provided in a layer bonded to the eye-contacting surface. In some embodiments, the therapeutic substance may comprise a microcapsule formed of a polymer, a starch, and/or glucose. Delivery of the shockwaves from the shockwave generators within the housing to the pre-determined location of the eye may facilitate delivery of the therapeutic substance to the eye.

In some embodiments, any of the shockwave generators described herein may be configured to facilitate transport of small molecular weight molecules such as methylene blue, riboflavin, or therapeutic small molecules.

Figure 12:
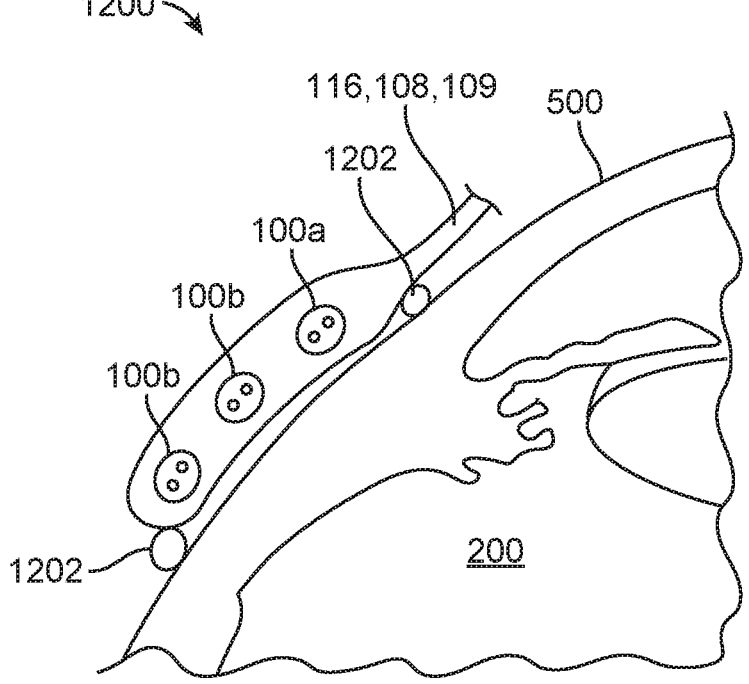
FIG. 12 shows a side cross-sectional view of a plurality of shockwave generators coupled to an eye with a contact balloon, in accordance with embodiments.

FIG. 12 shows a side cross-sectional view of a plurality of shockwave generators coupled to an eye with a contact balloon 1200. The contact balloon 1200 may be substantially similar to contact balloon 1100 except that it may comprise a plurality of non-homologous shockwave generators 100. For example, the contact balloon 1200 may comprise one or more shockwave generators 100*a* configured to generate a focused shockwave and one or more shockwave generators 100*b* configured to generate an unfocused shockwave. By providing a plurality of differently-focusing shockwave generators 100, it may be possible to treat multiple pre-determined locations and/or induce multiple biological effects within the same pre-determined location using a single array of shockwave generators. The contact balloon 1200 may be coupled to the eye with suction rings 1202 on the inner and outer edges of the annular contact balloon 1200.

Figure 13:
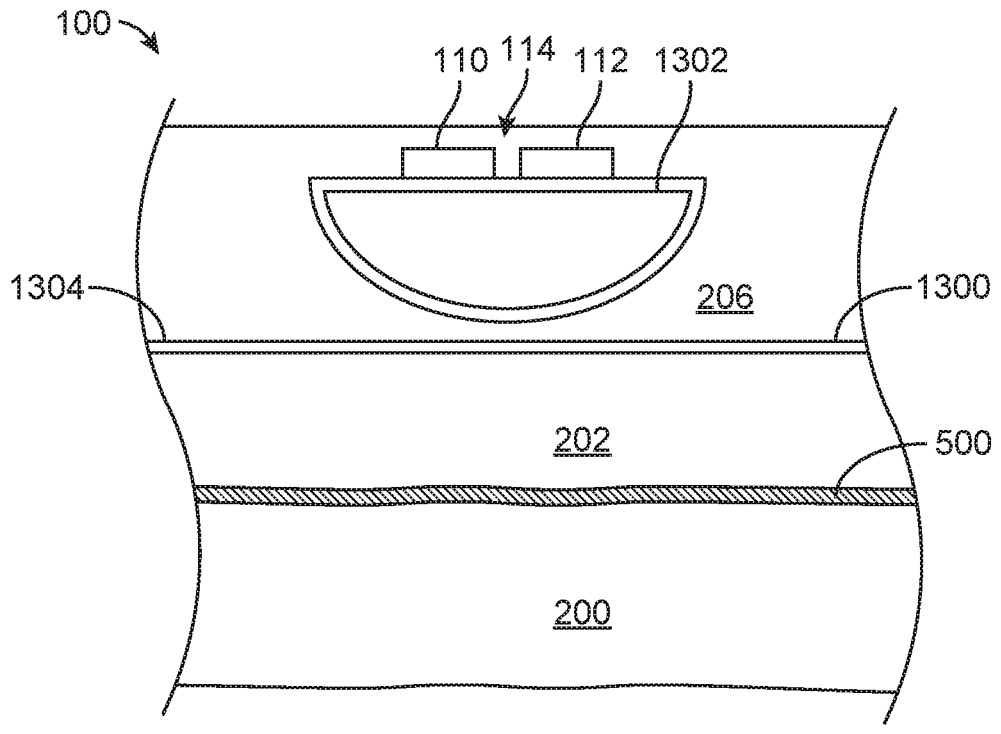
FIG. 13 shows an exploded side view of an exemplary shockwave generator adjacent an eye, in accordance with embodiments.

FIG. 13 shows an exploded side view of an exemplary shockwave generator 100 adjacent an eye. The shockwave generator 100 may be embedded within a fluid-filled contact balloon 1300 as described herein. The shockwave generators 100 may comprise a pair of electrodes 110, 112 having a gap 114 between the tips thereof configured to generate an electrical arc therebetween. The contact balloon 1300 may be filled with a fluid such as saline 206 and the resultant shockwave may propagate through the fluid 206 (which may act as an acoustic window) as described herein. An acoustic reflector or acoustic lens 1302 may be disposed above the electrodes 110, 112 in order to focus the shockwave towards a pre-determined location on or below a surface 500 of the eye 200 as described herein. The reflector 1302 may, for example, have a convex shape. An eye-contacting surface 1304 of the contact balloon 1300 may be coupled directly or indirectly (e.g., via a gel or saline interface 202 therebetween) to the surface 500 of the eye 200. The surface 500 of the eye may, for example, comprise a conjunctiva or a cornea of the eye 200.

Figure 14:
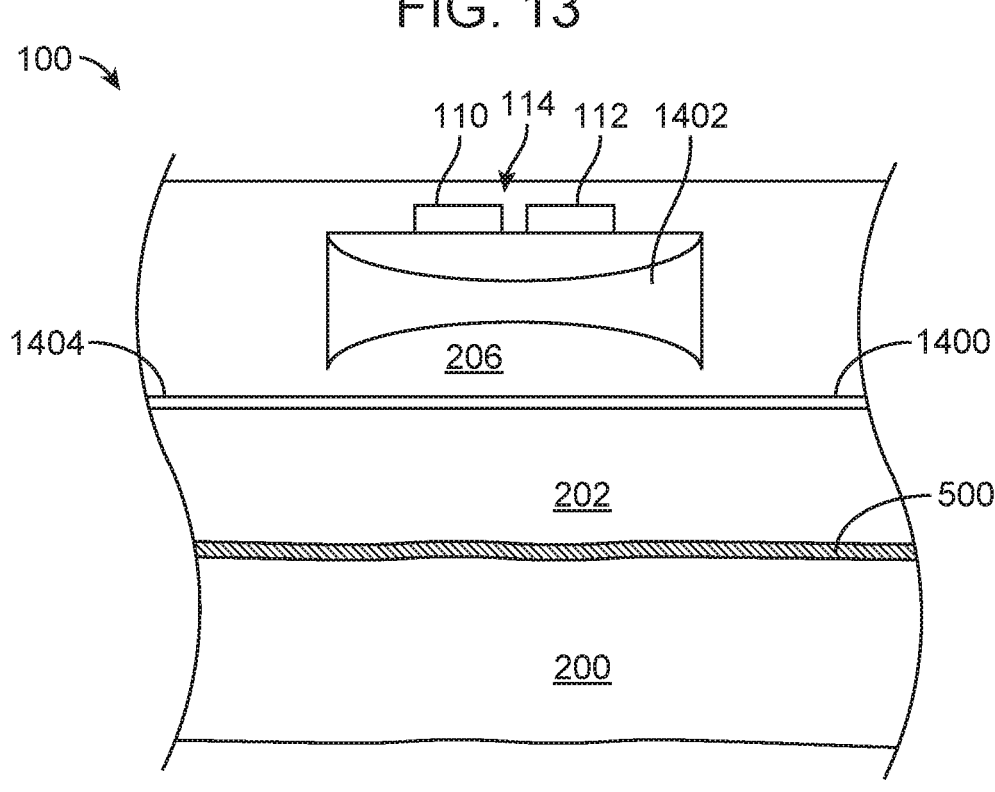
FIG. 14 shows an exploded side view of another exemplary shockwave generator adjacent an eye, in accordance with embodiments.

FIG. 14 shows an exploded side view of another exemplary shockwave generator 100 adjacent an eye 200. The shockwave generator 100 may be embedded within a contact balloon 1400 as described herein. The shockwave generator 100 may be substantially similar to the shockwave generator shown in FIG. 13 except that the reflector 1402 may have a concave shape. An eye-contacting surface 1404 of the contact balloon 1400 may be coupled directly or indirectly (e.g., via a gel or saline interface 202 therebetween) to the surface 500 of the eye 200.

FIG. 15 shows a side cross-sectional view of a plurality of shockwave generators 100 coupled to an eye 200 with a contact balloon 150. FIG. 16 shows a perspective view of the system of FIG. 15 coupled to an eye 200. The contact balloon 1500 may comprise an inflatable outer housing 1502 with a plurality of shockwave generators 100 embedded therein. The outer housing 1502 may define an inner chamber 1506 which may be filled with a fluid 206 such as saline in order to inflate the outer housing 1502 prior to, during, or after placement of the contact balloon 1500 on a surface 500 of the eye 200 (e.g., adjacent the limbus, sclera, eyelids, etc. as described herein). Each shockwave generator 100 may comprise a pair of coaxially-aligned electrodes and a reflector as described herein. The reflector may be configured to help focus the shockwave towards a pre-determined location on or under the surface of the eye as described herein. In some embodiments, the shockwave generators 100 may be arranged in a plurality of annular rows coupled by wiring in order to target multiple locations of the eye. For example, a first row of shockwave generators may be disposed adjacent the limbus and configured to focus shockwaves to the trabecular meshwork and Schlemm's canal. A second row of shockwave generators may be disposed radially outward therefrom adjacent the pars plicata and a third row of shockwave generators may be radially outward from the second row adjacent the pars plana. The second and/or third row of shockwave generators may be configured to focus shockwaves to the sclera, the pars plicata, the pars plana, the ciliary body, the IVZs, and/or the PVZs, for example.

In some embodiments, the fluid 206 filling the inner chamber of the contact balloon 1500 may be a chilled or temperature controlled-liquid.

The outer housing 1502 may comprise a compliant material. Alternatively, or in combination, at least a portion of the outer housing may comprise a non-compliant material.

The outer housing 1502 may comprise a biocompatible plastic as will be known to one of ordinary skill in the art. For example, the outer housing may comprise PMMA or other shape-forming biocompatible materials.

In some embodiments, an eye-contacting surface 1504 of the outer housing may be configured to conform to the surface of the eye in a manner similar to a traditional soft contact lens.

In some embodiments, a coupling fluid or gel may be on the eye-contacting surface of the outer housing in order to facilitate contact between the eye-contacting surface and the surface of the eye and/or in order to facilitate transmission of the shockwave from the shockwave generator to the eye.

Figures 17, 18:
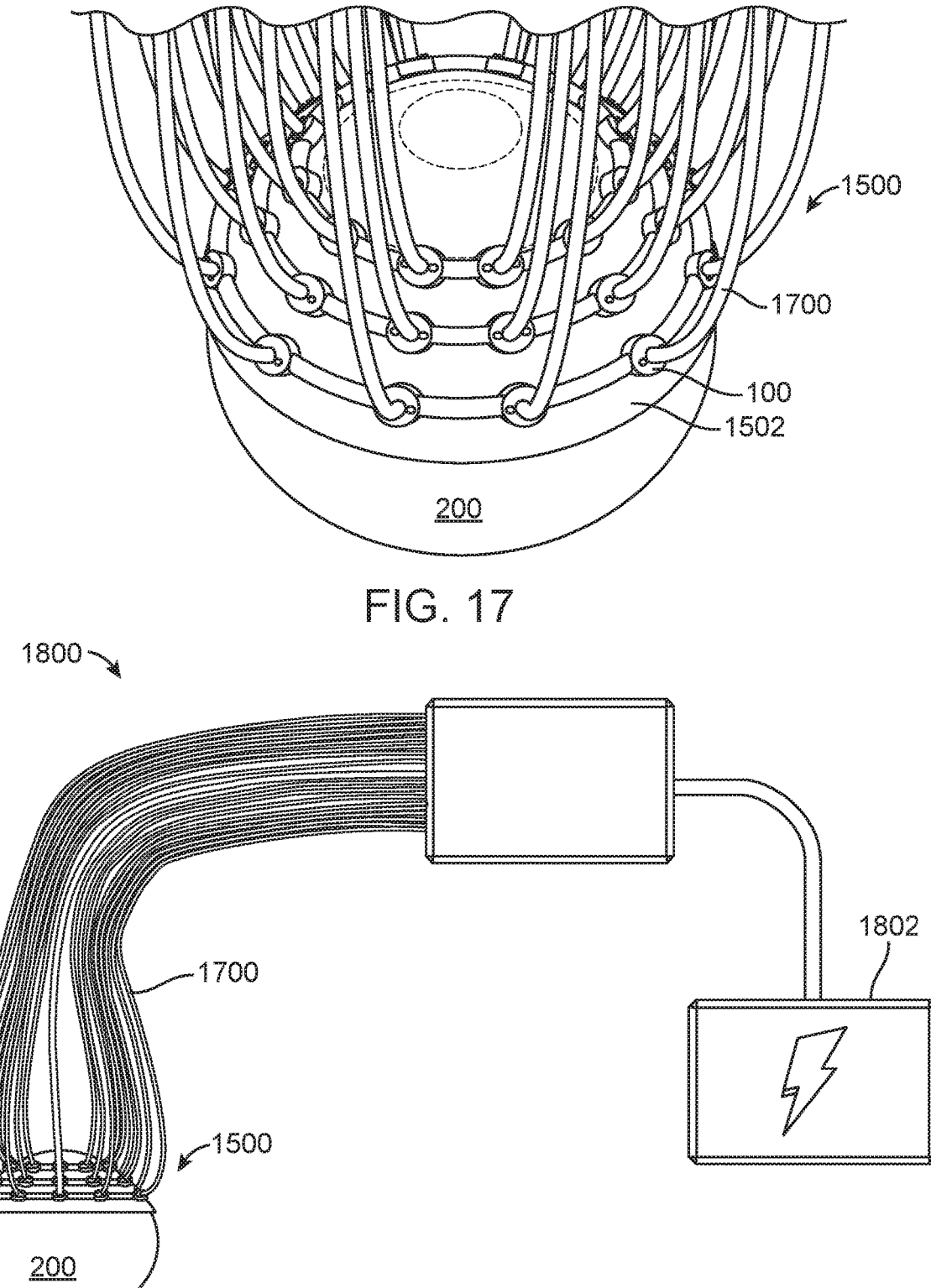
FIG. 17 shows a perspective view of the system of FIG. 15 coupled to additional tubing and/or wiring, in accordance with embodiments.
FIG. 18 shows a side view of the system of FIG. 17 with the tubing and/or wiring coupled to a power source, in accordance with embodiments.

FIG. 17 shows a perspective view of the system 1500 of FIG. 15 coupled to additional tubing and/or wiring 1700. In some embodiments, the additional tubing and/or or wiring 1700 may comprise a cable comprising an inner conductor and an outer conductive shield insulated from the inner conductor. A first one of the coaxially-arranged electrodes may be at least in part formed by the center conductor of the cable and a second one of the coaxially-arranged electrodes may be at least in part formed by the outer conductive shield of the cable.

FIG. 18 shows a side view of a system 1800 comprising the system 1500 of FIG. 17 with the tubing and/or wiring 1700 coupled to a power source 1802. The tubing and/or wiring 1700 may also be coupled to a fluid source for inflation of the contact balloon and/or fluid cycling for conductivity sampling as described herein.

The power source 1802 may comprise a high voltage pulse generator. In some embodiments, the power source 1802 may comprise a high voltage capacitor charging power supply. Gated high voltage electronics drivers may be coupled to the shockwave generator(s) 100 and may be able to control the driving voltage of the electrodes responsive to safety feedback mechanisms such as maximum current (e.g., as sensed with a current sensor as described herein), dwell time to current start, temperature rise (e.g., of the electrodes, of the fluid, or at the surface of the eye), peak pressure, and/or elasticity changes.

The power supply 1802 may be on the order of about 1 kV to about 10 kV.

Any of the systems described herein may comprise a processor (e.g., processor 7002 shown in FIG. 70) having a tangible medium (e.g., a RAM). The processor may be configured with one or more instructions to perform any of the methods and/or any one of the steps and sub-steps of the methods or treatments described herein. The processor may comprise memory having instructions to perform the method, and the processor may comprise a processor system configured to perform the method for example. In many embodiments, the processor comprises array logic such as programmable array logic ("PAL") configured to perform one or more steps of any of the methods or treatments described herein, for example.

The processor may comprise one or more instructions of a treatment program embodied on a tangible medium such as a computer memory or a gate array in order to execute one or more steps of a treatment method as disclosed herein. The processor may comprise instructions to treat a patient in accordance with embodiments described herein.

The processor may be operatively coupled to the energy source and configured with instructions to deliver energy to the shockwave generator(s) with the treatment parameters described herein. For example, the processor may be configured with instructions to provide a plurality of shockwaves to a pre-determined location on or below a surface of the eye with a desired treatment pattern and parameters. In embodiments where more than one shockwave generator is coupled to the eye at a time, the processor may be configured with instructions to sequentially or simultaneously deliver energy to the plurality of shockwave generators based on a pre-determined treatment pattern input by the user or generated by the processor based on a user input (e.g., an image or a desired treatment effect).

Any of the systems described herein may comprise an imaging system, for example an ultrasound biomicroscopy (UBM), ultrasound (US) imaging, and/or optical coherence tomography (OCT) apparatus or system. The imaging system may be used to capture one or more images of the eye before, during, or after treatment as described herein. A processor or controller may be coupled to the energy source and the imaging system and be configured with instructions to deliver energy to the shockwave generators and image the tissue during treatment. The system may also comprise a display coupled to the processor that allows the user to visualize the tissue prior to, before, or after treatment. The display may show images which allow the user to see the tissue treated and plan the treatment. Images shown on the display may be provided in real-time and can be used to prior to treatment to allow the user to align the tissue and/or monitor the tissue effects of treatment (e.g., cavitation) in order to make sure that unintended effects of treatment aren't occurring (e.g., structures of the eye changing locations relative to one another when not desired, etc.).

For example, one or more shockwave generators may comprise a central aperture configured to allow an OCT or wavefront imaging system or sensor to be integrated therein. In some embodiments, a plurality of shockwave generators may be disposed in an annular ring around a central imaging system to enable for passive cavitation monitoring. It will be understood by one or ordinary skill in the art that many configurations of shockwave generator(s) and imaging apparatus(es) may be generated based on the description herein.

Figure 19:
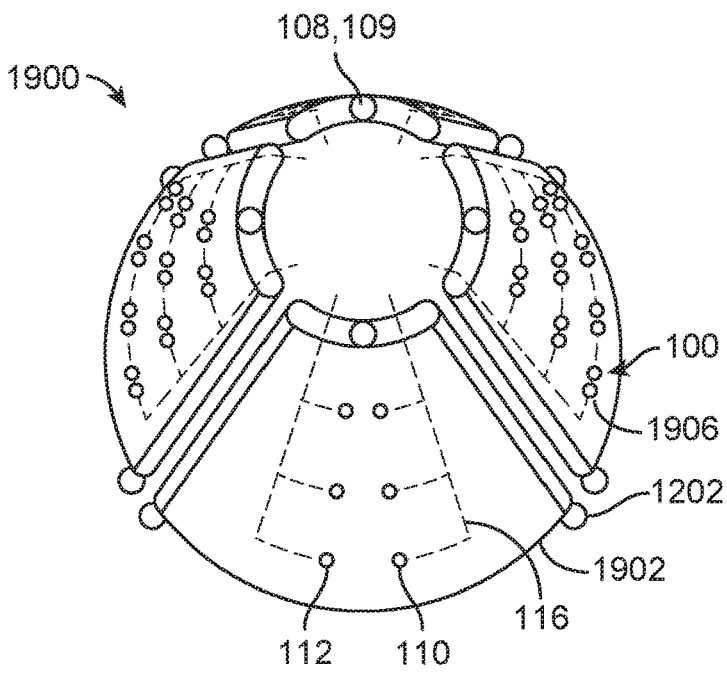
FIG. 19 shows a perspective view of a contact balloon comprising a plurality of shockwave generators embedded therein, in accordance with embodiments.

FIG. 19 shows a perspective view of a contact balloon 1900 comprising a plurality of shockwave generators 100 embedded therein. The contact balloon 1900 may be substantially similar to any of the contact balloons described herein. The plurality of shockwave generators 100 may be substantially similar to any of the shockwave generators described herein. The shockwave generators 100 may comprise an array of shockwave generators as described herein. For example, the array of shockwave generators may be coupled to a power source via wires 116 in series or in parallel as described herein. The array of shockwave generators may be disposed within a fluid-filled chamber 1906 of the contact balloon 1900 as described herein. The fluid-filled chamber 1906 may comprise a fluid, such as saline, as described herein. The contact balloon 1900 may comprise an expandable fluid-filled chamber 1906 configured to expand when a fluid is introduced therein as described herein. The contact balloon 1900 may comprise a fluid inlet 108 and a fluid outlet 109 as described herein. The contact balloon 1900 may be secured to the eye with suction 1202 (e.g., with one or more suction rings) as described herein.

Figure 20:
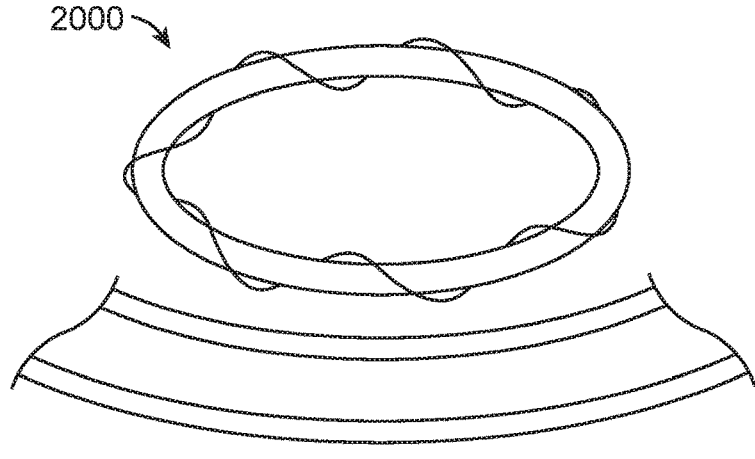
FIG. 20 shows a partial perspective view of a plurality of stacked ring conductor shockwave generators, in accordance with embodiments.
Figure 21:
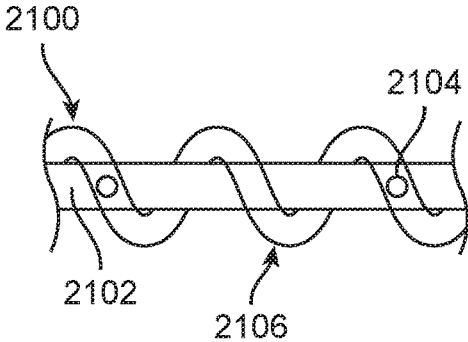
FIG. 21 shows an exploded view of the ring conductor shockwave generator of FIG. 20, in accordance with embodiments.

FIG. 20 shows a partial perspective view of a plurality of stacked ring conductor shockwave generators 2000. FIG. 21 shows an exploded view of the ring conductor shockwave generator 2000 of FIG. 20. The stacked ring conductor shockwave generators 2000 may comprise a plurality of ring conductors "stacked" around one another such that adjacent rings lie within a pre-determined distance of one another. The ring conductors may comprise insulated conductors 2100 wrapped around an insulated structural ring 2102. The insulated ring conductors 2102 may comprise one or more openings 2104 in the insulation, which may be spaced at a pre-determined distance from another opening in the insulation of the same or an adjacent ring conductor in order to form a gap in which a shockwave can form in a manner substantially similar to that described herein with respect to concentric electrode embodiments. The exposed conductor openings 2104 may be used to generate a shockwave as described herein. In some embodiments, an insulated conductor 2100 and an exposed or uninsulated conductor 2106 may be wrapped around an insulated structural ring 2102 such that loops of each alternate from exposed to insulated and back to exposed around the ring 2102. Openings 2104 in the insulated conductor 2100 may be spaced at a predetermined distance from an exposed conductor 2106 of the same or an adjacent ring conductor in order to form the gap in which a shockwave can for as described herein. The stacked ring conductor shockwave generators 2000 may be disposed within a fluid (e.g., saline) environment such as a contact lens or balloon contact lens as described herein.

Figure 22:
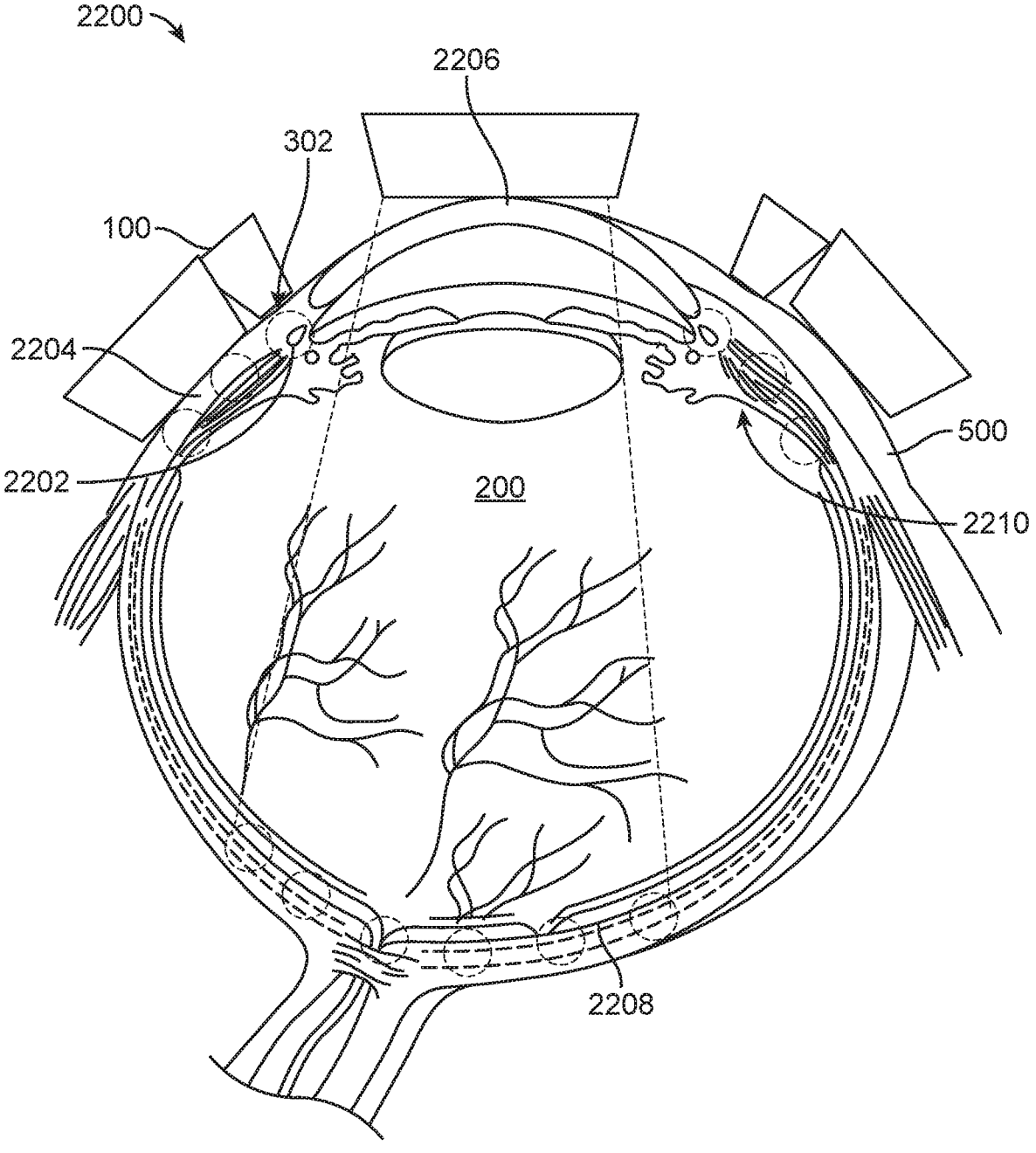
FIG. 22 shows an exemplary treatment pattern for glaucoma, in accordance with embodiments.

FIG. 22 shows an exemplary treatment pattern for glaucoma. One or more shockwave generators, for example an array 2200 of shockwave generators 100, may be disposed on a surface 500 of an eye 200 as described herein. The shockwave generator(s) 100 may be substantially similar to any of the shockwave generators described herein. The shockwave generators may be configured to target one or more tissue locations in the eye 200 in order to reduce IOP. For example, a plurality of shockwave generators may be placed above the limbus 302 of the eye as described herein and the shockwaves may be focused towards the trabecular meshwork and/or Schlemm's canal 2202 in order to cause dilation thereof and improve fluid outflow from the eye. Alternatively, or in combination, a plurality of shockwave generators may be placed above the pars plana as described herein and the shockwaves may be focused to the sclera 2204 and/or the ciliary body 2210 in order to generate microporation therein and enhance uveoscleral outflow. Alternatively, or in combination, one or more shockwave generators may be placed on the cornea 2206 and the shockwaves may be focused to the retina 2208 in order to provide low energy acoustic stimulation thereto for vasodilation and neovasculaization, which may enhance neurotrophic delay in retinal ganglion cell (RGC) and/or retinal pigment epithelial (RPE) cell degeneration. Retinal targeting may also stimulate RPE cells to reset the homeostasis IOP set point such that aqueous generation is curtailed (and IOP is subsequently reduced).

Figure 23:
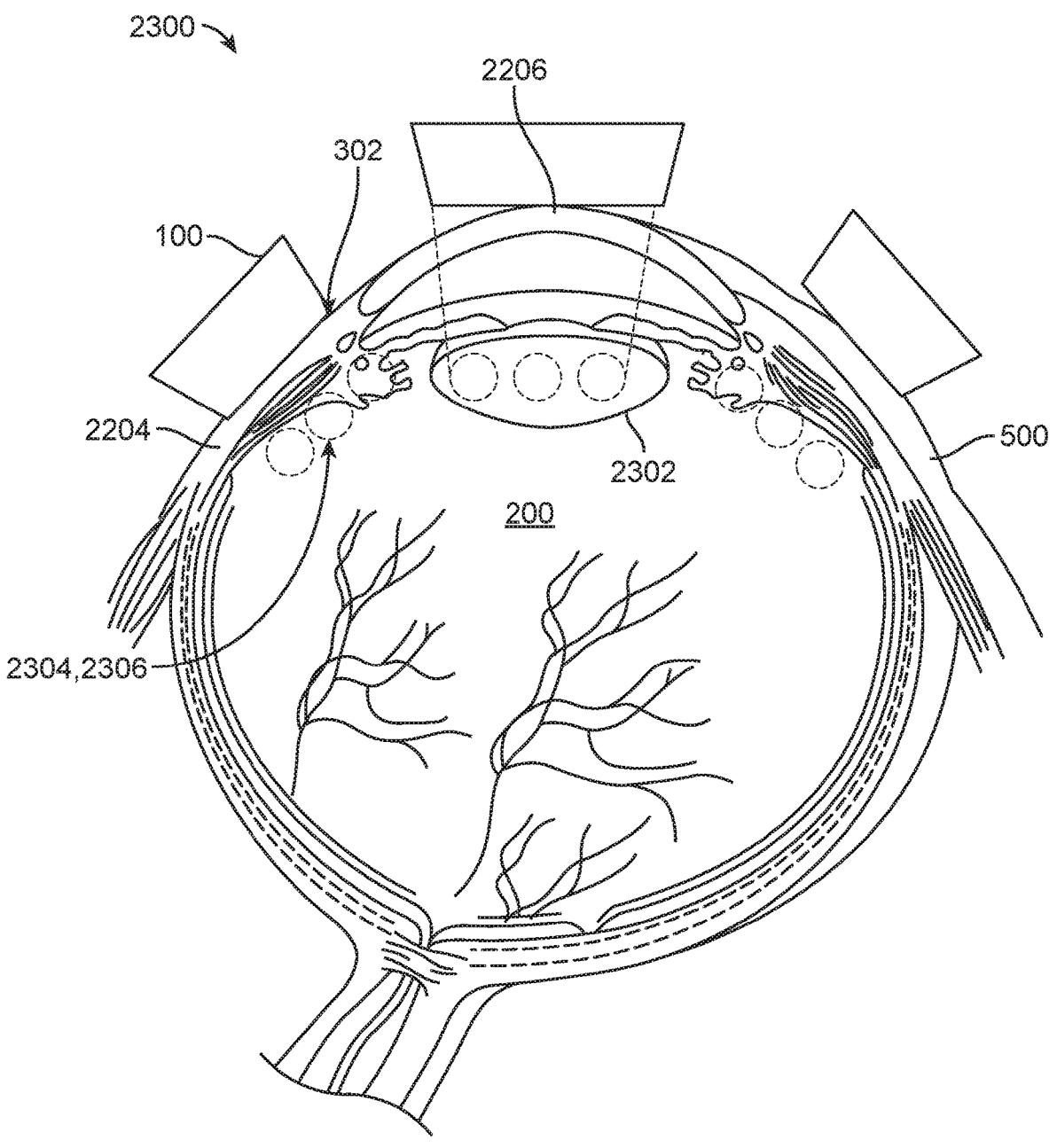
FIG. 23 shows an exemplary treatment pattern for presbyopia, in accordance with embodiments.

FIG. 23 shows an exemplary treatment pattern for presbyopia. One or more shockwave generators, for example an array 2300 of shockwave generators 100, may be disposed on a surface 500 of an eye 200 as described herein. The shockwave generator(s) 100 may be substantially similar to any of the shockwave generators described herein. The shockwave generators may be configured to target one or more tissue locations in the eye 200 in order improve the accommodative amplitude of the eye. For example, a plurality of shockwave generators may be placed above a sclera 2204 of the eye and the shockwaves may be focused towards the IVZ 2304 and/or PVZ 2306 in order to cause disaggreration thereof and improve movement thereof. Alternatively, or in combination, a plurality of shockwave generators may be placed above the pars plana and the shockwaves may be focused to the sclera 2204 in order to generate microporation therein and enhance compliance and anterior and centripetal motion of the ciliary apex thereof. Alternatively, or in combination, one or more shockwave generators may be placed on the cornea 2206 and the shockwaves may be focused to the lens 2302 (native or intraocular lens (TOL)) in order to cause lenticular dis-agglomeration and softening and initiate LEC apoptosis. Different effects and treatment locations may be targeted by changing the depth of focus (e.g., by the ellisoidal shape of the reflecting element), adjusting the amount of energy delivered per shockwave (e.g., by adjusting the voltage delivered to the electrodes or the power of the laser), adjusting the repetition rate of treatment, etc.

Figure 24:
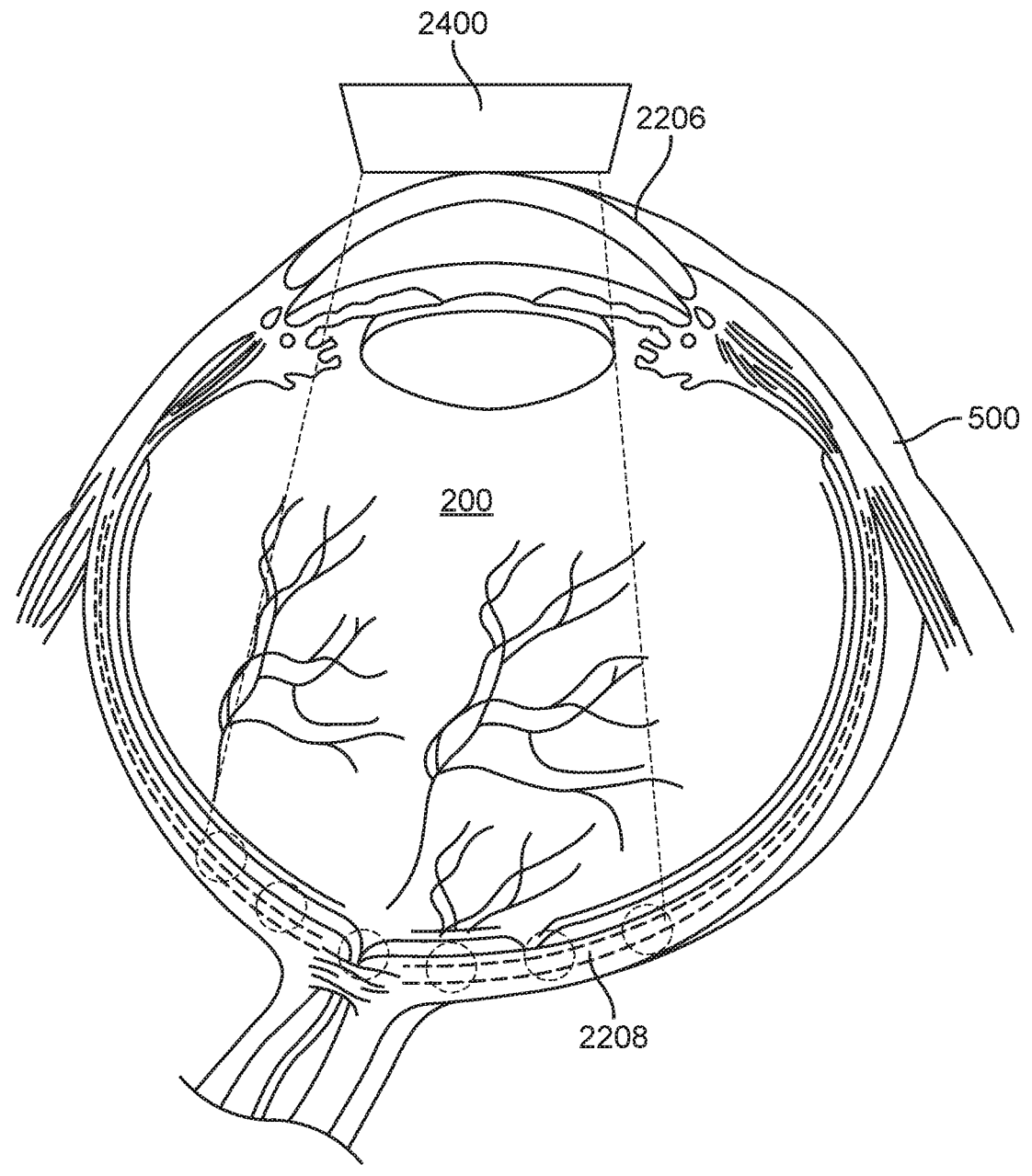
FIG. 24 shows an exemplary treatment pattern for AMD, in accordance with embodiments.

FIG. 24 shows an exemplary treatment pattern for AMD. A shockwave generator 2400, which may be substantially similar to any of the shockwave generators described herein, may be disposed on a surface of an eye. The shockwave generator 2400 may be configured to focus a shockwave onto the retina 2208. In some embodiments, a plurality of shockwave generators 2400 may be disposed on the surface 500 of the eye 200 and configured to direct shockwaves to a plurality of locations on the retina. For example, the shockwaves may be directed pan-macular, to the peri-fovea, and/or to the central retina (e.g., the shockwaves may be directed to a central 6 mm diameter portion of the retina). The shockwaves may be directed trans-corneally towards the retina 2208 without heating or damaging any tissue therebetween. Shockwave treatment of the central retina may stimulate vascularization and vasodilation while treatment of the retinal ganglion cell (RGC) and/or retinal vascular plexus for neuro- and/or endothelial protection in order to reduce or reverse the progression of AMD.

Figures 25, 26:
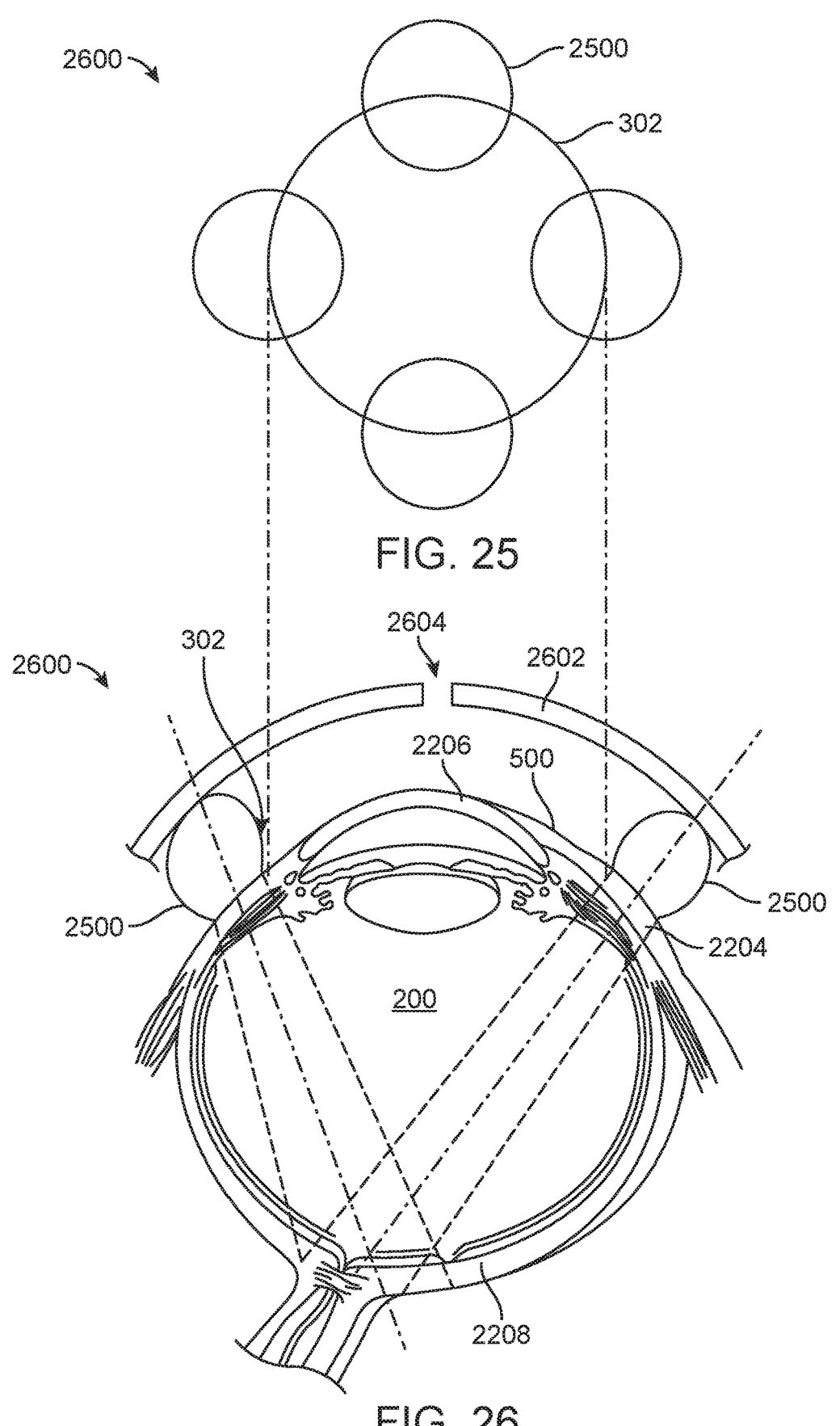
FIG. 25 shows a top view of an exemplary treatment system for AMD, in accordance with embodiments.
FIG. 26 shows a side cross-sectional view of the system of FIG. 25, in accordance with embodiments.

FIG. 25 shows a top view of an exemplary treatment system 2600 for AMD. FIG. 26 shows a side cross-sectional view of the system 2600 of FIG. 25. An array of large (e.g., 5 mm outer diameter) shockwave generators 2500 may be disposed in an annular pattern adjacent the limbus 302 of the eye 200 (e.g., about 11 mm diameter annulus). By using large shockwave generators 2500, the system 2600 may be able to deliver biologically-relevant shockwave energy to greater focal depths within the eye than may be possible with a smaller shockwave generator. The array may comprise four shockwave generators 2500, for example. The shockwave generators 2500 may be substantially similar to any of the shockwave generators described herein. The array of shockwave generators 2500 may be disposed on a surface 500, for example the sclera 2204, of an eye 200. In some instances, it may be beneficial to direct the shockwaves trans-sclerally instead of through the cornea 2206. The array of shockwave generators 2500 may be configured to treat one or more pre-determined locations on the retina 2208, for example the perifovea (e.g., in an annular treatment pattern of about 6 mm in diameter and about 23 mm deep within the eye) in order to stimulate vascularization and vasodilation within the retina in order to reduce or reverse the progression of AMD. Vascular effects may, for example, be stimulated by directing a low energy broad shockwave to the fovea within a 5.5 mm diameter annular region on the center of the retina for pan-macular exposure. Treating the perifovea may lead to greater recruitment of RPE cells and stimulation thereof to produce vasodilation and choroidal neovascularization compare to foveal treatment. Shockwaves may be delivered to the retina without injuring the optic nerve.

The array 2600 may be disposed within a contact lens 2602 as described herein. In some embodiments, the contact lens 2602 may comprise an imaging port 2604 configured to receive an imaging apparatus, for example an OCT transducer, therein. Treatment may be monitored with the imaging apparatus as described herein.

Figure 27:
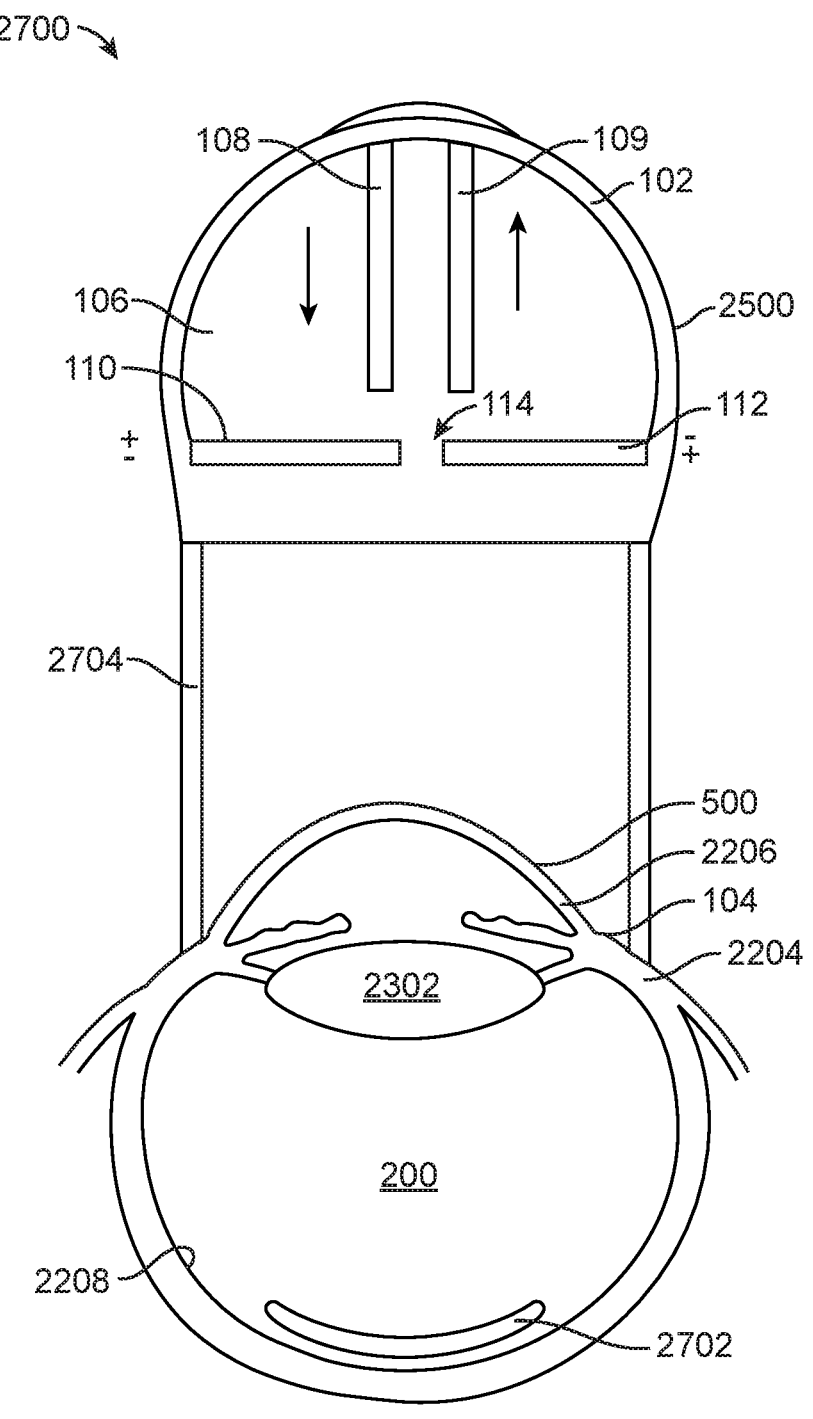
FIG. 27 shows another exemplary treatment system for AMD, in accordance with embodiments.

FIG. 27 shows another exemplary treatment system 2700 for AMD. The system 2700 may comprise a large diameter shockwave generator 2500 configured to deliver shockwaves onto the retina 2208. The shockwave generator 2500 may be substantially similar to any of the shockwave generators described herein. For example, the shockwave generator 2500 may comprise a first electrode 110 and a second electrode 112 disposed within housing 102. The housing 102 may comprise a fluid-filled chamber 106 and an eye-contacting surface 104. The fluid-filled chamber 106 may be configured to act as a reflector in order to focus the shockwaves towards a desired pre-determined location. Alternatively, or in combination, one or more reflectors may be coupled to an internal surface of the fluid-filled chamber 106 in order to focus the shockwaves. An inner wall of the fluid filled chamber 106 or a reflector coupled to an internal surface of the fluid-filled chamber 106 may be ellipsoidal in shape. The conjugate foci of the ellipse 2702 may be configured such that the shockwaves are focused through the crystalline lens 2302 of the eye, which then refracts the shockwaves onto the retina 2208 of the eye. The shockwave generator 2500 may comprise an ellipsoidal footprint over the sclera 2204 that is on the order of 12 mm aperture. Due to the large size of the shockwave generator 2500, the pre-determined location on the retina 2208 may be relatively large (e.g., 6 mm in diameter) compared to smaller shock-wave generators which may facilitate quicker treatment of the retina 2208. The eye-contacting surface 104 may be configured to be coupled to a surface 500 of an eye 200 of a patient. A coupling fluid or gel, for example a water column 2704, may be on or under the eye-contacting surface 104 in order to facilitate contact between the eye-contacting surface 104 and the surface 500 of the eye and/or in order to facilitate transmission of the shockwave from the shock-wave generator 2500 to the eye 200. The first and second electrodes 110, 112 may be co-axially aligned with one another such that a gap 114 is formed between the distal tips of the electrodes 110, 112. The shockwave generator 2500 may be configured to generate one or more shockwaves.

Figure 28:
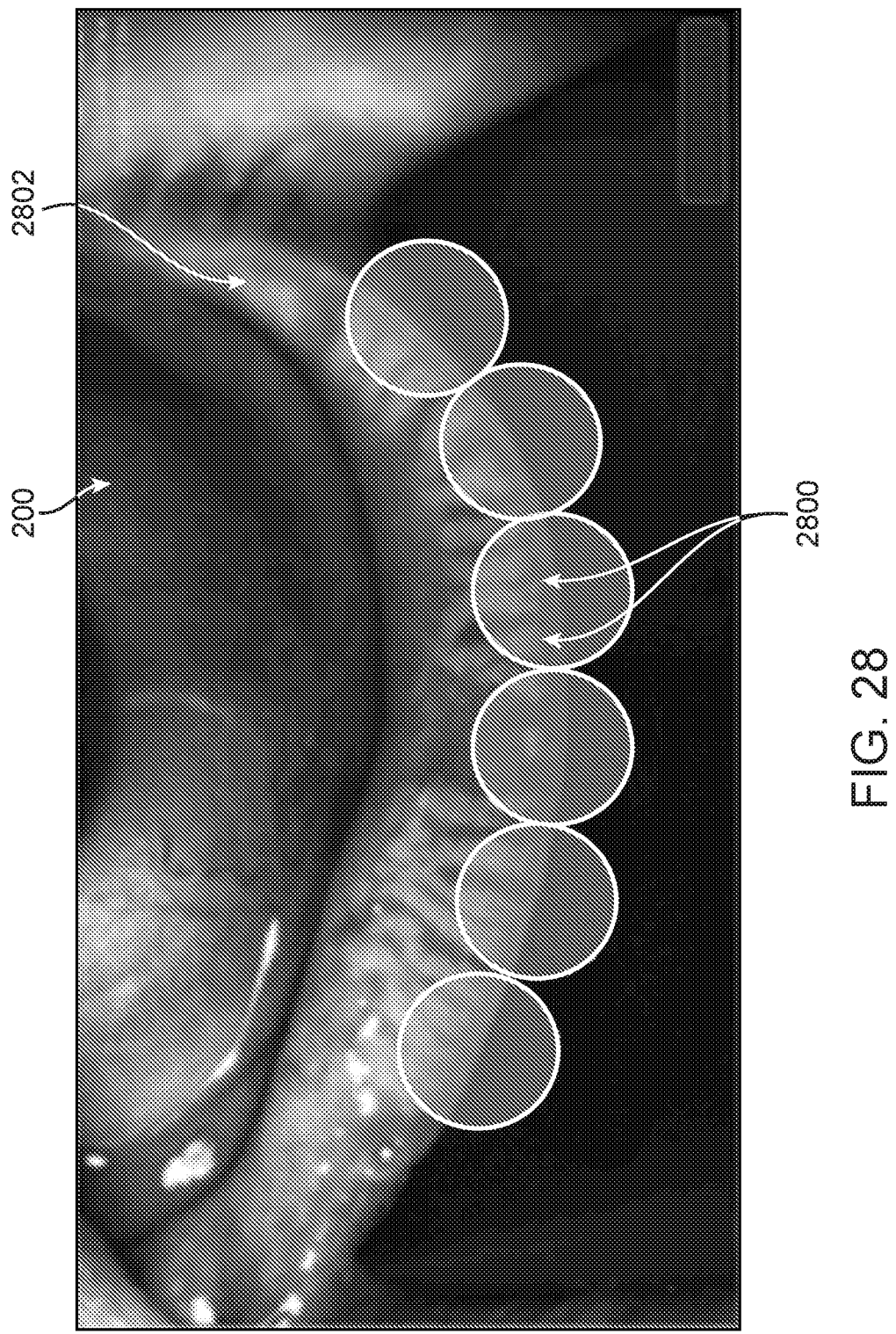
FIG. 28 shows an exemplary treatment pattern for dry eye disease, in accordance with embodiments.

FIG. 28 shows an exemplary treatment pattern for dry eye disease. In some patients, dry eye disease may be caused or exacerbated by meibomian gland dysfunction (MGD). Blockage of the meibomian glands 2800, which produce an oily substance that prevents evaporation of the eye's tear film layer called meibum, may lead to tear film evaporation and dry eyes. One or more shockwave generators, which may be substantially similar to any of the shockwave generators described herein, may be coupled to the eyelid 2802 adjacent the meibomian glands and low energy shock-waves may be directed to the meibomian glands 2800 in order to cause dilation thereof and facilitate meibum secre-tion therefrom. Alternatively, or in combination, one or more high energy shockwaves may be directed to obstructions in the meibomian glands in order to disaggregate or break up the blockage. In at least some instances, shockwave therapy may be more comfortable and/or more effective than current therapies for meibomian gland unblocking (which can include thermo-pulsing, punctal plugs, and medications).

Figure 29:
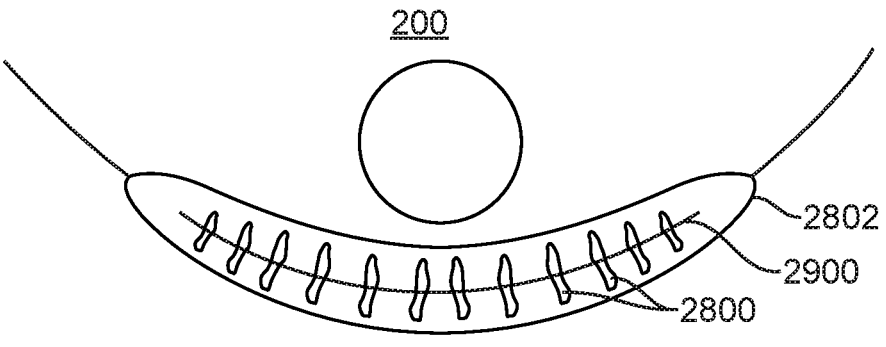
FIGS. 29-32 shows an exemplary treatment system for dry eye disease, in accordance with embodiments.
Figure 30:
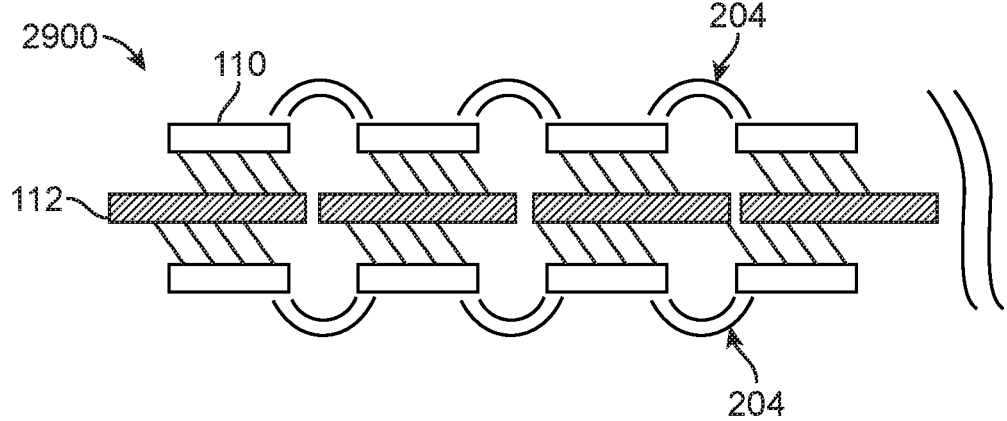
Figure 31:
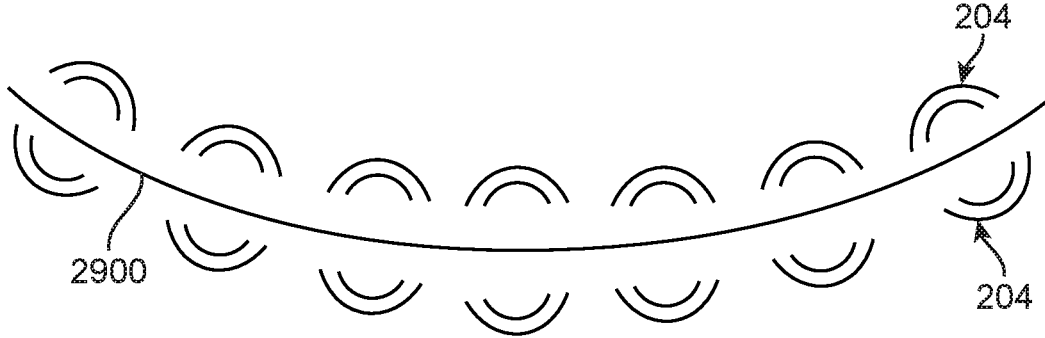
Figure 32:
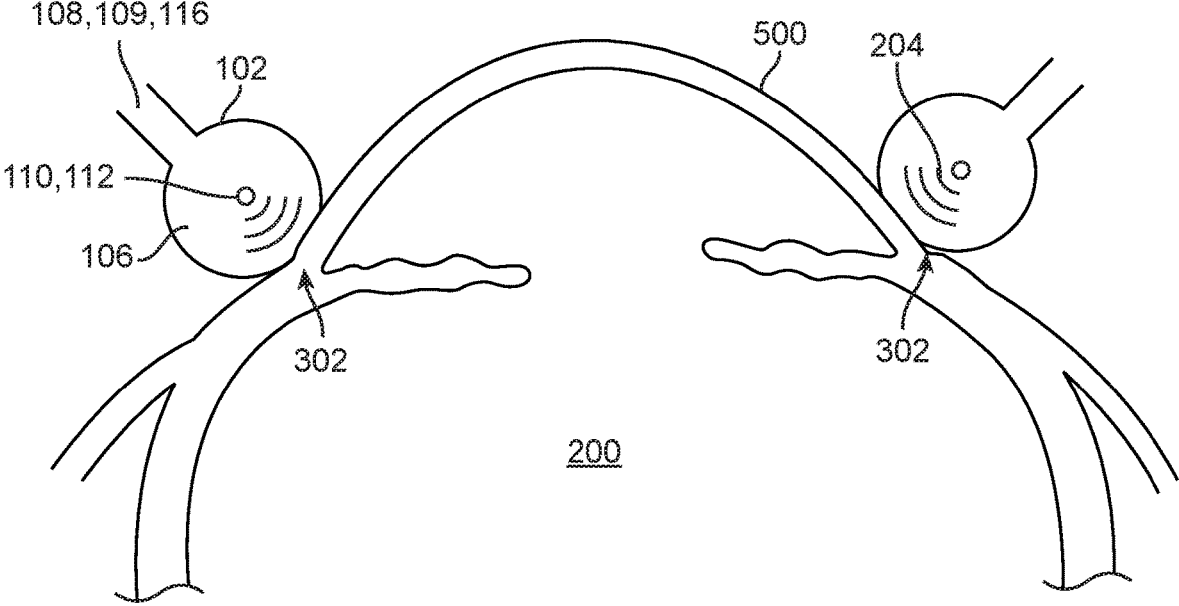

FIGS. 29-32 show an exemplary treatment system 2900 for dry eye disease. FIG. 29 shows an array 2900 of shockwave generators 100 positioned on an internal surface of an eyelid 2802 of an eye (i.e., palpebral placement) across a plurality of meibomian glands 2800. FIG. 30 shows an expanded view of an array 2900 of shockwave generators which may be used for treating meibomian glands 2800. The array 2900 of shockwave generators 100 may be substan-tially similar to any of the shockwave generators described herein. For example, the array 2900 of shockwave genera-tors 100 may comprise co-axial conductors 110, 112 exposed in fluid as described herein in order to maintain a low profile for patient comfort and ease of use. FIG. 31 shows a plurality of radially unfocused shockwaves 204 which may be generated by the shockwave generator array 2900 to treat the meibomian glands 2800. FIG. 32 shows a cross-sectional view of an eye 200 with the array 2900 of shockwave generators 100 placed in a ring around the limbus 302 in order to treat the meibomian glands 2800 of the eye 100 as described herein. The array 2900 of shockwave generators 100 may be disposed within a fluid-filled chamber 106 of a housing 102 having a fluid inlet 108 and a fluid outlet 109 as described herein.

Figure 33:
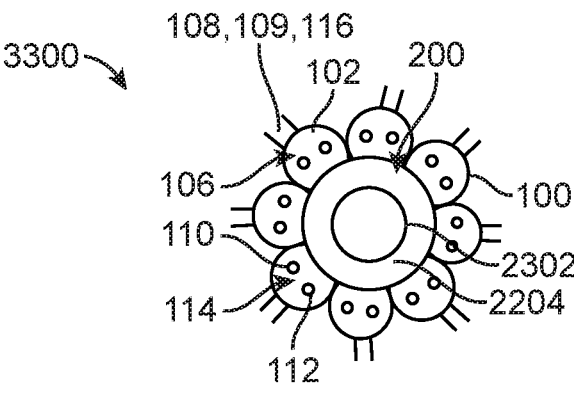
FIG. 33 shows a top view of an exemplary treatment system for lenticular softening, in accordance with embodiments.
Figure 34:
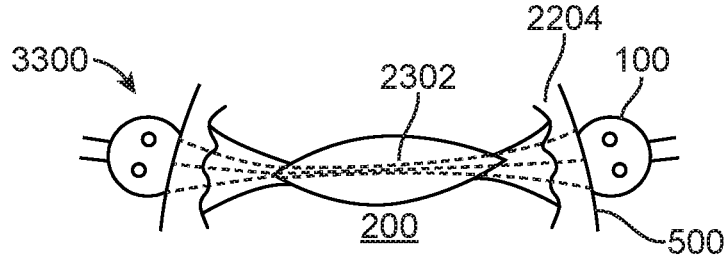
FIG. 34 shows a side cross-sectional view of the system of FIG. 33 disposed on an eye, in accordance with embodiments.

FIG. 33 shows a flattened top view of an exemplary treatment system 3300 for lenticular softening. FIG. 34 shows a side cross-sectional view of the system 3300 of FIG. 33 disposed on an eye. One or more shockwave generators, for example an annular array of shockwave generators 100, may be disposed on a surface 500 of an eye 200 as described herein. The shockwave generator(s) 100 may be substan-tially similar to any of the shockwave generators described herein. The shockwave generators 100 may be configured to target a lens 2302 (native or IOL) of the eye 200 in order soften the lens 2302 (e.g., to improve the accommodative amplitude of the eye). For example, a plurality of shockwave generators 100 may be placed above a sclera 2204 of the eye and the shockwaves may be focused towards the lens 2302 in order to cause lenticular dis-agglomeration and softening and initiate LEC apoptosis.

Figure 35:
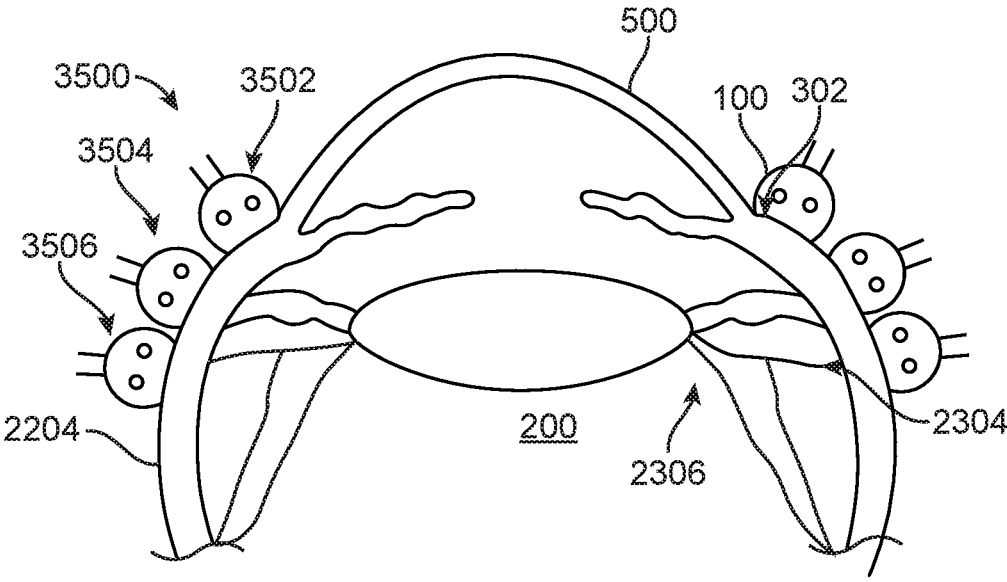
FIG. 35 shows a side cross-sectional view of an exemplary treatment system for presbyopia, in accordance with embodiments.

FIG. 35 shows a side cross-sectional view of an exem-plary treatment system 3500 for presbyopia. One or more shockwave generators, for example an array of shockwave generators 100, may be disposed on a surface 500 of an eye 200 as described herein. The shockwave generator(s) 100 may be substantially similar to any of the shockwave generators described herein. The shockwave generators 100 may be configured to target one or more tissue locations in the eye 200 in order improve the accommodative amplitude of the eye. For example, a plurality of shockwave generators 100 may be placed above a sclera 2204 of the eye and the shockwaves may be focused towards the IVZ 2304 and/or PVZ 2306 in order to cause disaggreration thereof and improve movement thereof. For example, a first annular row of shockwave generators may be configured to focus shock-waves towards the IVZ 2034 and a second annular row of shockwave generators, disposed radially outward from the first annular row, may be configured to focus shockwaves towards the PVZ 2306. Alternatively, or in combination, a plurality of shockwave generators 3506 may be placed above the pars plana and the shockwaves may be focused to the sclera 2204 in order to generate microporation therein and enhance compliance and anterior and centripetal motion of the ciliary apex thereof.

Figures 36, 37:
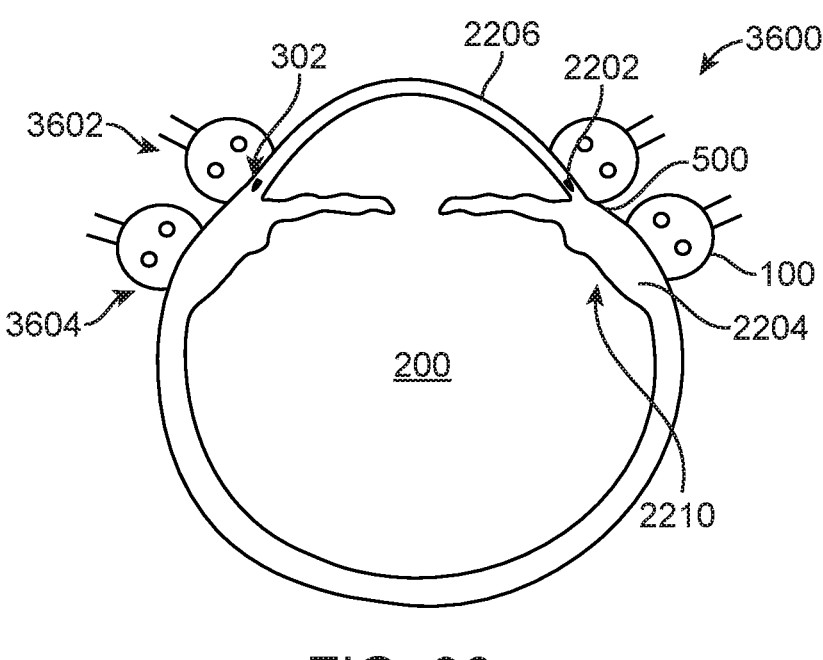
FIG. 36 shows a side cross-sectional view of an exemplary treatment system for glaucoma, in accordance with embodiments.
FIG. 37 shows a top view of the system of FIG. 36, in accordance with embodiments.

FIG. 36 shows a side cross-sectional view of an exem-plary treatment system 3600 for glaucoma. FIG. 37 shows a top view of the system of FIG. 36. One or more shockwave generators, for example an array of shockwave generators 100, may be disposed on a surface 500 of an eye 200 as described herein. The shockwave generator(s) 100 may be substantially similar to any of the shockwave generators described herein. The shockwave generators 100 may be configured to target one or more tissue locations in the eye 200 in order to reduce IOP. For example, a plurality of shockwave generators 100 may be placed above the limbus 302 of the eye 200 as described herein and the shockwaves may be focused towards the trabecular meshwork and/or Schlemm's canal 2202 in order to cause dilation thereof and improve fluid outflow from the eye. The shockwave gen-erators disposed over the limbus 302 may be configured as a first annular row 3602 of shockwave generators. Alterna-tively, or in combination, a plurality of shockwave genera-tors 100 may be placed above the pars plana as described herein and the shockwaves may be focused to the sclera 2204 and/or the ciliary body 2210 in order to generate microporation therein and enhance uveoscleral outflow. The shockwave generators 100 disposed over the pars plana may be configured as a second annular row 3604 of shockwave generators disposed radially outward from the first annular row.

Figure 38:
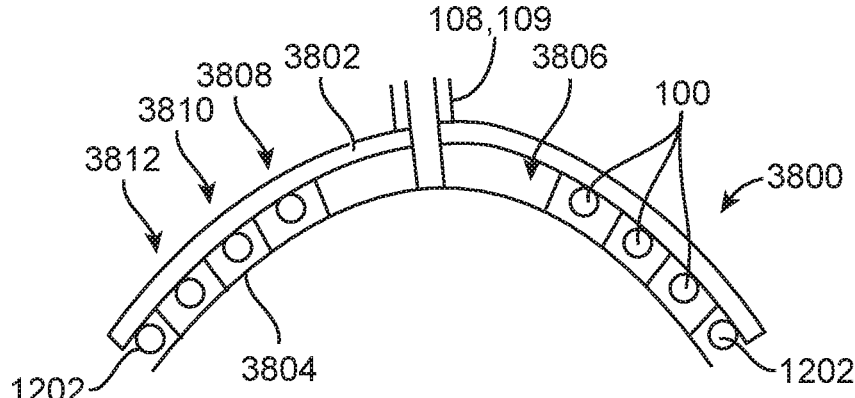
FIG. 38 shows a side cross-sectional view of an exemplary array of shockwave generators, in accordance with embodiments.
Figure 39:
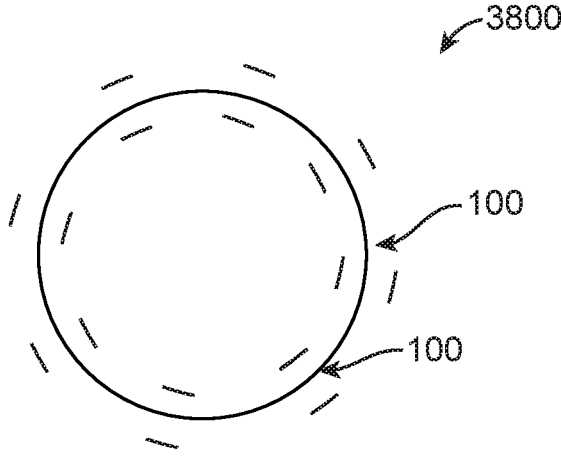
FIG. 39 shows a top view of the array of FIG. 38, in accordance with embodiments.

FIG. 38 shows a side cross-sectional view of an exemplary array 3800 of shockwave generators 100. FIG. 39 shows a top view of the array of FIG. 38. The system 3800 may comprise one or more shockwave generators 100, which may be substantially similar to any of the shockwave generators described herein. For example, the shockwave generators 100 may comprise a pair of electrodes or an optical fiber as described herein. The shockwave generators 100 may be disposed under a contact lens 3082. The contact lens 3802 may be substantially similar to any of the contact lenses described herein. A film 3804 may be disposed across the bottom of the contact lens 3802 in order to form a fluid-filled chamber 3806 around the shockwave generators. The film 2804 may comprise an eye-contacting surface configured to be coupled to a surface of the eye, which may be substantially similar to any of the eye-contacting surfaces described herein. The fluid-filled chamber 3806 may be filled with saline and/or graphene as described herein. In some embodiments, the shockwave generator array 3800 may further comprise a fluid inlet 108 and a fluid outlet 109 in fluid communication with the fluid-filled chamber 3806 as described herein.

In some embodiments, the contact lens 3802 may be configured to act as a reflector in order to focus the shockwaves towards a desired pre-determined location. For example, an inner surface of the contact lens may comprise one or more ellipsoidal shapes or structures embedded therein. Alternatively, or in combination, one or more reflectors may be coupled to an internal surface of the fluid-filled chamber in order to focus the shockwaves. An inner wall of the fluid filled chamber 3806 or a reflector coupled to an internal surface of the fluid-filled chamber 3806 may be ellipsoidal in shape.

In some embodiments, the contact lens 3802 may comprise a thickness of about 2.0 mm, 1.5 mm, 1.0 mm, or 0.5 mm.

In some embodiments, the outer housing of the contact lens 3802 may sit about 1.5 mm above the surface of the eye when the film is disposed thereon.

In some embodiments, the system 3800 may comprise an array of shockwave generators 100. For example, the system may comprise eight shockwave generators disposed every 45 degrees along an annular pattern over the surface of the eye as shown in FIG. 39. For example, an annular pattern having a diameter of 11 mm may have each shockwave generator spaced 4 mm from its closest neighbors.

In some embodiments, the system 3800 may comprise an array comprising a plurality of shockwave annular rings as described herein. In some embodiments, when treating glaucoma, a first ring 3808 may have a diameter of about 11 mm so as to be positioned above a limbus of the eye when the contact lens is disposed thereon, a second ring 3810 may have a diameter of about 14 mm, and a third ring 3812 may have a diameter of about 17 mm. In some embodiments, when treating presbyopia, the pars plana and structures adjacent thereto may be treated with a first ring 3808 having a diameter of about 13 mm, a second ring 3810 having a diameter of about 16 mm, and a third ring 3812 having a diameter of about 19 mm. In some embodiments, the lens may be targeted with a first ring 3808 having a diameter of about 3 mm, a second ring 3810 having a diameter of about 6 mm, and a third ring 3812 having a diameter of about 9 mm.

In some embodiments, the system 3800 may be securely coupled to the eye with suction (e.g., with suction rings 1202) on the inner and outer edges of the annular contact lens 3802.

Figure 40:
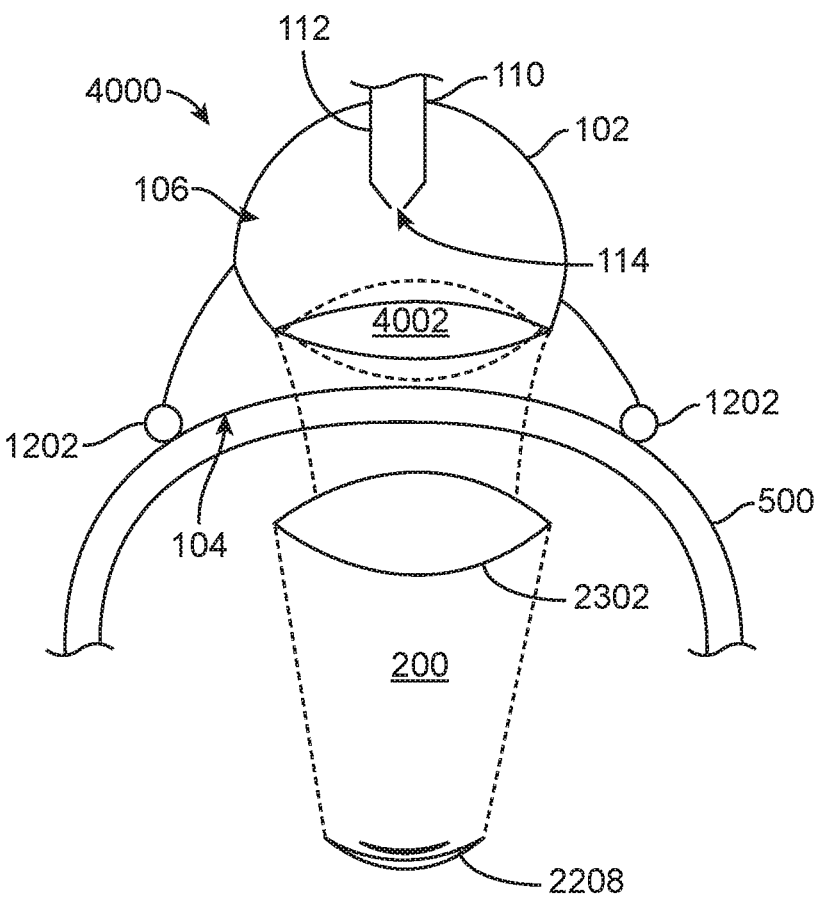
FIG. 40 shows a side cross-sectional view of an exemplary treatment system for AMD, in accordance with embodiments.

FIG. 40 shows a side cross-sectional view of an exemplary treatment system for AMD. The system may comprise a large diameter shockwave generator 4000 configured to deliver shockwaves onto the retina 2208. The shockwave generator 4000 may be substantially similar to any of the shockwave generators described herein. For example, the shockwave generator 4000 may comprise a first electrode 110 and a second electrode 112 disposed within housing 102. The housing 102 may comprise a fluid-filled chamber 106 and an eye-contacting surface 104. The fluid-filled chamber 106 may be configured to act as a reflector in order to focus the shockwaves towards a desired pre-determined location. Alternatively, or in combination, one or more reflectors may be coupled to an internal surface of the fluid-filled chamber 106 in order to focus the shockwaves. The one or more reflectors may, for example, comprise an electronically variable acoustic lens 4002, which may enable variable focusing of the shockwaves on the macular of the retina 2208. An inner wall of the fluid filled chamber 106 may be ellipsoidal in shape. The conjugate foci of the ellipse may be configured such that the shockwaves are focused through the crystalline lens 2302 of the eye, which then refracts the shockwaves onto the retina 2208 of the eye. The eye-contacting surface 104 may be configured to be coupled to a surface 500 of an eye of a patient. A coupling fluid or gel, for example a water column, may be on or under the eye-contacting surface in order to facilitate contact between the eye-contacting surface 104 and the surface 500 of the eye and/or in order to facilitate transmission of the shockwave from the shockwave generator to the eye. A suction ring 1202 may be disposed on an outer edge of the shockwave generator 4000 in order to couple the shockwave generator 4000 to a cornea or sclera of the eye. The first and second electrodes 110, 112 may be co-axially aligned with one another such that a gap 114 is formed between the distal tips of the electrodes 110, 112. The shockwave generator 4000 may be configured to generate one or more shockwaves.

Figure 41:
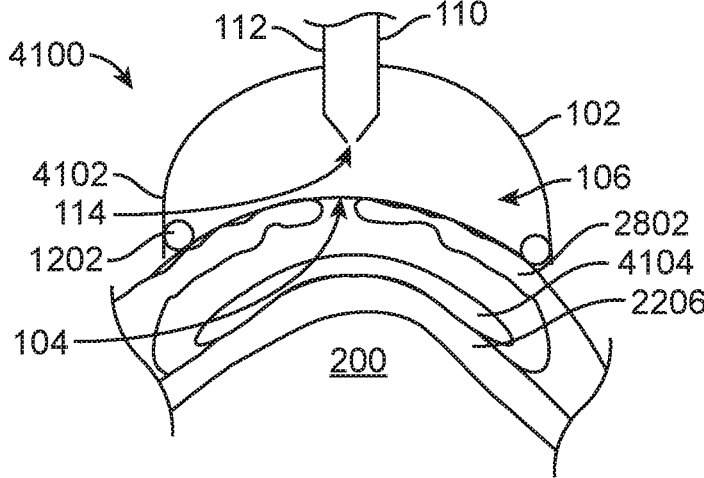
FIG. 41 shows a side cross-sectional view of an exemplary treatment system for dry eye disease, in accordance with embodiments.

FIG. 41 shows a side cross-sectional view of an exemplary treatment system 4100 for dry eye disease. The system 4100 may comprise a large diameter shockwave generator 4102 configured to deliver shockwaves onto a heat spreading contact lens 4104 disposed on a cornea 2206 of the eye. The shockwave generator 4102 may be substantially similar to any of the shockwave generators described herein. For example, the shockwave generator 4102 may comprise a first electrode 110 and a second electrode 112 disposed within housing 102. The housing 102 may comprise a fluid-filled chamber 106 and an eye-contacting surface 104. The fluid-filled chamber 106 may be configured to act as a reflector in order to focus the shockwaves towards a desired pre-determined location. Alternatively, or in combination, one or more reflectors may be coupled to an internal surface of the fluid-filled chamber 106 in order to focus the shockwaves. An inner wall of the fluid filled chamber 106 or a reflector coupled to an internal surface of the fluid-filled chamber 106 may be ellipsoidal in shape. The eye-contacting surface 104 may be configured to be coupled to an eyelid 2802 of a patient (e.g., when the patient's eye is closed). A heat spreading contact lens 4104 may be disposed on the cornea 2206 of the patient under the eyelid 2802 in order to facilitate transmission of the shockwave from the shockwave generator to the eye 200. The heat spreading contact lens 4104 may be configured to act as an acoustic reflector and direct the shockwaves towards one or more meibomian glands in order to treat dry eye as described herein. A suction ring 1202 may be disposed on an outer edge of the shockwave generator 4102 in order to couple the shockwave generator 4102 to the eyelids 2802. The first and second electrodes 110, 112 may be co-axially aligned with one another such that a gap 114 is formed between the distal tips of the electrodes 110, 112. The shockwave generator 4102 may be configured to generate one or more shockwaves.

Figure 42:
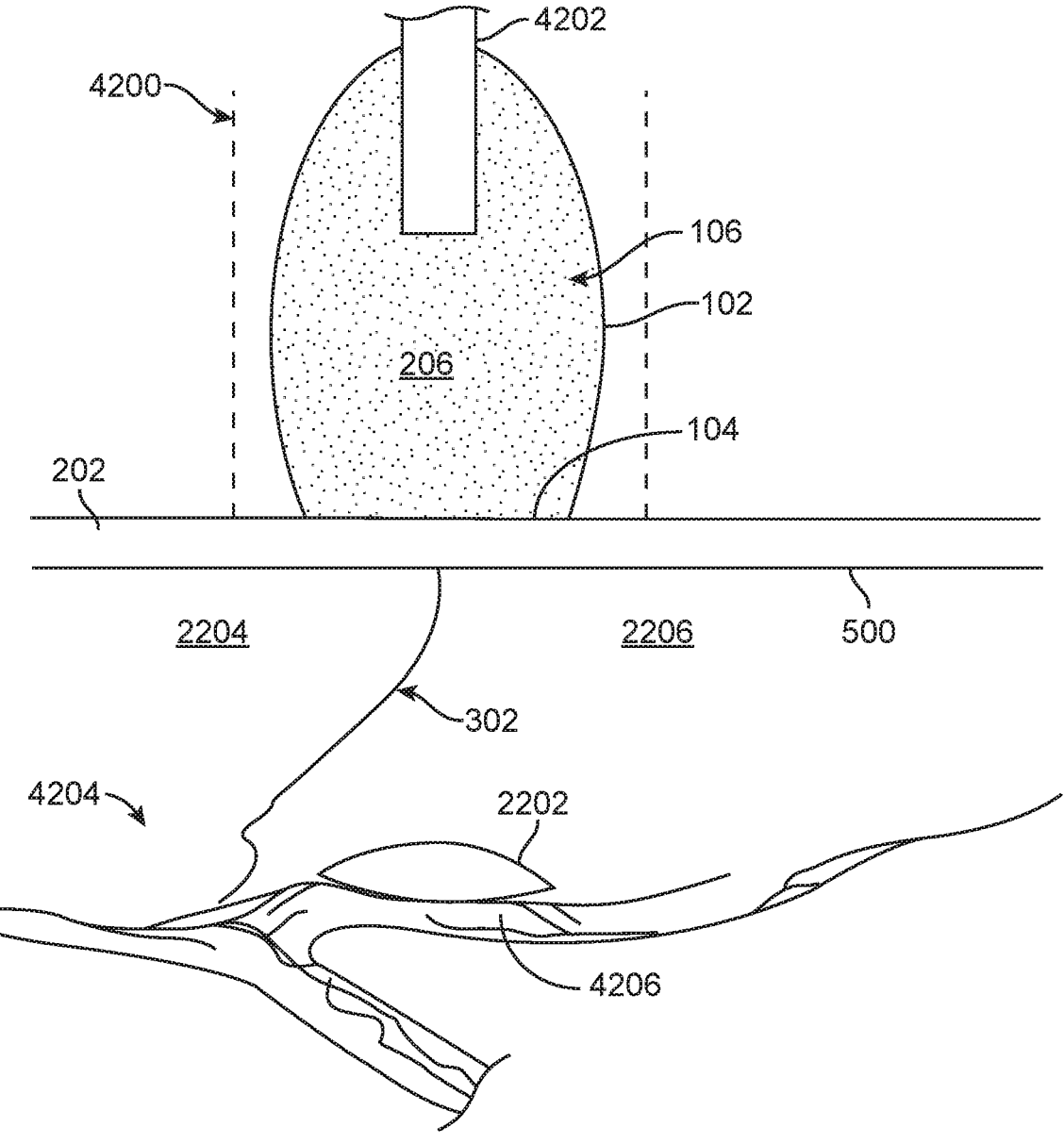
FIG. 42 shows a cross-sectional view of an exemplary laser-based shockwave generator, in accordance with embodiments.

FIG. 42 shows a cross-sectional view of an exemplary laser-based shockwave generator 4200. The shockwave generator 4200 may comprise a fiber optic cable 4202 disposed within a housing 102. The housing 102 may comprise a fluid-filled chamber 106 and an eye-contacting surface 104 as described herein. The eye-contacting surface 104 may be configured to be coupled to a surface 500 of an eye of a patient as described herein. The optical fiber 4202 may be configured to generate one or more shockwaves in a fluid 206 of the fluid-filled chamber 106 when optical energy is emitted therefrom. A laser, for example a pulsed laser, may be coupled to the optical fiber 4202 in order to provide optical energy thereto. The shockwave generator system may comprise one or more sensors as described herein.

The shockwave generator 4200 may be configured to generate one or more shockwaves with the optical fiber 4202. The shockwave generator 4200 may be configured to treat one or more tissues or structures on or below the surface 500 of the eye with the shockwaves it generates. Treatment may be non-thermal. The shockwaves may be focused to a pre-determined location or unfocused as described herein. Shockwaves may be used to locally fractionate, microporate, dilate, and/or sensolyse desired ocular tissues. In some embodiments, shockwaves may be used to produce biomechanical effects (such as vasodilation, microporation, softening, etc.) and/or or biochemical effects (such as neovascularlization, etc.) as described herein. In some embodiments, shockwaves may be used for drug delivery to ocular tissues.

The fluid-filled chamber 106 may comprise a fluid 206 disposed therein. The fluid may comprise a conductive (e.g., about 0.6 mS conductivity), biocompatible liquid. The fluid may comprise water or saline. The fluid may comprise a suspension of graphene in saline. In some embodiments, the fluid may comprise a suspension of graphene in saline which may be sufficiently light-absorbing so as to prevent or reduce light from being emitted by the shockwave generator 4200. The fluid may be chilled (e.g., about 10 degrees C.). In some embodiments, the shockwave generator 4200 may further comprise a fluid inlet and a fluid outlet in fluid communication with the fluid-filled chamber 106. The fluid 206 may be used to couple the shockwave generated by the fiber 4202 to the surface 500 of the eye. The fluid may be circulated within the fluid-filled chamber 106 via the fluid inlet and the fluid outlet. Fluid circulation may enable continuous extraction of thermal buildup, cavitation bubbles, and ions generated during shockwave formation as pulsed delivery of the shockwaves is ongoing. In some embodiments, the fluid 206 flowing out of the fluid-filled chamber 106 via the fluid outlet may be sampled periodically or continuously as described herein.

The fluid-filled chamber 106 may be configured to act as a reflector in order to focus the shockwaves towards a desired pre-determined location. Alternatively, or in combination, one or more reflectors, which may be substantially similar to any of the reflectors described herein, may be coupled to an internal surface of the fluid-filled chamber in order to focus the shockwaves. An inner wall of the fluid filled chamber 106 or a reflector coupled to an internal surface of the fluid-filled chamber 106 may be ellipsoidal in shape as described herein.

In some embodiments, the optical fiber 4202 may be configured to emit a collimated beam of optical energy into the fluid of the fluid-filled chamber 106.

The optical fiber 4202 may be coupled to an optical energy source, for example a laser. The laser may comprise a pulsed laser. The laser may be configured to emit light of a high water-absorbing wavelength. For example, the laser may be configured to emit light in the mid-infrared range of wavelengths, for example, 1.44 µm, 1.475 µm, 1.55 µm, 1.948 µm, or 6 µm. The laser may, for example, comprise a Nd:Yag or Th:Ho laser, or the like.

In some embodiments, optical energy pulses from a pulsed laser may be about 1 Hz to about 25 Hz.

In some embodiments, optical energy pulses from a pulsed laser may be about on the order of nanoseconds to microseconds in length.

In some embodiments, the laser may be a free space scanning laser or fiber-coupled delivery may be utilized depending on access to the target tissue. For example, a scanning laser may be cone-coupled to an eye. The cone may position the scanning laser at a known working distance above the eye. A saline-filled contact lens balloon may be disposed over the eye within the cone. The outer housing of the contact lens balloon may be transparent to the laser light (e.g., infrared-transparent when using an infrared laser). The laser may be scanned over the contact lens balloon and shockwaves may be generated in a substantially similar manner as described herein when the laser light reaches the fluid of the contact lens balloon.

In some embodiments, the shockwave generator may be disposed on a distal end of a handheld probe.

In some embodiments, the laser-based shockwave generator 4200 may be disposed adjacent the limbus 302 and configured to focus shockwaves to the trabecular meshwork 4206 and Schlemm's canal 2202 and/or to open the iridocorneal angle 4204 for treatment of glaucoma.

Figure 43:
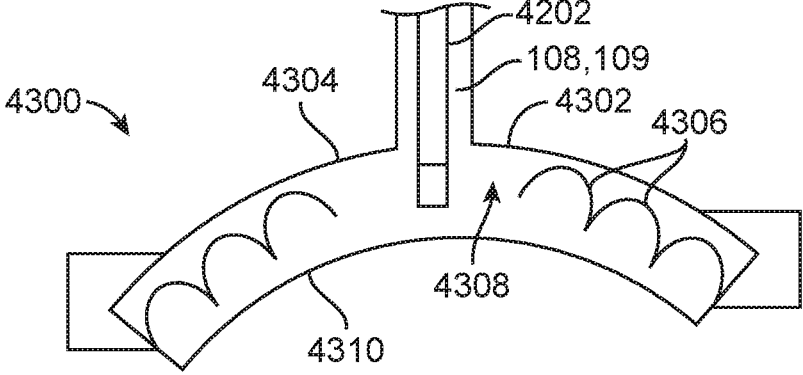
FIG. 43 shows a side cross-sectional view of an array of laser-based shockwave generators in a fluid-filled contact lens balloon, in accordance with embodiments.

FIG. 43 shows a side cross-sectional view of an array 4300 of laser-based shockwave generators 4200 in a fluid-filled contact lens 4302. The fluid-filled contact lens balloon 4302 may be substantially similar to any of the contact lenses described herein. For example, the contact balloon 4302 may comprise an inflatable outer housing 4304 with a plurality of ellipsoidal reflectors 4306 embedded therein. The outer housing 4304 may define an inner chamber 4308 which may be filled with a fluid such as saline or saline with graphene in order to inflate the outer housing 4304 prior to, during, or after placement of the contact balloon 4302 on a surface of the eye (e.g., adjacent the limbus, sclera, eyelids, etc. as described herein). One or more optical fibers 4202 may be disposed within the fluid-filled chamber 4308 and configured to generate a shockwave therefrom as described herein. The ellipsoidal reflectors 4306 embedded along the inner surface of the fluid-filled chamber 4308 may be configured to help focus the shockwave towards a pre-determined location on or under the surface of the eye as described herein. In some embodiments, the reflectors 4306 may be arranged in a plurality of annular rows as described herein in order to target multiple locations of the eye. For example, a first row of reflectors may be disposed adjacent the limbus and configured to focus shockwaves to the trabecular meshwork and Schlemm's canal. A second row of reflectors may be disposed radially outward therefrom adjacent the pars plicata and a third row of shockwave generators may be radially outward from the second row adjacent the pars plana. The second and/or third row of reflectors may be configured to focus shockwaves to the sclera, the pars plicata, the pars plana, the ciliary body, the IVZs, and/or the PVZs, for example. One or more suction rings may be disposed along one or more edges of the contact lens balloon 4302 in order to secure the contact lens balloon to the surface of the eye as described herein.

In some embodiments, the fluid filling the inner chamber 4308 of the contact balloon 4302 may be a chilled or temperature controlled-liquid.

The outer housing 4304 may comprise a compliant material. Alternatively, or in combination, at least a portion of the outer housing 4304 may comprise a non-compliant material. In some embodiments, the outer housing may comprise polymethylmethacrylate (PMMA).

In some embodiments, a coupling fluid or gel 202 may be on the eye-contacting surface 4310 of the outer housing 4304 in order to facilitate contact between the eye-contacting surface 4310 and the surface of the eye and/or in order to facilitate transmission of the shockwave from the shockwave generator/reflector to the eye.

In some embodiments, an imaging device, for example a camera, OCT, or wavefront device, may be disposed within the contact lens (e.g., in a cornea centric location) in order to facilitate intraoperative precision of pressure wave delivery as described herein.

Figures 44, 45, 46:
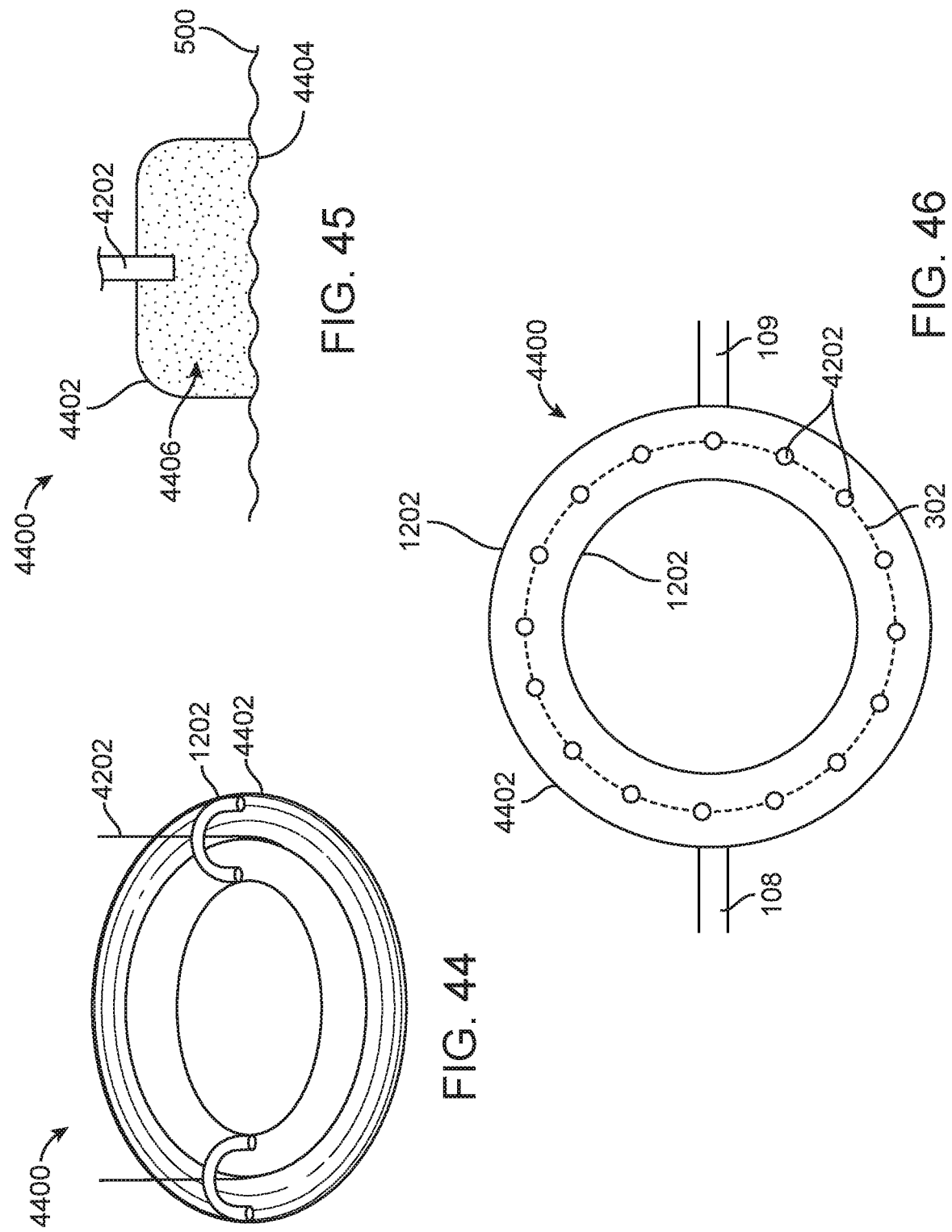
FIG. 44 shows a perspective view of an array of laser-based shockwave generators in an annular fluid-filled contact lens, in accordance with embodiments.
FIG. 45 shows a side cross-sectional view of the system of FIG. 44, in accordance with embodiments.
FIG. 46 shows a top view of the system of FIG. 44, in accordance with embodiments.

FIG. 44 shows a perspective view of an array 4400 of laser-based shockwave generators 4200 in an annular fluid-filled contact lens 4402. FIG. 45 shows a side cross-sectional view of the system 4400 of FIG. 44. FIG. 46 shows a top view of the system 4400 of FIG. 44. The system 4400 may comprise one or more shockwave generators 4200, which may be substantially similar to any of the shockwave generators described herein. For example, the shockwave generators 4200 may comprise on or more optical fibers 4202 as described herein. The shockwave generators 4200 may be disposed under a contact lens or within a contact lens balloon 4402 as described herein. A film 4404 may be disposed across the bottom of the contact lens 4402 in order to form a fluid-filled chamber 4406 around the shockwave generators 4200. The film 4404 may comprise an eye-contacting surface configured to be coupled to a surface 500 of the eye, which may be substantially similar to any of the eye-contacting surfaces described herein. The fluid-filled chamber 4406 may be filled with saline and graphene as described herein. In some embodiments, the system 4400 may further comprise a fluid inlet 108 and a fluid outlet 109 in fluid communication with the fluid-filled chamber 4406 as described herein.

In some embodiments, the contact lens 4402 may be configured to act as a reflector in order to focus the shockwaves towards a desired pre-determined location. For example, an inner surface of the contact lens may comprise one or more ellipsoidal shapes or structures embedded therein. Alternatively, or in combination, one or more reflectors may be coupled to an internal surface of the fluid-filled chamber in order to focus the shockwaves. An inner wall of the fluid filled chamber or a reflector coupled to an internal surface of the fluid-filled chamber may be ellipsoidal in shape.

In some embodiments, the distal end of the optical fiber 4202 may sit about 1.5 mm above the surface of the eye when the film 4404 is disposed thereon.

In some embodiments, the system 4400 may comprise an array of shockwave generators 4200. For example, the system 4400 may comprise a plurality of shockwave generators 4200 disposed in an annular pattern. A plurality of optical fibers 4202 may be coupled to the contact lens 4402 and disposed within the fluid-filled chamber 4406 in order to generate a plurality of shockwaves as described herein.

In some embodiments, the system 4400 may be securely coupled to the eye with suction (e.g., with suction rings 1202) on the inner and outer edges of the annular contact lens 4402.

Figure 47:
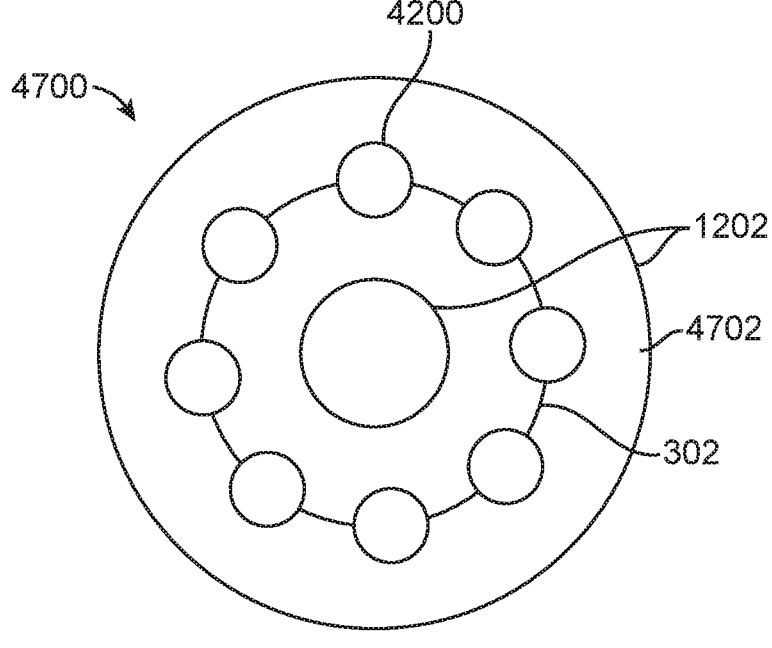
FIG. 47 shows a top view of an array of laser-based shockwave generators in an annular fluid-filled contact lens, in accordance with embodiments.
Figure 48:
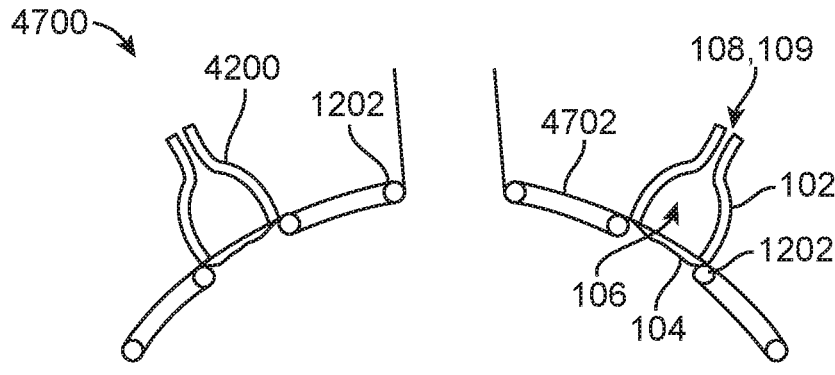
FIG. 48 shows a side cross-sectional view of the system of FIG. 47, in accordance with embodiments.

FIG. 47 shows a top view of an array 4700 of laser-based shockwave generators 4200 in an annular contact lens 4702. FIG. 48 shows a side cross-sectional view of the system 4700 of FIG. 47. A plurality of shockwave generators 4200, which may be substantially similar to any of the shockwave generators described herein, may be disposed within a contact lens 4702. For example, the plurality of shockwave generators 4200 may comprise a housing 102 and an eye-contacting surface 104 defining a fluid-filled chamber 106 therewithin. The housing 102 may be coupled to or comprise a structure disposed within an annular contact lens 4702. For example, the housing 102 may comprise a 3-D printed material and may be surround by contact lens material such as PMMA in order to form an annular contact lens structure 4702 surrounding the shockwave generators 4200. The annular contact lens 4702 may be securely coupled to the eye with suction (e.g., with suction rings 1202) on the inner and outer edges thereof. The plurality of shockwave generators 4200 may comprise a pair of electrodes or an optical fiber configured to generate shockwave(s) within the fluid-filled chamber as described herein. The shockwaves may be focused to one or more locations on or below the surface of the eye as described herein.

In some embodiments, the annular contact lens 4702 may comprise a plurality of shockwave generators, for example 8 or 16 shockwave generators disposed at a limbal diameter of about 11 mm.

In some embodiments, the diameter of each shockwave generator 4200 may be about 3 mm.

In some embodiments, the outer diameter of the annular contact lens 4702 may be about 19 mm.

Figure 49:
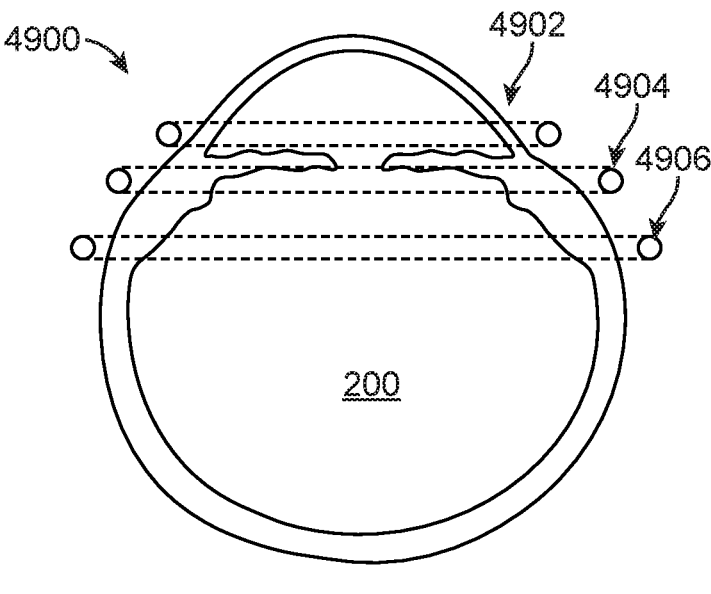
FIG. 49 shows a side cross-sectional view of an array of shockwave generators arranged in multiple rows and disposed on an eye, in accordance with embodiments.
Figure 50:
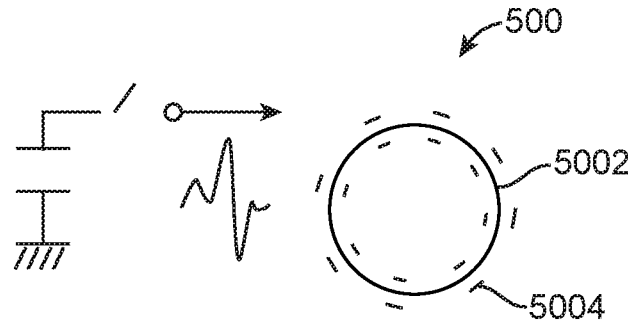
FIG. 50 shows an exemplary row of shockwave generators comprising a conductive wire disposed within an insulated sheath having a plurality of apertures therein, in accordance with embodiments.
Figure 51:
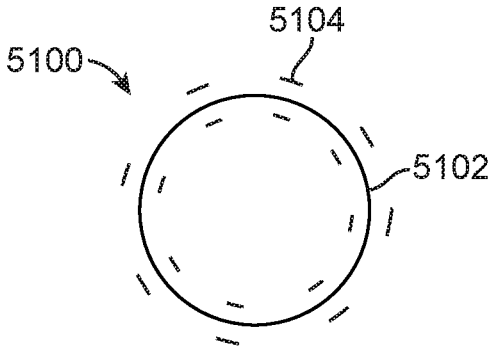
FIG. 51 shows an exemplary row of shockwave generators comprising an optical fiber disposed within a cladding having a plurality of apertures therein, in accordance with embodiments.
Figures 52, 53:
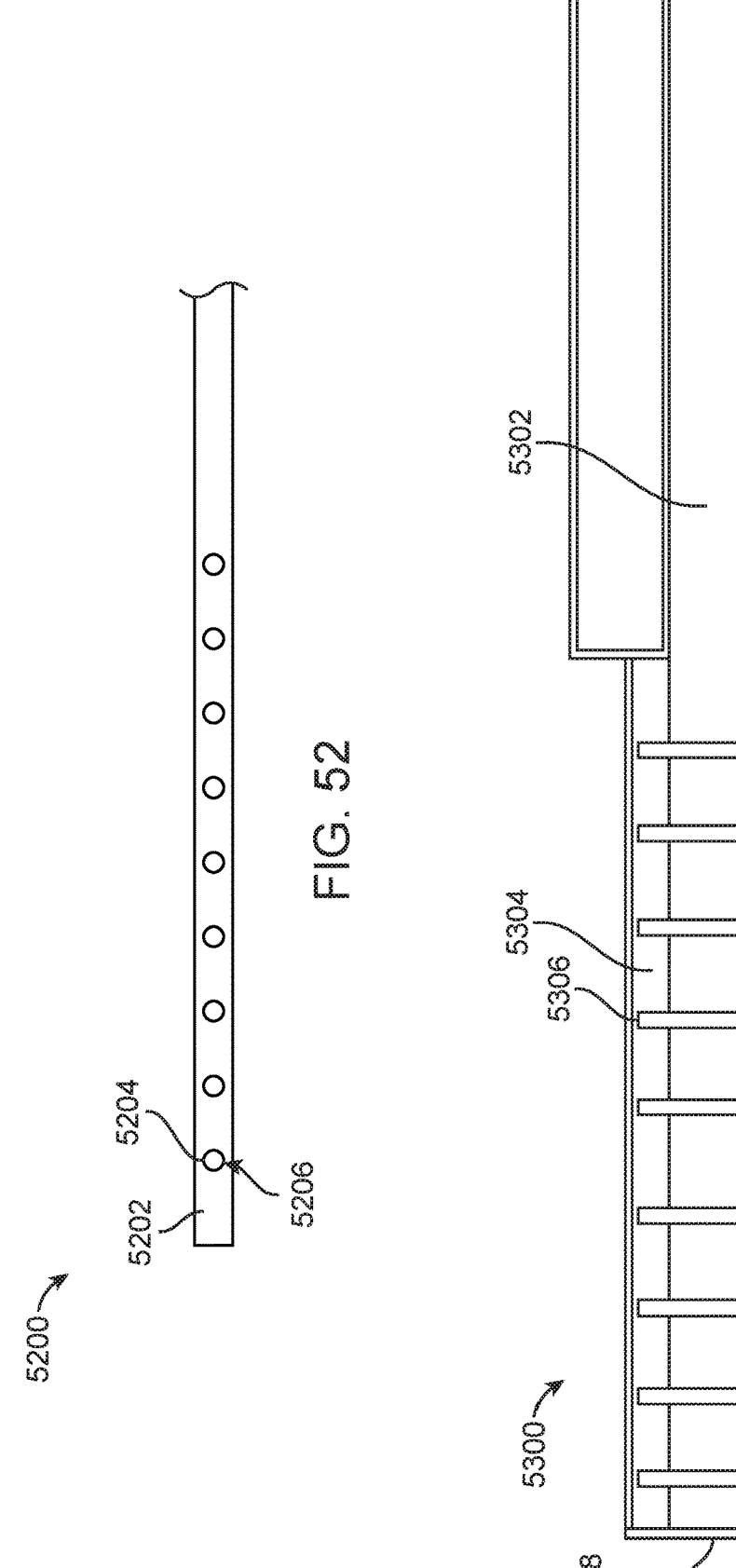
FIG. 52 shows an exploded view of an array of electrode-based shockwave generators comprising a conductive wire disposed within an insulated sheath having a plurality of apertures therein, in accordance with embodiments.
FIG. 53 shows an exploded view of an array of laser-based shockwave generators comprising an optical fiber disposed within a cladding having a plurality of apertures therein, in accordance with embodiments.

FIG. 49 shows a side cross-sectional view of an array 4900 of shockwave generators arranged in multiple rows and disposed on an eye. The array of shockwave generators may comprise a conductive wire disposed within an insulated sheath having a plurality of apertures therein (e.g., as shown in FIGS. 50 and 52) or an optical fiber disposed within a cladding having a plurality of apertures therein (e.g., as shown in FIGS. 51 and 53). One or more shockwave-generating wires or fibers may be disposed within a fluid-filled contact lens as described herein. The portion of the one or more shockwave-generating wires or fibers disposed adjacent the eye may be annularly shaped as described herein. In some embodiments, the fluid-filled contact lens may comprise three annular shockwave-generating wires or fibers disposed within a fluid-filled chamber thereof. For example, a first wire or fiber 4902 may be disposed within the contact lens above the limbus, a second wire or fiber 4904 may be disposed within the contact lens above the pars plicata, and a third wire or fiber 4906 may be disposed within the contact lens above the pars plana as described herein.

The apertures of the shockwave-generating wire or fiber may be configured to direct shockwaves to one or more locations on or below a surface of the eye as described herein.

The contact lens may comprise one or more reflecting surface (e.g., an inner ellipsoidal wall of the fluid-filled chamber and/or a reflector) as described herein in order to facilitate focusing of the shockwaves.

In some embodiments, the apertures may be disposed about 1 mm above the surface of the eye within the contact lens.

Suction may be used to secure the contact lens on the eye. For example, a first suction ring may be disposed at an inner edge (e.g., about 9 mm) and a second suction ring may be disposed at an outer edge (e.g., about 19 mm) of the annular contact lens.

Fluid may be circulated within the fluid-filled chamber as described herein.

FIG. 50 shows an exemplary row 5000 of shockwave generators comprising a conductive wire 5002 disposed within an insulated sheath having a plurality of apertures 5004 therein. A conductive wire may be disposed within an insulated sheath or coating configured to prevent electrical energy emission therethrough. The conductive wire may be disposed adjacent an eye, for example within a low-profile fluid-filled contact lens coupled to a surface of the eye as described herein. The fluid-filled contact lens may be configured to focus the shockwaves generated by the conductive wire to one or more pre-determined locations on or below a surface of the eye. The conductive wire may be disposed in an annular ring within the fluid-filled contact lens. In some embodiments, the fluid-filled contact lens may comprise a plurality of annular wires disposed therein at multiple radial diameters as described herein. One or more holes or apertures may be made within the insulation at predetermined locations in order to enable the conductive wire to act as an electrode and generate a shockwave when energized as described herein. For example, eight side-firing apertures may be disposed within the cladding in order to form eight shockwave generators along the length of the wire. A single wire may be used to transmit energy from the electrical arcs of aperture-exposed electrodes into the surrounding fluid, which may then generate shockwaves as described herein.

It will be understood by one of ordinary skill in the art that the number of side-firing apertures disposed within the insulation may be any number desired based on the treatment location(s) and pattern(s) of interest.

In some embodiments, the conductive wire or cable may have an outer diameter of about 100 μm.

FIG. 51 shows an exemplary row 5100 of shockwave generators comprising an optical fiber 5102 disposed within a cladding having a plurality of apertures 5104 therein. An optical fiber may be disposed within a cladding configured to prevent light emission therethrough. The optical fiber may be disposed adjacent an eye, for example embedded within a fluid-filled annular (e.g., scleral) contact lens coupled to a surface of the eye as described herein. The fluid-filled contact lens may be configured to focus the shockwaves generated by the optical fiber to one or more pre-determined locations on or below a surface of the eye. The optical fiber may be disposed in an annular ring within the fluid-filled contact lens. One or more holes or apertures (i.e., selective uncladding) may be made within the cladding at predetermined locations in order to enable the optical fiber to emit light therethrough. For example, nine side-firing apertures may be disposed within the cladding in order to form nine shockwave generators along the length of the fiber. Because a single optical fiber is used to transmit optical energy into the surrounding fluid through the apertures, which may then generate shockwaves as described herein, the power output of the shockwaves generated at each aperture may be the same. The shockwaves may be generated simultaneously at each of the apertures. A mirror may be disposed on a distal end of the optical fiber.

It will be understood by one of ordinary skill in the art that the number of side-firing apertures disposed within the cladding may be any number desired based on the treatment location(s) and pattern(s) of interest.

In some embodiments, the optical fiber may comprise a polymicro 50 μm core with a 30 μm cladding therearound (for an outer diameter of 80 μm).

In some embodiments, the optical fiber may comprise an outer diameter of about 100 μm.

FIG. 52 shows an exploded view of an array 5200 of shockwave generators comprising a conductive wire 5206 disposed within an insulated sheath 5202 having a plurality of apertures 5204 therein. A conductive wire 5206 may be disposed within an insulated sheath or coating 5202 config-ured to prevent electrical energy emission therethrough. The conductive wire 5206 may be disposed adjacent an eye, for example within a fluid-filled contact lens coupled to a surface of the eye as described herein. The fluid-filled contact lens may be configured to focus the shockwaves generated by the conductive wire to one or more pre-determined locations on or below a surface of the eye. The conductive wire 5206 may be disposed in an annular ring within the fluid-filled contact lens. In some embodiments, the fluid-filled contact lens may comprise a plurality of annular wires disposed therein at multiple radial diameters as described herein. One or more holes or apertures 5204 may be made within the insulation 5202 at predetermined locations in order to enable the conductive wire 5206 to act as an electrode and generate a shockwave when energized as described herein. For example, nine side-firing apertures 5204 may be disposed within the cladding 5202 in order to form nine shockwave generators along the length of the wire. A single wire 5206 may be used to transmit energy from the electrical arcs of aperture-exposed electrodes into the surrounding fluid, which may then generate shockwaves as described herein. The shockwaves may be generated simultaneously at each of the apertures 5204.

In some embodiments, the apertures 5204 may be equally spaced along the length of conductive wire 5206 adjacent the eye. For example, each of the nine apertures 5204 may be spaced 4 mm apart from their immediate neighbors. In some embodiments, the apertures 5204 may not be equally spaced along the length of wire 5206 adjacent the eye.

It will be understood by one of ordinary skill in the art that the number of side-firing apertures 5204 disposed within the insulation 5202 may be any number desired based on the treatment location(s) and pattern(s) of interest.

In some embodiments, the insulation 5202 may comprise a polyamide insulation.

In some embodiments, the apertures 5204 may be about 0.5 mm in diameter.

FIG. 53 shows an exploded view of array 5300 of shockwave generators comprising an optical fiber 5302 disposed within a cladding 5304 having a plurality of apertures 5306 therein. An optical fiber 5302 may be dis-posed within a cladding 5304 configured to prevent light emission therethrough. The optical fiber 5302 may be dis-posed adjacent an eye, for example within a fluid-filled contact lens coupled to a surface of the eye as described herein. The fluid-filled contact lens may be configured to focus the shockwaves generated by the optical fiber to one or more pre-determined locations on or below a surface of the eye. The optical fiber 5302 may be disposed in an annular ring within the fluid-filled contact lens. One or more holes or apertures 5306 (i.e., selective uncladding) may be made within the cladding 5304 at predetermined locations in order to enable the optical fiber 5302 to emit light therethrough. For example, nine side-firing apertures 5306 may be disposed within the cladding 5304 in order to form nine shockwave generators along the length of the fiber 5302. Because a single optical fiber 5302 is used to transmit optical energy into the surrounding fluid through the apertures 5306, which may then generate shockwaves as described herein, the power output of the shockwaves generated at each aperture 5306 may be the same. A mirror 5308 may be disposed on a distal end of the optical fiber 5302.

In some embodiments, the apertures 5306 may be equally spaced along the length of optical fiber 5302 adjacent the eye. For example, each of the nine apertures 5306 may be spaced 4 mm apart from their immediate neighbors. In some embodiments, the apertures 5306 may not be equally spaced along the length of optical fiber adjacent the eye.

It will be understood by one of ordinary skill in the art that the number of side-firing apertures 5306 disposed within the cladding may be any number desired based on the treatment location(s) and pattern(s) of interest.

In some embodiments, the optical fiber 5302 may comprise a polymicro 50 μm core with a 30 μm cladding therearound (for an outer diameter of 80 μm).

Figure 54:
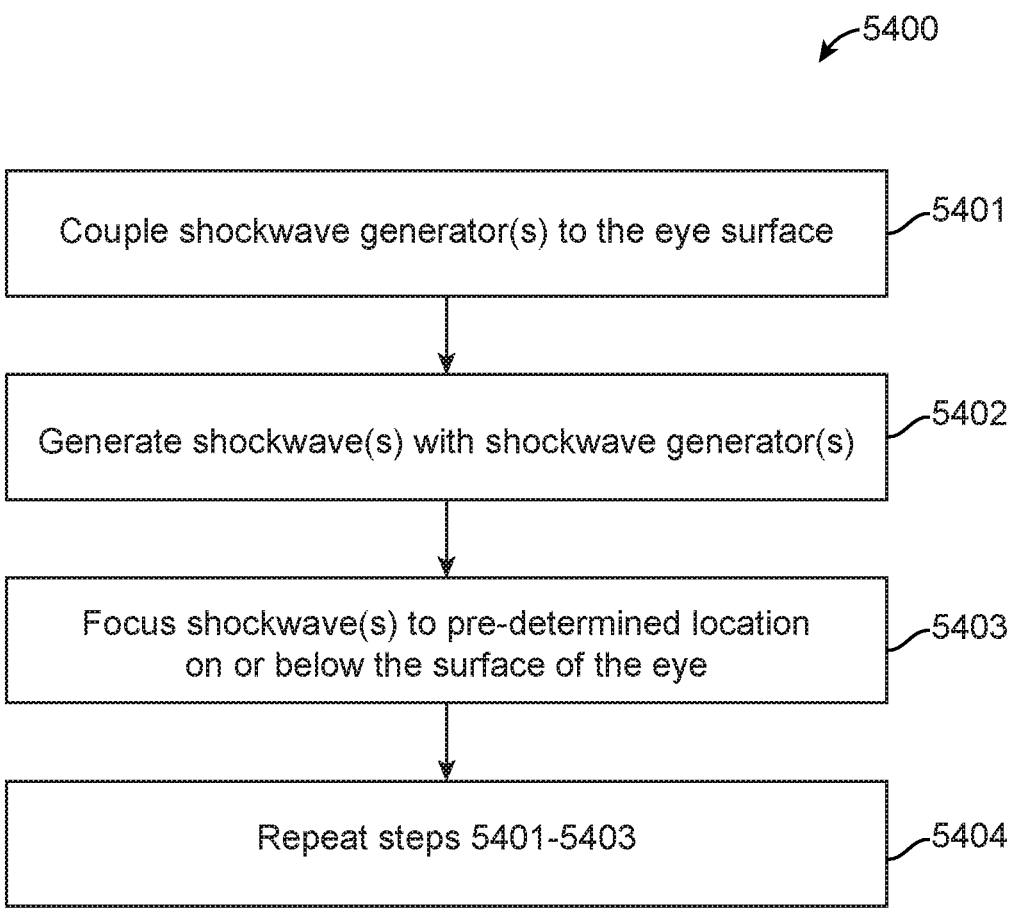
FIG. 54 shows a method for treating an eye, in accordance with embodiments.

FIG. 54 shows a method 5400 for treating an eye.

At step 5401, one or more shockwave generators may be coupled to a surface of the eye. The shockwave generator(s) may comprise any of the shockwave generators described herein. For example, a single shockwave generator may be coupled to the eye as described herein. Alternatively, an array of shockwave generators may be coupled to the eye as described herein, such as with a contact lens or contact balloon, or the like.

At step 5402, one or more of the shockwave generator(s) may be energized to generate one or more shockwaves as described herein. When more than one shockwave generator is used, the shockwave generators may be energized independently of one another (e.g., in sequence) or in concert with one or more other shockwave generators (e.g., at least two simultaneously firing generators). It will be understood by one of ordinary skill in the art any combination of shockwave generators may be energized at one or independently of one another.

At step 5403, the shockwave(s) may be focused to a pre-determined location(s) on or below the surface of the eye. It will be understood by one of ordinary skill in the art the pre-determined location may be chosen based on the opthalmic condition or conditions to be treated. For example, when treating a glaucomatous eye, the pre-determined location may comprise the trabecular meshwork, Schlemm's canal, the sclera, and/or the retina. In a presbyopic eye, the pre-determined location may comprise the sclera, IVZ, PVZ, and/or lens. In an eye with AMD, the pre-determined location may comprise the pan-macular retina, for example a fovea or a perifovea of the retina. In an eye with dry eye disease, the pre-determined location may comprise a meibomian gland. It will be understood by one of ordinary skill in the art that multiple conditions may be treated in the same eye and the pre-determined locations treated in the eye may correspond to the conditions to be treated. For example, an eye being treated for both glaucoma and presbyopia may have the shockwaves focused to sclera in order to generate microporation therein, which may improve fluid outflow (and subsequently reduce IOP for glaucoma treatment) and scleral compliance (which may improve its range of motion during accommodation).

At step 5404, steps 5401-5403 may be repeated, as needed, to treat the eye for the condition of interest.

While the shockwave generators described herein generally rely on electrohydraulic shockwave generation, it will be understood by one of ordinary skill in the art based on the teachings herein that other shockwave generation methods may be utilized, including piezo-electric, laser, magneto-electric shockwave generator(s) as described herein. For example, a moving coil or permanent magnet coupled to the eye may also serve as a shockwave generator.

The shockwave therapy methods described herein may be enhanced with the application on nanoparticles. The nanoparticles may mediate shockwave initiation at lower cavitation thresholds than without nanoparticles. Acoustically-sensitive nanoparticles may be added to the fluid of the fluid-filled chamber of any of the shockwave generators described herein in order to reduce the threshold for cavitation bubble and shockwave formation. In some embodiments, the tissue being targeted for treatment can be infused (e.g., pre-operatively) with nanoparticles in order to enhance extravasation and/or penetration of the nanoparticles. Alternatively, or in combination, pre-infusion of the nanoparticles into the tissue may accelerate and/or prolong inertial cavitation and/or reduce associated side effects.

Without being limited by any particular theory, nanoparticle mediated acoustic cavitation may lead to cytotoxic effects via one or both of two main pathways hypothesized in the art—1. collapsing bubbles directly damage cells through shock waves, shear stresses, and formation of reactive oxygen species, and/or 2. Caviation-induced nanoparticle activation (depending on the nanoparticle formulation and desired effects) can lead to chemical cytotoxicity.

In some embodiments, the nanoparticles may comprise nanodroplets, nanocones, polymer cupes, or the like. For example, the nanoparticles may comprise perfluorohexane nanocones, mesoporous silica nanoparticles, solid gas trapping nanoparticles, microbubbles, acoustically-vaporizable droplets, polymercups, or the like.

In any of the embodiments described herein, the housing and/or one or more reflectors coupled to an inner surface of the housing may comprise plastic or metal. In at least some instances, a metal housing or reflector may reflect the shockwaves more efficiently than a plastic housing or reflector due to the lower acoustic impedance of metal compared to plastic. This may reduce the input power required to generate the shockwaves.

In some embodiments, an array of shockwave generators may comprise a plurality of electrodes shaped like a wheel and spokes such that each electrode is electrically coupled to every other electrode and can be driven by the same power source and fired at the same time. The plurality of electrodes may be formed from a metal foil (e.g., brass, stainless steel, or the like).

Figure 55:
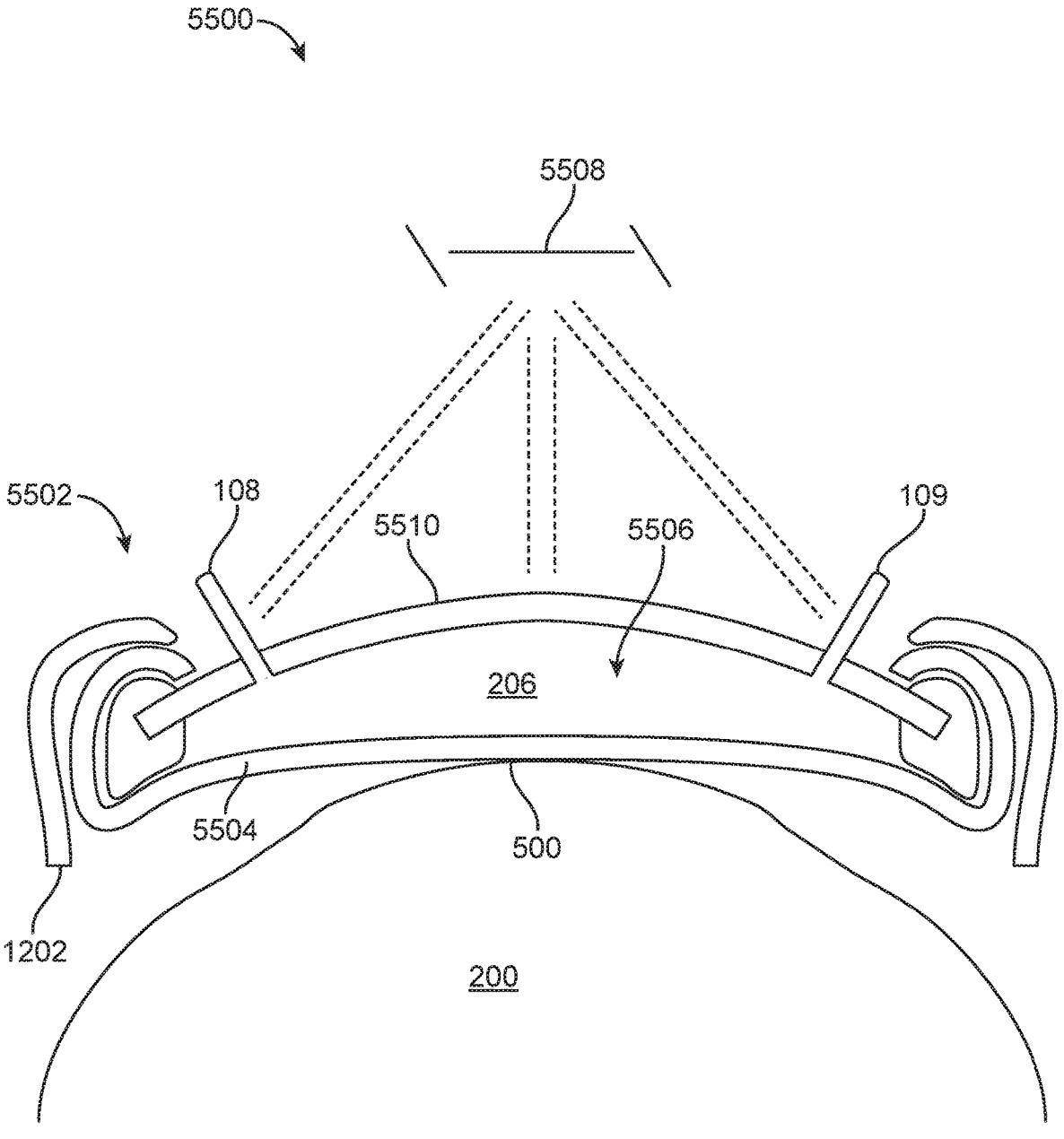
FIG. 55 shows a side cross-sectional view of an exemplary laser scanning shockwave generator system comprising a contact lens coupled to an eye, in accordance with embodiments.

FIG. 55 shows a side cross-sectional view of an exemplary laser scanning shockwave generator system 5500 comprising a contact lens 5502 coupled to a surface 500 of an eye 200. The contact lens 5502 may be substantially similar to any of the fluid-filled contact lenses described herein. The contact lens may comprise a film or membrane 5504 disposed across the bottom of the contact lens 5502 in order to form a fluid-filled chamber 5506 therebetween. The film 5504 may comprise an eye-contacting surface configured to be coupled to a surface of the eye, which may be substantially similar to any of the eye-contacting surfaces described herein. The fluid-filled chamber 5506 may be filled with a fluid, such as saline, as described herein. The fluid 206 may comprise a suspension of graphene in saline. In some embodiments, the fluid 206 may comprise a suspension of graphene in saline which may be sufficiently light-absorbing so as to prevent or reduce light from being emitted by the scanning laser 5508. In some embodiments, the contact lens 5502 may further comprise a fluid inlet 108 and a fluid outlet 109 in fluid communication with the fluid-filled chamber 106 as described herein. The fluid 206 may be circulated within the fluid-filled chamber 5506 via the fluid inlet 108 and the fluid outlet 109. The anterior surface 5510 of the contact lens may comprise a transparent meniscus window through which optical energy can pass. For example, the transparent meniscus window 5510 may be transparent to laser light (e.g., infrared-transparent when using an infrared laser). The system 5500 may further comprise a free space scanning laser 5508. The scanning laser 5508 may be a pulsed laser. In some embodiments, the scanning laser 5508 may be cone-coupled to the eye. The cone may position the scanning laser 5508 at a known working distance above the eye. The contact lens 5502 may be disposed over the eye within the cone. The laser 5508 may be scanned over the contact lens balloon 5502 and shockwaves may be generated in a substantially similar manner as described herein when the laser light reaches the fluid of the contact lens. The use of a scanning laser 5508 may provide for increased spatio-temporal flexibility in treatment location compared to a fixed shockwave generator.

In some embodiments, the system 5500 may be securely coupled to the eye with suction (e.g., with suction rings 1202) on the outer edges of the contact lens.

In some embodiments, the film 5504 may comprise a PET and/or PTFE membrane as described herein. The film 5504 may comprise any of the materials described herein.

The laser 5508 may be configured to emit light of a high water-absorbing wavelength. For example, the laser may be configured to emit light in the mid-infrared range of wavelengths, for example, 1.44 μm, 1.475 μm, 1.55 μm, 1.948 μm, 3 μm, or 6 μm. The laser may, for example, comprise a Nd:Yag or Th:Ho laser, or the like. In some embodiments, the laser may be configured to emit light in the near-infrared range of wavelengths. In some embodiments, the laser may be configured to emit light in the long-infrared range of wavelengths, for example 10 μm. In some embodiments, the laser may be configured to emit light in the far infrared range of wavelengths, for example at a frequency on the order of a few tetrahertz (THz).

In some embodiments, optical energy pulses from a pulsed laser may be about 1 Hz to about 25 Hz.

In some embodiments, optical energy pulses from a pulsed laser may be about on the order of nanoseconds to microseconds in length.

Figure 56:
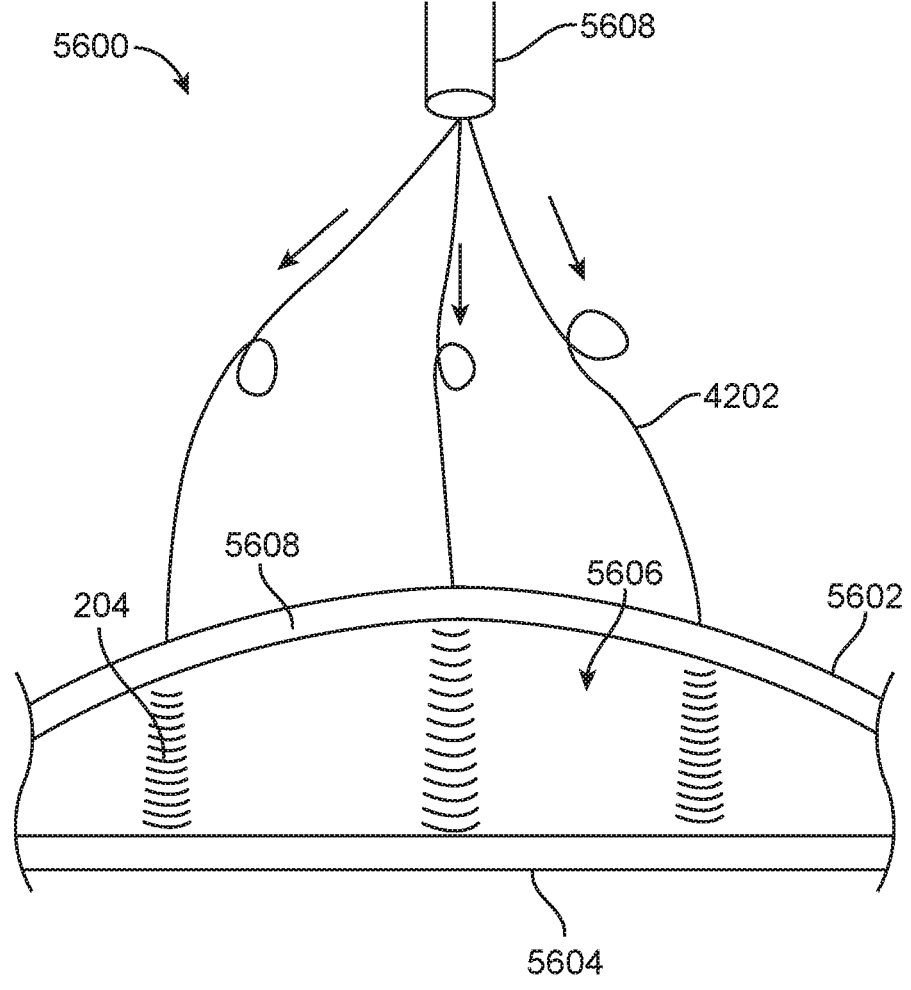
FIG. 56 shows a side cross-sectional view of an exemplary multi-fiber laser-based shockwave generator array system comprising a contact lens, in accordance with embodiments.

FIG. 56 shows a side cross-sectional view of an exemplary multi-fiber laser-based shockwave generator array system 5600 comprising a contact lens 5602. The contact lens 5602 may be substantially similar to any of the fluid-filled contact lenses described herein. The contact lens 5602 may comprise a film or membrane 5604 disposed across the bottom of the contact lens 5602 in order to form a fluid-filled chamber 5606 therebetween. The film 5604 may comprise an eye-contacting surface configured to be coupled to a surface of the eye, which may be substantially similar to any of the eye-contacting surfaces described herein. The fluid-filled chamber 5606 may be filled with a fluid, such as saline, as described herein. The fluid may comprise a suspension of graphene in saline. In some embodiments, the fluid may comprise a suspension of graphene in saline which may be sufficiently light-absorbing so as to prevent or reduce light from being emitted by the scanning laser. In some embodiments, the contact lens 5602 may further comprise a fluid inlet and a fluid outlet in fluid communication with the fluid-filled chamber 5606 as described herein. The fluid may be circulated within the fluid-filled chamber 5606 via the fluid inlet and the fluid outlet. The system 5600 may further comprise a one or more fiber optic cables 4202 coupled to the contact lens. The one or more optical fibers 4202 may be configured to generate one or more shockwaves in a fluid of the fluid-filled chamber 5606 when optical energy is emitted therefrom. Shockwaves may be generated in a substantially similar manner as described herein when the laser light reaches the fluid of the contact lens balloon 5602.

A laser, for example a pulsed laser, may be coupled to the optical fiber 4202 in order to provide optical energy thereto. In some embodiments, the one or more optical fibers 4202 may comprise a fiber bundle or multi-fiber array 5608. Two or more optical fibers 4202 may be bundled in fiber bundle 5608 which may split into an array of fibers 4202 adjacent the contact lens 5602, which may then be individually coupled to the contact lens 5602 at pre-determined locations as described herein.

In some embodiments, the anterior surface 5608 of the contact lens 5602 may comprise a transparent meniscus window through which optical energy can pass as described herein. The fibers 4202 may be coupled to the anterior surface 5608 of the contact lens 5602 such that optical energy passes from the fibers 4202, through the anterior surface 5608 of the contact lens 5602, and into the fluid of the contact lens. Alternatively, or in combination, the fibers 4202 may pass through the anterior surface 5608 of the contact less 5602 such that optical energy passes directly from the fibers 4202 into the fluid of the contact lens.

In some embodiments, the contact lens 5602 may be configured to act as a reflector (or a reflector array) in order to focus the shockwaves towards a desired pre-determined location(s). Alternatively, or in combination, one or more reflectors may be coupled to an internal surface of the fluid-filled chamber 5606 in order to focus the shockwaves.

In some embodiments, the optical fiber 4202 may be configured to emit a collimated beam of optical energy into the fluid of the fluid-filled chamber.

Figure 57:
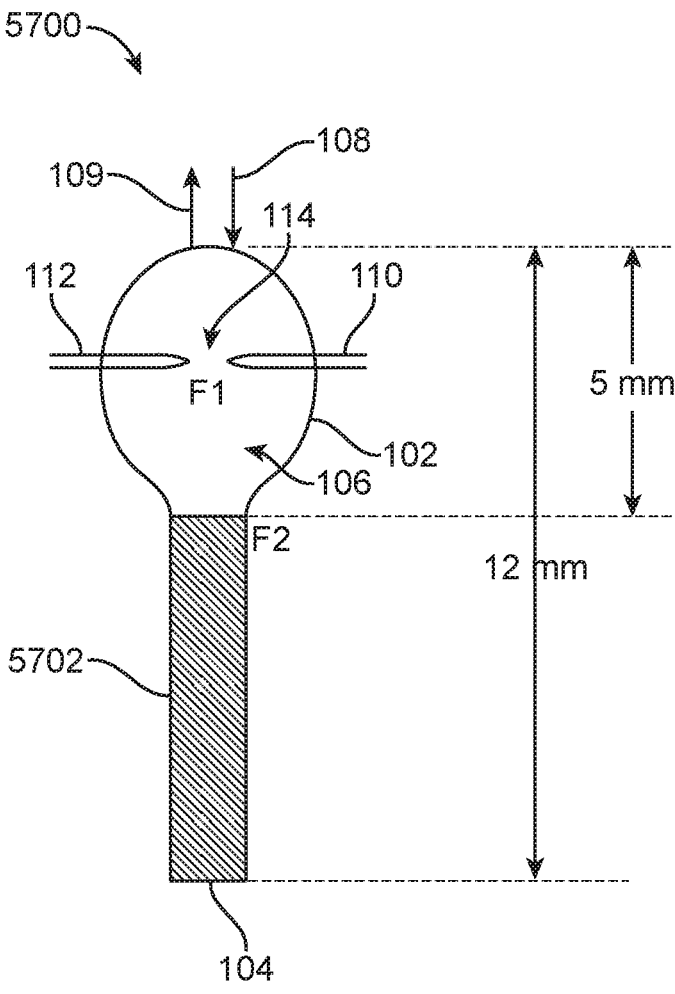
FIG. 57 shows a side cross-sectional view of an exemplary shockwave wave guide, in accordance with embodiments.

FIG. 57 shows a side cross-sectional view of an exemplary shockwave generator 5700 comprising a wave guide 5702. The shockwave generator 5700 may be substantially similar to any of the shockwave generators described herein. For example, the shockwave generator 5700 may comprise a first electrode 110 and a second electrode 112 disposed within a housing 102. The housing may comprise a fluid-filled chamber 106 and an eye-contacting surface 104. In some embodiments, the shockwave generator 5700 may further comprise a fluid inlet 108 and a fluid outlet 109 in fluid communication with the fluid-filled chamber 106 as described herein. The fluid may be circulated within the fluid-filled chamber 106 via the fluid inlet 108 and the fluid outlet 109. In some embodiments, the shockwave generating component (e.g., electrodes, laser fiber, etc.) and the fluid-filled chamber 106 may be spaced away from the eye-contacting surface 104 by a wave guide 5702. The wave guide 5702 may be disposed between the fluid-filled chamber 106 and the eye-contacting surface 104. The fluid-filled chamber 106 may be configured to act as a reflector in order to focus the shockwaves towards a desired pre-determined location via the wave guide 5702. Alternatively, or in combination, one or more reflectors may be coupled to an internal surface of the fluid-filled chamber 106 in order to focus the shockwaves. An inner wall of the fluid filled chamber 106 may be ellipsoidal in shape. Alternatively, or in combination, an end of the wave guide 5702 comprising the eye-contacting surface 104 may be configured to focus the shockwaves to a predetermined location on or below the surface of the eye. The eye-contacting surface 104 may be configured to be coupled to a surface of an eye of a patient. A coupling fluid or gel, for example a water column, may be on or under the eye-contacting surface in order to facilitate contact between the eye-contacting surface and the surface of the eye and/or in order to facilitate transmission of the shockwave from the shockwave generator to the eye as described herein. The first and second electrodes 110, 112 may be co-axially aligned with one another such that a gap 114 is formed between the distal tips of the electrodes 110, 112. The shockwave generator 5700 may be configured to generate one or more shockwaves. The wave guide 5702 may be configured to transmit the shockwaves from the fluid-filled chamber 106 of the shockwave generator to the eye-contacting surface 104.

In some embodiments, the wave guide 5702 may improve safety of the shockwave system by increasing the spacing between the fluidtronics of the shockwave generator 5700 and the plane of the eye contacting surface 104. The wave guide 5702 may also provide increased fluid volume and length for fluid circulation and bubble removal. In some embodiments, the wave guide 5702 may have a length within a range of about 1 cm to about 2 cm. In some embodiments, the wave guide 5702 may be about 12 mm or more in length. For example, the wave guide 5702 may have a length within a range of about 12 mm to about 80 mm.

In some embodiments, the wave guide may reduce the need to minimize system components in order to compact them into a space directly adjacent the eye (such as within a contact lens balloon or the like).

In some embodiments, the shockwave generator 5700 with wave guide 5702 may be mounted on a trial frame, such as an adjustable goggle, for stress-free packaging to the shockwave delivery accessories. The trial frame goggles may be configured to stabilize the fluidics, electronic, and/or shockwave wave guides and apply gentle contact with the eye or eyelids. The trial frames may be configured to have an adjustable vertex distance between the frame and the cornea. In some embodiments, the vertex distance may be adjusted to position the shockwave generator about 12 mm or more above the eye. One or more shockwave wave guides may extend from the trial frames to the surface of the eye.

In some embodiments, the shockwave wave guide 5702 may comprise a tubular wave guide. In some embodiments, the shockwave wave guide 5702 may comprise a solid rod. It will be understood by one of ordinary skill in the art that the wave guide 5702 may comprise any shape as desired so as to transmit the shockwaves generated by the shockwave generator to the eye.

In some embodiments, the shockwave wave guide 5702 may comprise a material having a reflectivity of about 40% or more. For example, in some embodiments, the shockwave wave guide 5702 may comprise stainless steel, titanium alloys, aluminum alloys, graphene polymers, metallized ceramics, or the like, or any combination thereof.

The shockwave wave guide 5702 may comprise stainless steel tube having an outer diameter within a range of about 1 mm to about 8 mm.

Figure 58:
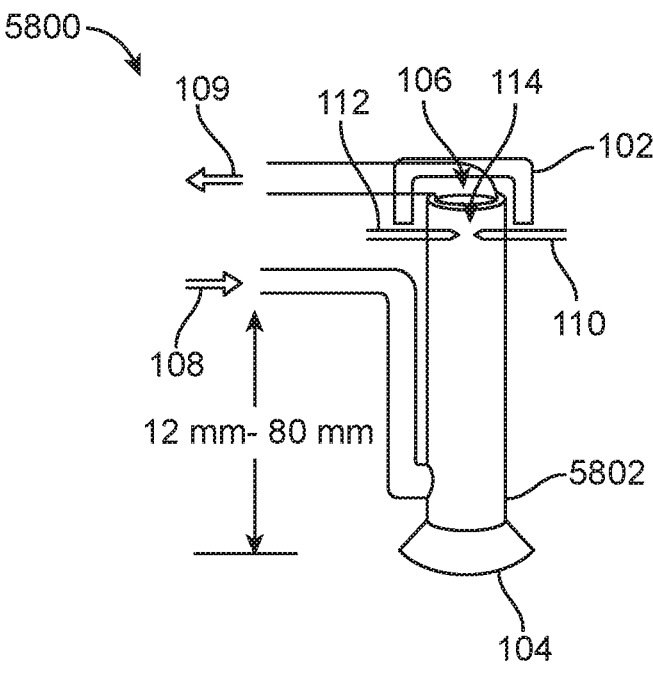
FIG. 58 shows a side cross-sectional view of an exemplary shockwave wave guide, in accordance with embodiments.

FIG. 58 shows a side cross-sectional view of an exemplary shockwave generator 5800 comprising a wave guide 5802. The shockwave generator 5800 may be substantially similar to any of the shockwave generators described herein. For example, the shockwave generator 5800 may comprise a first electrode 110 and a second electrode 112 disposed within a housing 102. The housing 102 may comprise a fluid-filled chamber 106 and an eye-contacting surface 104.

The housing 102 may be substantially tubular, with the electrodes 110, 112 disposed near a proximal end of the fluid-filled chamber 106 and the eye-contacting surface 104 disposed at a distal end of the fluid-filled chamber 106 with an elongated central portion providing a wave guide 5802 therebetween. The proximal end of the fluid-filled chamber 106 may be configured to act as a reflector in order to focus the shockwaves towards a desired pre-determined location via the wave guide. Alternatively, or in combination, one or more reflectors may be coupled to an internal surface of the fluid-filled chamber 106 in order to focus the shockwaves. An inner wall of the fluid filled chamber 106 may be ellipsoidal in shape. Alternatively, or in combination, a distal portion of the wave guide 5082 may be configured to focus the shockwaves to a predetermined location on or below the surface of the eye. The eye-contacting surface 104 may be configured to be coupled to a surface of an eye of a patient. A coupling fluid or gel, for example a water column, may be on or under the eye-contacting surface 104 in order to facilitate contact between the eye-contacting surface 104 and the surface of the eye and/or in order to facilitate transmission of the shockwave from the shockwave generator 5800 to the eye as described herein. The first and second electrodes 110, 112 may be co-axially aligned with one another such that a gap 114 is formed between the distal tips of the electrodes 110, 112. The shockwave generator 5800 may be configured to generate one or more shockwaves. The wave guide 5802 may be configured to transmit the shockwaves from the electrodes to the eye-contacting surface 104.

In some embodiments, the shockwave generator 5800 may further comprise a fluid inlet 108 and a fluid outlet 109 in fluid communication with the fluid-filled chamber 106 as described herein. The fluid may be circulated within the fluid-filled chamber via the fluid inlet and the fluid outlet. The fluid inlet may be configured to deliver fluid to a distal portion of the shockwave generator (e.g., a distal portion of the wave guide) and the fluid outlet may be configured to remove fluid from a proximal portion of the shockwave generator (e.g., near the electrodes) such that fluid flows through the housing in a direction opposite that of the direction of shockwave travel.

The shockwave wave guide may comprise stainless steel tube having an outer diameter within a range of about 1 mm to about 8 mm.

In some embodiments, the wave guide may have a length within a range of about 1 cm to about 2 cm. In some embodiments, the wave guide may be about 12 mm or more in length. For example, the wave guide may have a length within a range of about 12 mm to about 80 mm.

In some embodiments, one or more shockwave generators with wave guide may be coupled to a fluid-filled contact lens as described herein.

In some embodiments, one or more shockwave generators with wave guide may be mounted on a trial frame, such as an adjustable goggle, as described herein.

Figure 59:
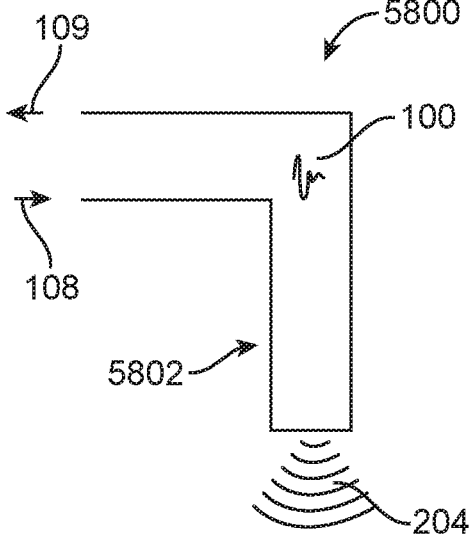
FIG. 59 shows a schematic of a wireframe tubing shockwave wave guide, in accordance with embodiments.

FIG. 59 shows a schematic representation of a wireframe tubing shape of the shockwave wave guide 5800.

Figure 60:
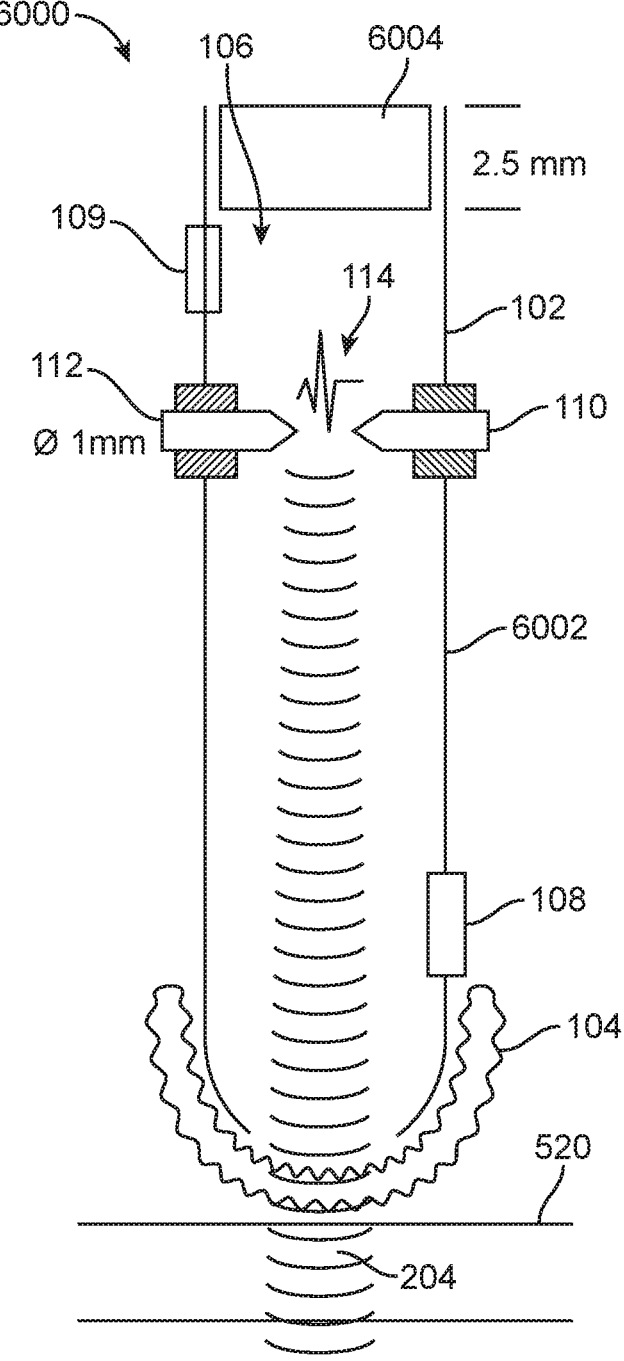
FIG. 60 shows a side cross-sectional view of an exemplary shockwave wave guide, in accordance with embodiments.

FIG. 60 shows a side cross-sectional view of an exemplary shockwave generator 6000 comprising a wave guide 6002. The shockwave generator 6000 may be substantially similar to any of the shockwave generators described herein. For example, the shockwave generator 6000 may comprise a first electrode 110 and a second electrode 112 disposed within a housing 102. The housing 102 may comprise a fluid-filled chamber 106 and an eye-contacting surface 104. The housing 102 may be substantially tubular, with the electrodes 110, 112 disposed near a proximal end of the fluid-filled chamber 106 and the eye-contacting surface 104 disposed at a distal end of the fluid-filled chamber 106 with an elongated central portion 6002 providing a wave guide therebetween. The eye-contacting surface 104 may, for example, comprise a PET membrane as described herein. The proximal end of the fluid-filled chamber 106 may be configured to act as a reflector in order to focus the shockwaves towards a desired pre-determined location via the wave guide. Alternatively, or in combination, one or more reflectors may be coupled to an internal surface of the fluid-filled chamber 106 in order to focus the shockwaves. An inner wall of the fluid-filled chamber 106 may be ellipsoidal in shape. Alternatively, or in combination, a distal portion of the wave guide 6002 may be configured to focus the shockwaves to a predetermined location on or below the surface of the eye. The eye-contacting surface 104 may be configured to be coupled to a surface of an eye of a patient. A coupling fluid or gel, for example a water column, may be on or under the eye-contacting surface in order to facilitate contact between the eye-contacting surface 104 and the surface of the eye and/or in order to facilitate transmission of the shockwave from the shockwave generator 6000 to the eye as described herein. The first and second electrodes 110, 112 may be co-axially aligned with one another such that a gap 114 is formed between the distal tips of the electrodes 110, 112. The shockwave generator 6000 may be configured to generate one or more shockwaves. The wave guide 6002 may be configured to transmit the shockwaves from the electrodes to the eye-contacting surface.

In some embodiments, a rod stop 6004 may be disposed at the proximal end of the housing 102. The rod stop 6004 may reflect acoustic energy from the proximal end of the housing 102 back into the tissue.

In some embodiments, the shockwave generator 6000 may further comprise a fluid inlet 108 and a fluid outlet 109 in fluid communication with the fluid-filled chamber 106 as described herein. The fluid may be circulated within the fluid-filled chamber 106 via the fluid inlet 108 and the fluid outlet 109. The fluid inlet 108 may be configured to deliver fluid to a distal portion of the shockwave generator 6000 (e.g., a distal portion of the wave guide 6002) and the fluid outlet 109 may be configured to remove fluid from a proximal portion of the shockwave generator 6000 (e.g., near the electrodes 110, 112) such that fluid flows through the housing 102 in a direction opposite that of the direction of shockwave travel.

The shockwave wave guide 6002 may comprise stainless steel tube having an outer diameter within a range of about 1 mm to about 8 mm, for example about 1 mm, about 2 mm, about 3 mm, about 5 mm, or about 8 mm. The wave guide may have a wall thickness of about 0.5 mm.

In some embodiments, the wave guide 6002 may have a length within a range of about 1 cm to about 2 cm. In some embodiments, the wave guide 6002 may be about 12 mm or more in length. For example, the wave guide 6002 may have a length within a range of about 12 mm to about 80 mm, for example about 20 mm.

In some embodiments, one or more shockwave generators 6000 with wave guide 6002 may be coupled to a fluid-filled contact lens as described herein.

In some embodiments, one or more shockwave generators 6000 with wave guide 6002 may be mounted on a trial frame, such as an adjustable goggle, as described herein.

Figure 61:
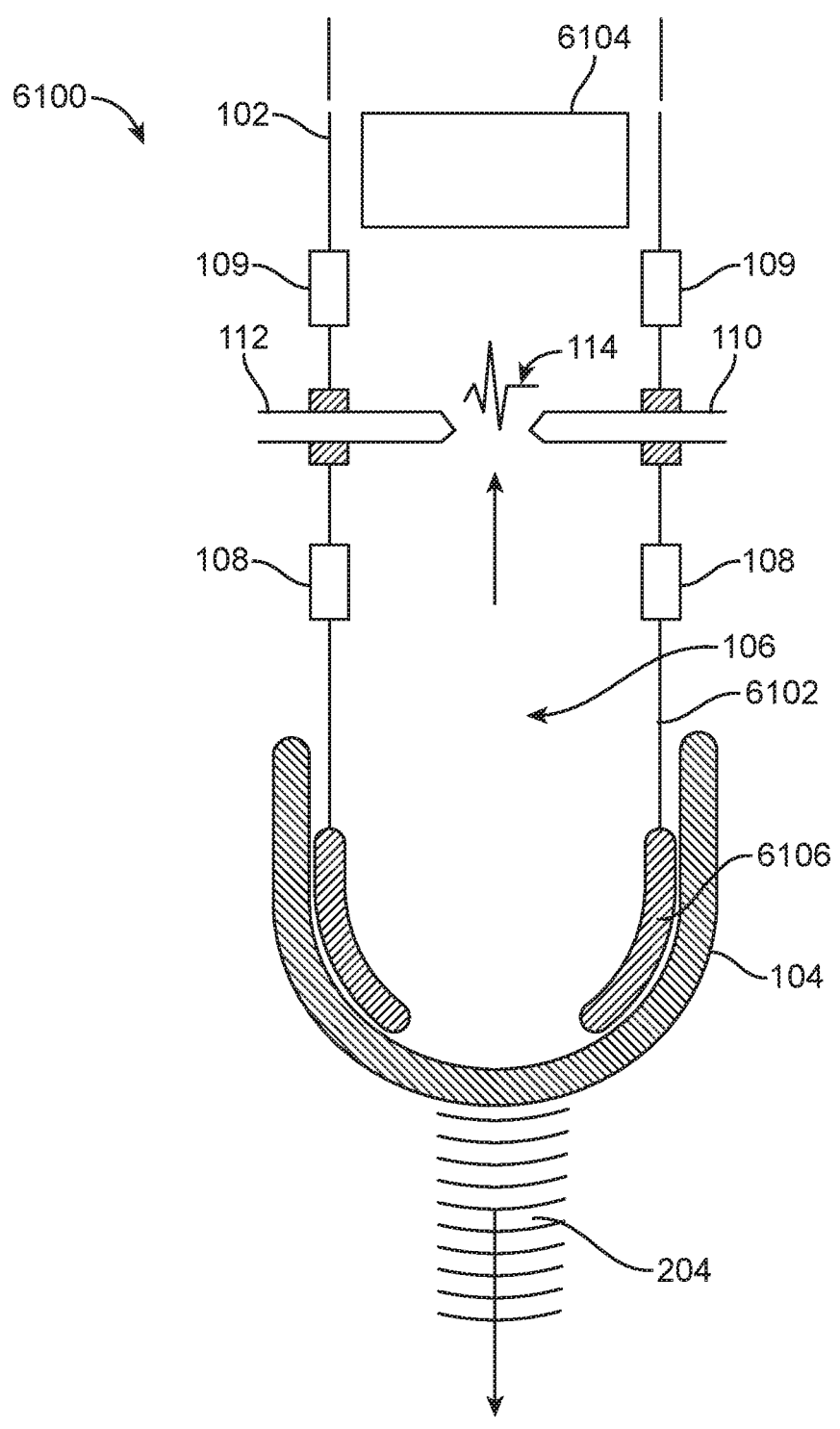
FIG. 61 shows a side cross-sectional view of an exemplary shockwave wave guide, in accordance with embodiments.

FIG. 61 shows a side cross-sectional view of an exemplary shockwave generator 6100 comprising a wave guide 6102. The shockwave generator 6100 may be substantially similar to any of the shockwave generators described herein.

For example, the shockwave generator 6100 may comprise a first electrode 110 and a second electrode 112 disposed within a housing 102. The housing 102 may comprise a fluid-filled chamber 106 and an eye-contacting surface 104. The housing 102 may be substantially tubular, with the electrodes 110, 112 disposed near a proximal end of the fluid-filled chamber 106 and the eye-contacting surface 104 disposed at a distal end of the fluid-filled chamber 106 with an elongated central portion 6102 providing a wave guide therebetween. The eye-contacting surface 104 may, for example, comprise a PET membrane as described herein. The proximal end of the fluid-filled chamber 106 may be configured to act as a reflector in order to focus the shockwaves towards a desired pre-determined location via the wave guide 6102. Alternatively, or in combination, one or more reflectors may be coupled to an internal surface of the fluid-filled chamber 106 in order to focus the shockwaves. An inner wall of the fluid filled chamber 106 may be ellipsoidal in shape. Alternatively, or in combination, a distal portion of the wave guide 6102 may be configured to focus the shockwaves to a predetermined location on or below the surface of the eye. The eye-contacting surface 104 may be configured to be coupled to a surface of an eye of a patient. A coupling fluid or gel, for example a water column, may be on or under the eye-contacting surface in order to facilitate contact between the eye-contacting surface 104 and the surface of the eye and/or in order to facilitate transmission of the shockwave from the shockwave generator to the eye as described herein. The first and second electrodes 110, 112 may be co-axially aligned with one another such that a gap 114 is formed between the distal tips of the electrodes 110, 112. The shockwave generator 6100 may be configured to generate one or more shockwaves. The wave guide 6102 may be configured to transmit the shockwaves from the electrodes to the eye-contacting surface 104.

In some embodiments, a distal end of the wave guide 6102 may comprise one or more reflectors 6106. The one of more reflectors 6106 may be configured to focus the shockwaves to a predetermined location on or below the surface of the eye as described herein.

In some embodiments, a rod stop 6104 may be disposed at the proximal end of the housing 102. The rod stop 6104 may reflect acoustic energy from the proximal end of the housing 012 back into the tissue.

In some embodiments, the first and second electrodes 110, 112 may be heat shrunk. Heat shrinking may protect the electrodes from unwanted moisture contact which may lead to misdirected high voltage discharges.

In some embodiments, the shockwave generator 6100 may further comprise a fluid inlet 108 and a fluid outlet 109 in fluid communication with the fluid-filled chamber 106 as described herein. The fluid may be circulated within the fluid-filled chamber 106 via the fluid inlet 108 and the fluid outlet 109. The fluid inlet 108 may be configured to deliver fluid to a distal portion of the shockwave generator 6100 (e.g., a distal portion of the wave guide) and the fluid outlet 109 may be configured to remove fluid from a proximal portion of the shockwave generator 6100 (e.g., near the electrodes) such that fluid flows through the housing 102 in a direction opposite that of the direction of shockwave travel.

The shockwave wave guide 6102 may comprise stainless steel tube having an outer diameter within a range of about 1 mm to about 8 mm, for example about 2 mm. The wave guide 6102 may have a wall thickness of about 0.5 mm.

In some embodiments, the wave guide 6102 may have a length within a range of about 1 cm to about 2 cm. In some embodiments, the wave guide 6102 may be about 12 mm or more in length. For example, the wave guide 6102 may have a length within a range of about 12 mm to about 80 mm.

In some embodiments, one or more shockwave generators 6100 with wave guide 6102 may be coupled to a fluid-filled contact lens as described herein.

In some embodiments, one or more shockwave generators 6100 with wave guide 6102 may be mounted on a trial frame, such as an adjustable goggle, as described herein.

In some embodiments, an array of shockwave generators 6100 with wave guides 6102 may be positioned adjacent the eye (e.g., coupled to a fluid-filled contact lens) to target one or more treatment locations as described herein. For example, similar to the array of FIG. 63, 8 wave guides may be positioned in a first row at 12 mm, 10 wave guides may be positioned in a second row at 16 mm, and a single large wave guide may be positioned in the center of the eye (at 0 mm). It will be understood by one of ordinary skill in the art any number of wave guides may be positioned adjacent the eye in any pattern desired to treat a target tissue of interest.

Figure 62:
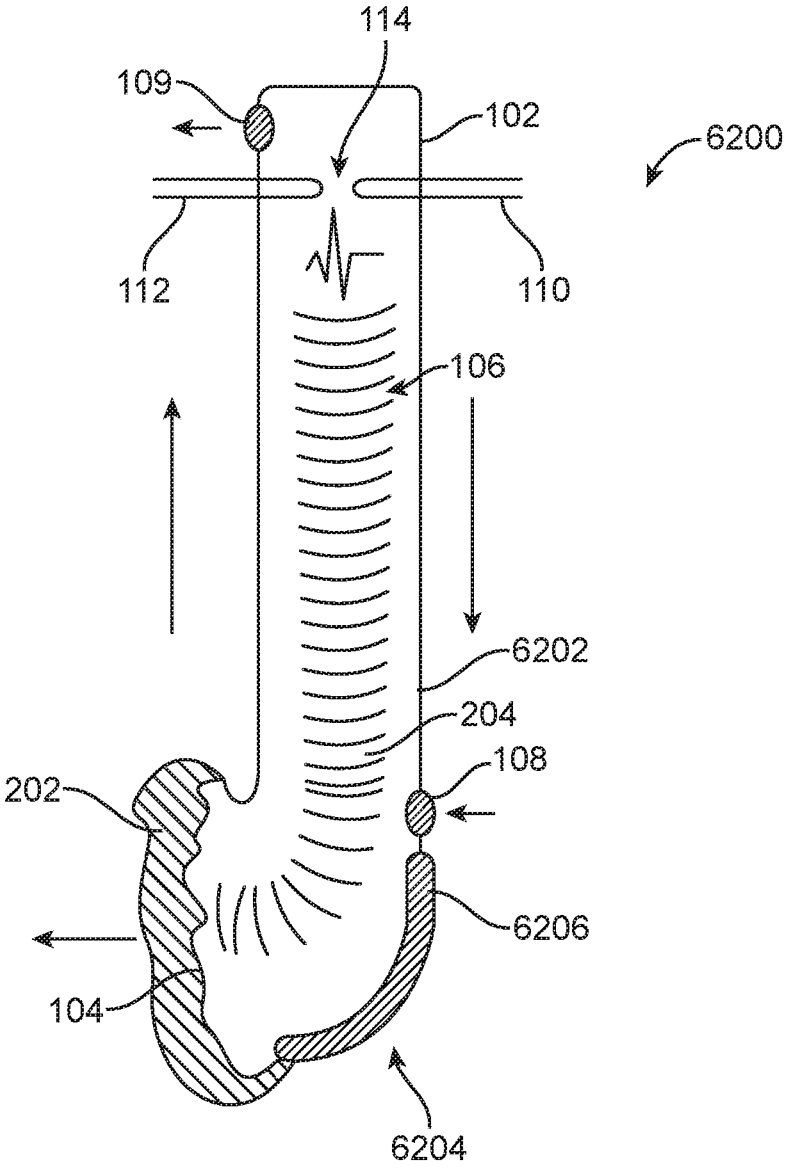
FIG. 62 shows a side cross-sectional view of an exemplary parabolic shockwave wave guide, in accordance with embodiments.

FIG. 62 shows a side cross-sectional view of an exemplary parabolic shockwave wave guide 6202. The shockwave generator 6200 and wave guide 6202 may be substantially similar to the shockwave wave guides shown in FIGS. 60 and 61 except that the distal end 6204 of the wave guide 6202 may be curved. The parabolic shockwave wave guide 6202 may comprise a parabolic reflector 6206 configured to enable peripheral access to the eye.

Figures 63, 64, 65:
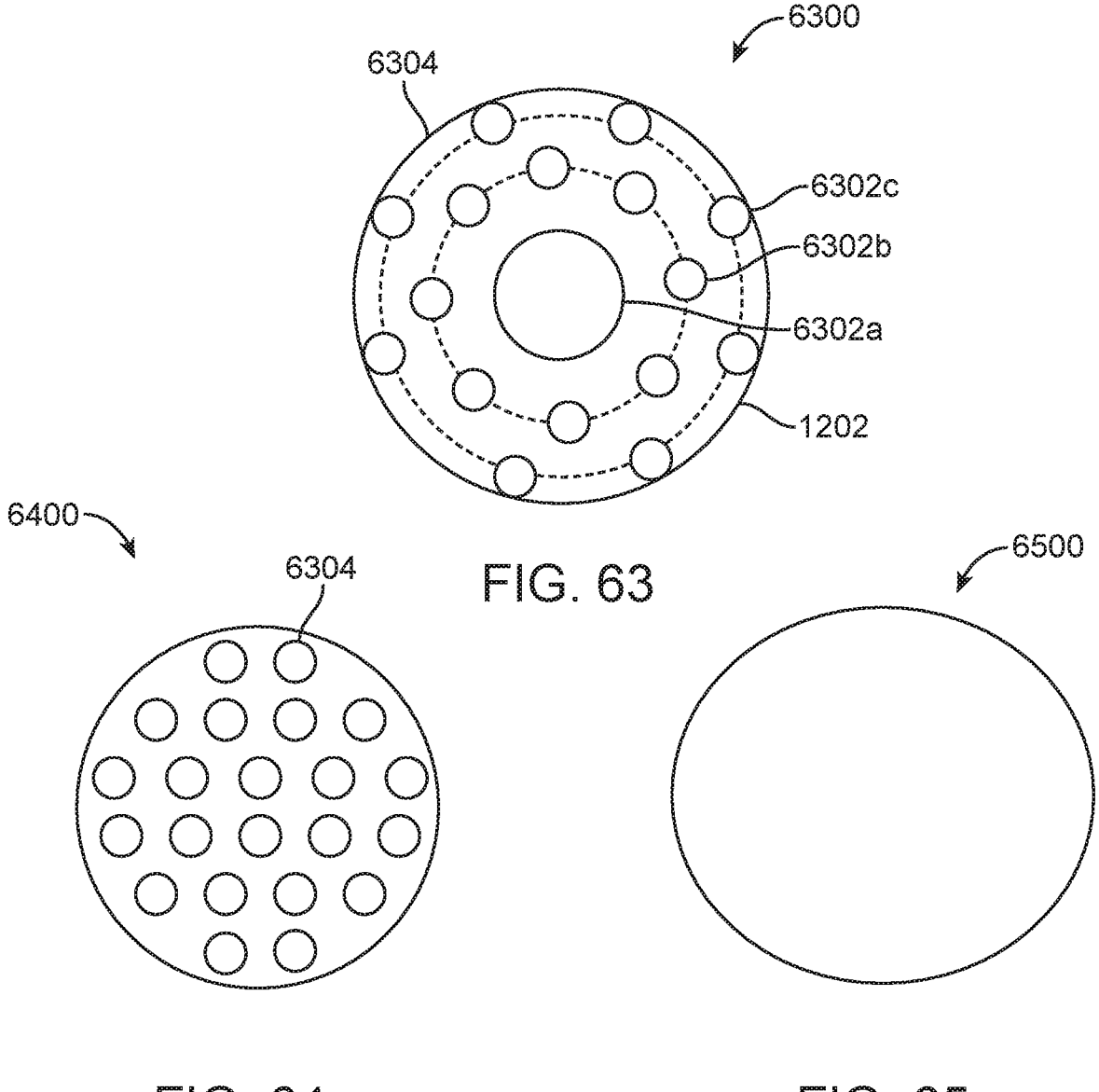
FIG. 63 shows a top view of an exemplary contact lens comprising an array of shockwave waveguides, in accordance with embodiments.
FIG. 64 shows a top view of an exemplary contact lens comprising an array for shockwave generators for enface meibomian gland treatment, in accordance with embodiments.
FIG. 65 shows a top view of an exemplary contact lens for dry eye disease treatment, in accordance with embodiments.

FIG. 63 shows a top view of an exemplary contact lens 6300 comprising an array of shockwave wave guides 6302. Any of the shockwave wave guides described herein may be coupled to a contact lens 6304 as an array of shockwave generators 6302, similar to other arrays described herein. In some embodiments, an array of shockwave generators with wave guides 6302 may be positioned adjacent the eye to target one or more treatment locations as described herein. For example, a central large (8 cm outer diameter) wave guide 6302*a* may be coupled to the center of the contact lens so as to treat the crystalline lens and/or retina as described herein. A first row of shockwave wave guides 6302*b* may be disposed about 12 mm radially outward therefrom in order to treat the trabecular meshwork and/or Schlemm's Canal as described herein. A second row of shockwave wave guides 6032*c* may be disposed at about 16 mm in order to treat the pars plana and PVZ as described herein. A suction ring disposed on the outer edge of the contact lens (at about 19 mm diameter) may couple the contact lens 6304 to the surface of the eye or eyelid as described herein.

FIG. 64 shows a top view of an exemplary contact lens 6400 comprising an array of shockwave generators 6402 for enface meibomian gland treatment. The contact lens 6400 may have a radius of curvature of about 7.8 mm and about 12 mm.

FIG. 65 shows a top view of an exemplary contact lens 6500 for dry eye disease treatment. The contact lens 6500 may comprise a corneal contact lens which may be configured (e.g., shaped, comprise an appropriate material, etc.) to act as an efficient acoustic reflector as described herein.

Figure 66:
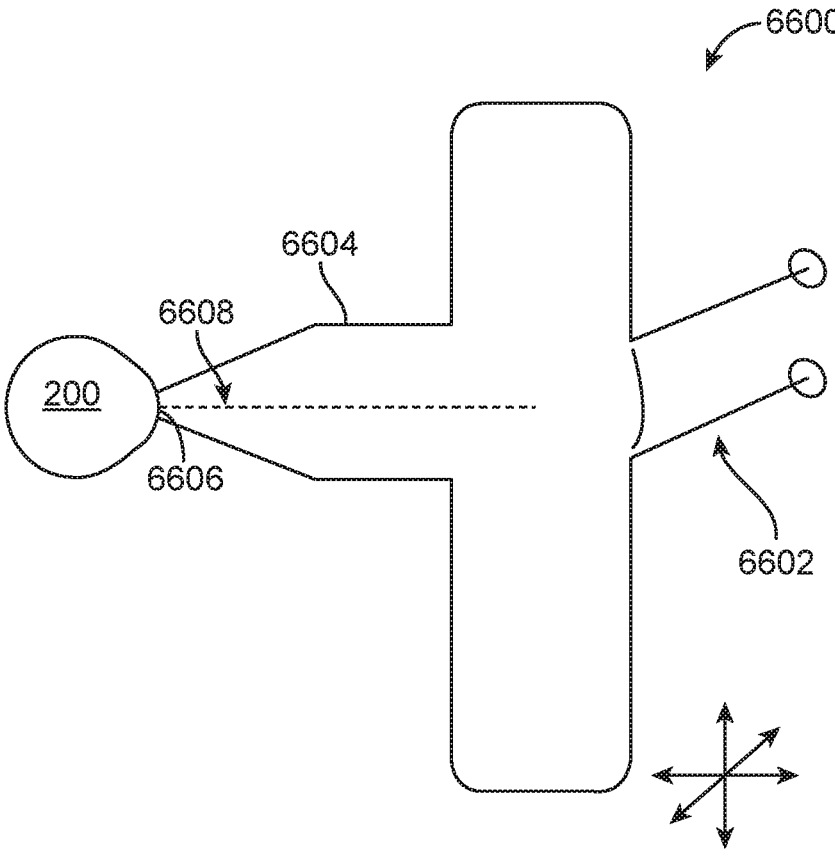
FIG. 66 shows a side view of an exemplary treatment system including an integrated imaging system, in accordance with embodiments.

FIG. 66 shows a side view of an exemplary treatment system 6600 including an integrated imaging system 6002. The system 6600 may comprise any of the shockwave generators described herein. For example, the system 6600 may comprise a shockwave generator having a waveguide 6604 coupled to a docking contact lens 6606. The shockwave generator may comprise a central aperture 6608 configured to allow an imaging system 6602 to be integrated therein. The imaging system 6602 may have a slit-lamp configuration with the central aperture 6608 providing a viewport. The viewport may enable the physician to view the eye before, during, or after treatment as described herein. The viewport may be referenced. In some embodiments, the imaging system 6602 may comprise an OCT imaging system. An NIR (e.g., 1064 nm) wavelength laser of the OCT imaging system may be configured to penetrate through water and into the tissue in order to provide interoperative imaging feedback as described herein. In some embodiments, a plurality of shockwave generators may be disposed in one or more annular rings around the viewport. In some embodiments, the shockwave generator electronics and fluidics, including saline pumping, degassing, and vacuum, may be housed on the slit lamp assembly. The slit lamp assembly configuration may be configured to be used while the patient is sitting upright.

Figure 67:
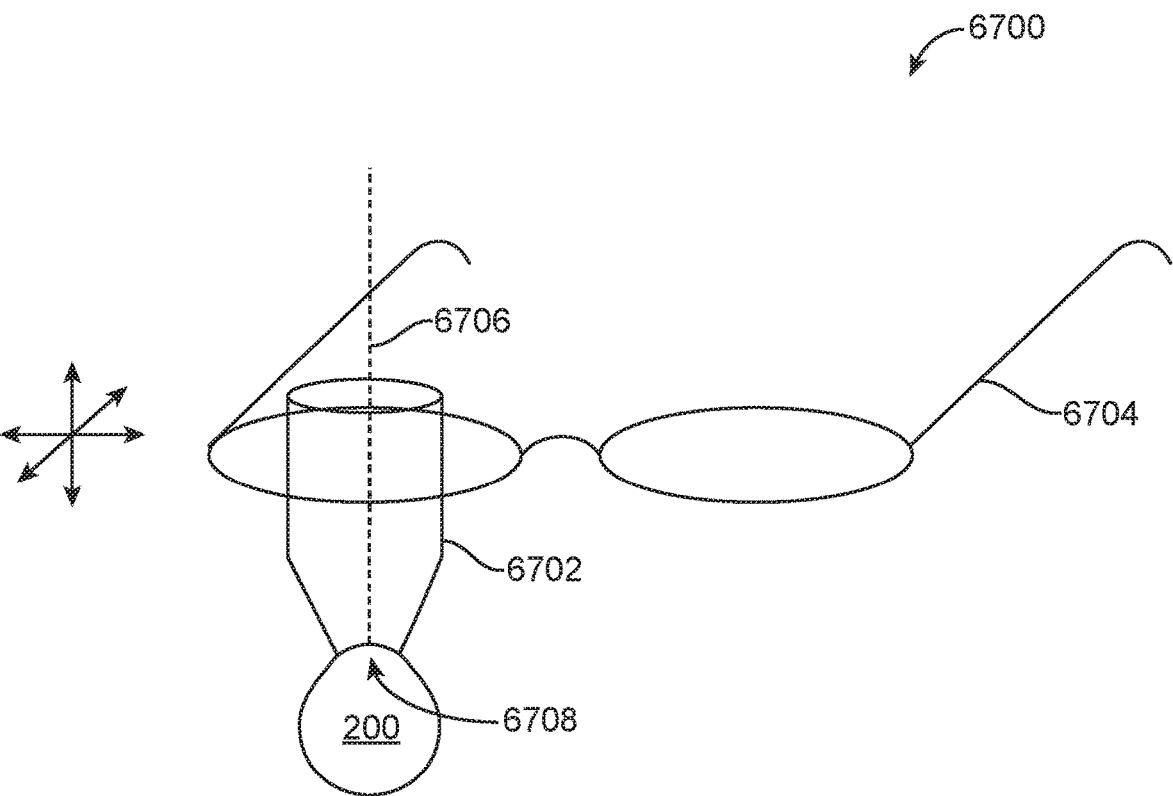
FIG. 67 shows a side view of an exemplary treatment system including an integrated imaging system, in accordance with embodiments.

FIG. 67 shows a side view of an exemplary treatment system including 6700 an integrated imaging system 6706. The system 6700 may comprise any of the shockwave generators described herein. For example, the system 6700 may comprise a shockwave generator having a waveguide 6702 coupled to trial frames 6704 and a docking contact lens. The shockwave generator may comprise a central aperture 6708 configured to allow an imaging system 6706 to be integrated therein. The imaging system 6706 may comprise an ultrasound biomicroscopy (UBM), ultrasound (US) imaging, and/or optical coherence tomography (OCT) apparatus or system. The imaging system 6706 may be used to capture one or more images of the eye before, during, or after treatment as described herein. A processor or controller may be coupled to the energy source and the imaging system and be configured with instructions to deliver energy to the shockwave generators and image the tissue during treatment. The system 6700 may also comprise a display coupled to the processor that allows the user to visualize the tissue prior to, before, or after treatment. The display may show images which allow the user to see the tissue treated and plan the treatment. Images shown on the display may be provided in real-time and can be used to prior to treatment to allow the user to align the tissue and/or monitor the tissue effects of treatment (e.g., cavitation) in order to make sure that unintended effects of treatment aren't occurring (e.g., structures of the eye changing locations relative to one another when not desired, etc.).

In some embodiments, the shockwave generator electronics, wave guide(s), and fluidic interfaces may be mounted on the trial frame 6704 as described herein. The fluidic enclosures, including saline pumping, degassing, and vacuum, may be housed on an IV pole as described herein. The trial frame configuration may be configured to be used while the patient is supine/recumbent.

Figure 68:
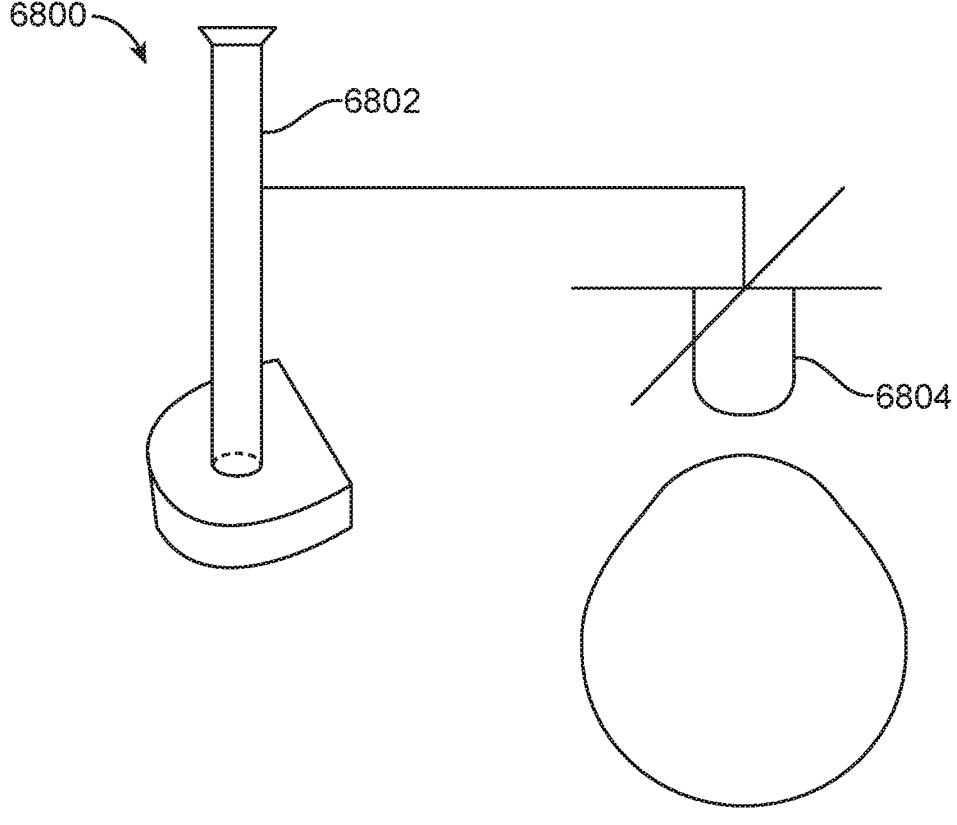
FIG. 68 shows a side view of an exemplary treatment system including an integrated imaging system, in accordance with embodiments.

FIG. 68 shows a side view of an exemplary treatment system 6800 including an integrated imaging system 6802. The system 6800 may comprise any of the shockwave generators described herein. For example, the system 6800 may comprise a shockwave generator having a waveguide 6804 coupled to an operating microscope 6802. The shockwave generator may comprise a central aperture configured to allow an imaging system to be integrated therein. The imaging system 6802 may comprise an ultrasound biomicroscopy (UBM), ultrasound (US) imaging, and/or optical coherence tomography (OCT) apparatus or system. The imaging system 6802 may be used to capture one or more images of the eye before, during, or after treatment as described herein. A processor or controller may be coupled to the energy source and the imaging system 6802 and be configured with instructions to deliver energy to the shockwave generators and image the tissue during treatment. The system 6800 may also comprise a display coupled to the processor that allows the user to visualize the tissue prior to, before, or after treatment. The display may show images which allow the user to see the tissue treated and plan the treatment. Images shown on the display may be provided in real-time and can be used to prior to treatment to allow the user to align the tissue and/or monitor the tissue effects of treatment (e.g., cavitation) in order to make sure that unintended effects of treatment aren't occurring (e.g., structures of the eye changing locations relative to one another when not desired, etc.).

In some embodiments, the shockwave generator electronics and fluidics may be mounted on an arm of the operating microscope 6802 or an IV pole as described herein. The operating microscope configuration may be configured to be used while the patient is supine/recumbent.

Figure 69:
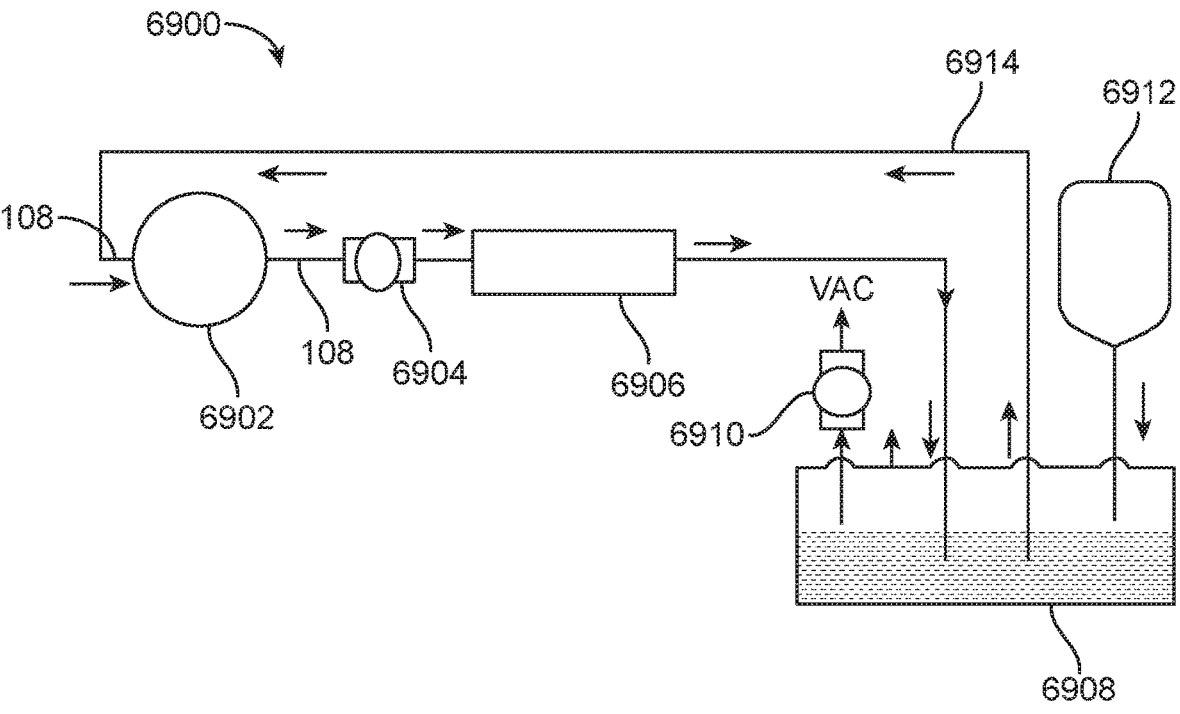
FIG. 69 shows a schematic of an exemplary system for bubble extraction, in accordance with embodiments.

FIG. 69 shows a schematic of an exemplary system 6900 for bubble extraction. Any of the shockwave generating systems described herein may be configured for real-time intraoperative bubble extraction. The system 6900 may comprise one or more shockwave generators 6902, which may be substantially similar to any of the shockwave generators described herein. The shockwave generator(s) 6902 may be configured to generate one or more shockwaves. The one or more shockwave generators 6902 may comprise a fluid-filled chamber comprising a fluid, such as saline, disposed therein. In some embodiments, the shockwave generator 6902 may further comprise a fluid inlet 108 and a fluid outlet 109 in fluid communication with the fluid-filled chamber. The fluid may be used to couple the shockwave generated by the fiber to the surface of the eye. The fluid may be circulated within the fluid-filled chamber via the fluid inlet 108 and the fluid outlet 109. Fluid circulation may enable continuous extraction of thermal buildup, cavitation bubbles, and ions generated during shockwave formation as pulsed delivery of the shockwaves is ongoing. Efficient removal of bubbles formed during shockwave generation may be desirable to prevent interference of lingering bubbles within the fluid on the formation and/or direction of additional shockwaves and associated unintended effects. Bubble removal may also improve acoustic energy delivery. In some embodiments, it may be desirable to degas and recirculate the fluid through the fluid-filled chamber. The recirculation system may comprise a first pump 6904 which moves fluid from the fluidic components of the shockwave generator(s) 6902 to a bubble extraction device 6906 (e.g., a PermaSelect 2500 by MedArray). Fluid may be pulled through the bubble extraction device 6906 to a vacuum chamber 6908 (e.g., an air-sealed schott-duran glass vessel) by a vacuum pump 6910 coupled to the vacuum chamber 6908. A saline reservoir bag 6912 may be in fluid communication with the vacuum chamber 6908 for fluid exchange and balancing. The degassed fluid may be pulled from the vacuum chamber 6908 into the shockwave generator(s) 6902 by the first pump 6904 to complete the recirculation system 6900. The recirculation system 6900 may operate with common peristatic pump flow rates and vacuum pump ranges. In some embodiments, the fluid flowing out of the fluid-filled chamber via the fluid outlet 109 may be sampled periodically or continuously as described herein.

In some embodiments, the fluid recirculation system 6900 may be configured to remove fluid from the fluid-filled chamber at a rate within a range of about 0.5 L/min to about 1 L/min. For example, the fluid may be recirculated at a rate within a range of about 750 ml/min to about 1000 ml/min.

In some embodiments, the entire volume of the fluid-filled chamber (or fluid-filled contact lens/balloon) may be replaced by the fluid recirculation system 5900 with new degassed fluid after every shockwave generation.

In some embodiments, the recirculation rate may be about 100 mL/minute.

In some embodiments, one or more of the pumps may be a peristatic pump.

In some embodiments, the fluid recirculation tubing 6914 may comprise a hollow tubing. In some embodiments, the fluid recirculation tubing 6914 may comprise a silicone tube or sleeve.

In some embodiments, the fluid recirculation tubing 6914 may comprise interior surface chemistries which reduce or prevent entrapment of the cavitation bubbles within the tubing 6914. For example, the tubing 6914 may be coated with a surfactant.

In some embodiments, an IV pole may be positioned proximal to the eye for housing one or more of the saline bag reservoir 6912, the programmable pulser (2 KV/10 KHz), vacuum pump 6910 for bubble extraction device, pump 6904 for extraction of saline from the contact lens to drive into the bubble extraction device, vacuum for eye suction, reservoir bottle for fluids exchange and balancing, and/or tubing 6914 with valves for control.

Figure 70:
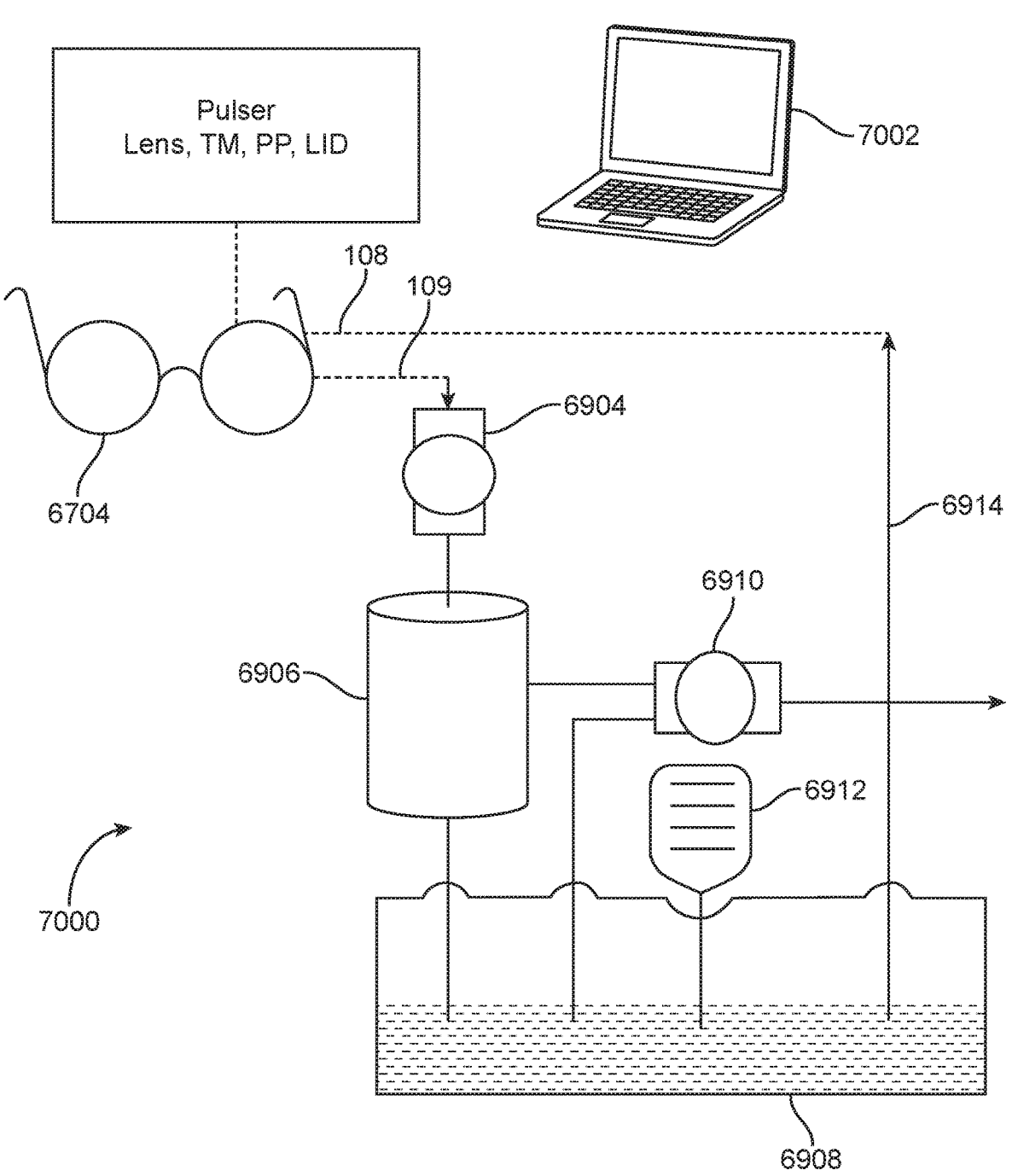
FIG. 70 shows a schematic of an exemplary system for bubble extraction, in accordance with embodiments.

FIG. 70 shows a schematic of an exemplary system 7000 for bubble extraction. The bubble extraction system 7000 may be substantially similar to the system of FIG. 69, with integration into a trial-frame goggle 6704. The trial-frame goggle 6704 may be configured to support the shockwave generator electronics, optional wave guide(s), and fluidic interfaces as described herein and may be substantially similar to any of the goggles described herein.

Figure 71:
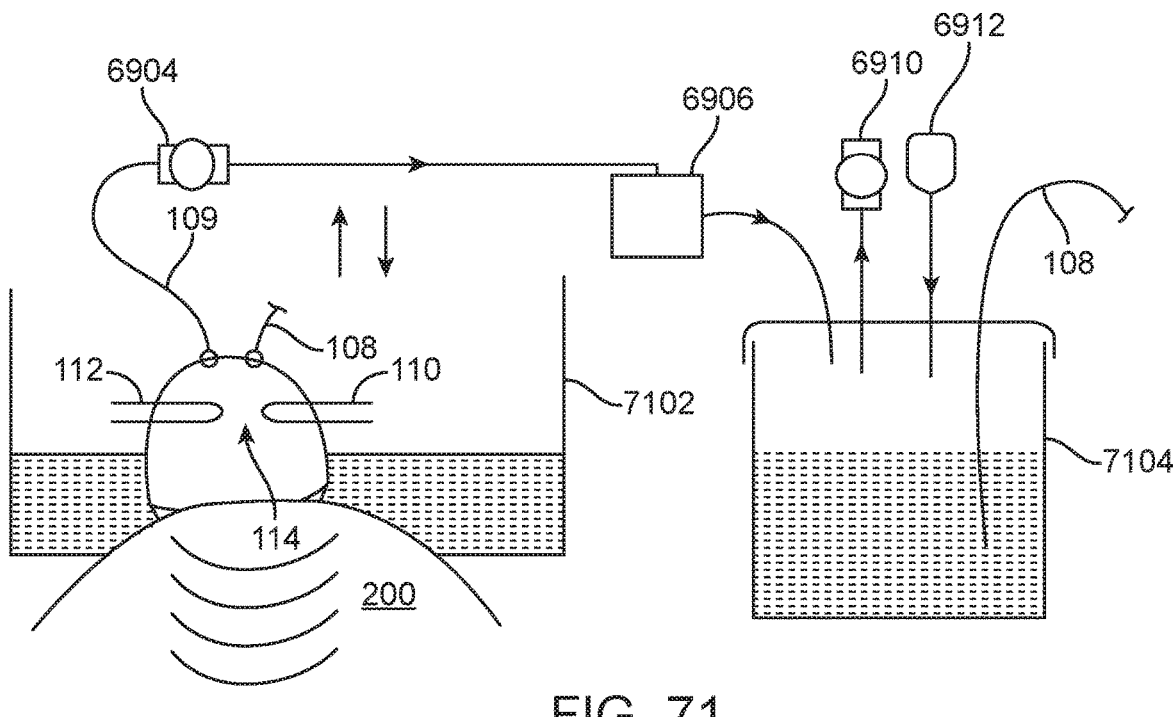
FIG. 71 shows a schematic of an exemplary system for bubble extraction, in accordance with embodiments.

FIG. 71 shows a schematic of an exemplary system 7100 for bubble extraction coupled to a contact lens balloon 7102 disposed on an eye 200 of a patient. The bubble extraction system 7100 may be substantially similar to the system of FIG. 70, with a large vacuum tank mounted on an IV pole. The contact lens balloon 7102 may be substantially similar to any of the contact lenses or balloons described herein. The vacuum tank may hold a large volume of saline, for example 7 liters, compared to the system of FIG. 70 which may be configured to hold a smaller volume, for example 500 ml.

Figure 72:
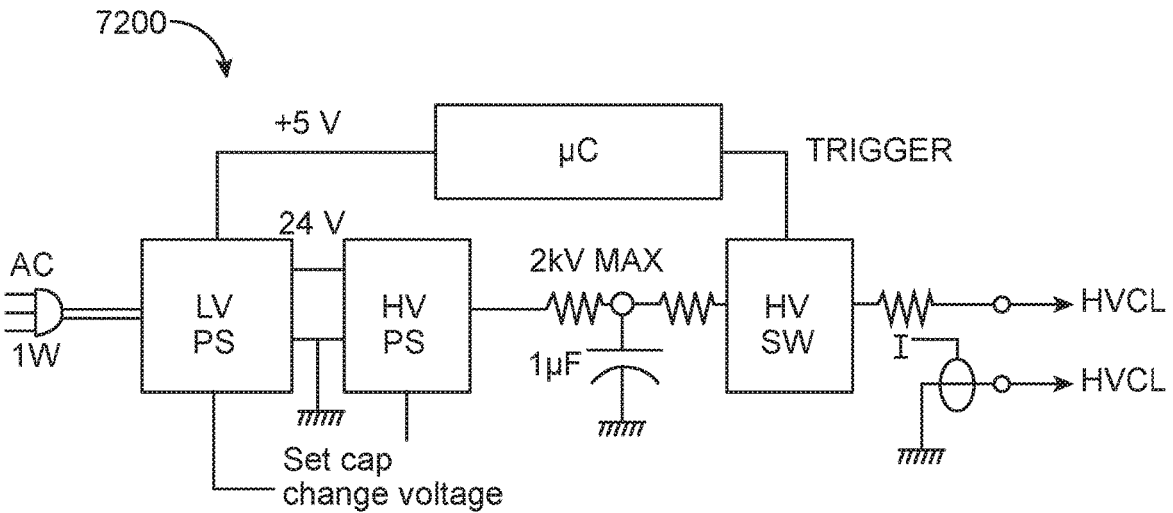
FIG. 72 shows an electrical schematic of an exemplary treatment system, in accordance with embodiments.

FIG. 72 shows an electrical schematic of an exemplary treatment system 7200 configuration. A low voltage power supply module LVPS may be configured to generate one or more voltages, for example, +5V, +24V, and +12V. A programmable 0-2 kV high voltage power supply module HVPS may be configured to deliver power to a capacitor. The HVPS unit may, for example, be configured to deliver around 125 Watts to the capacitor. The capacitor may be rapidly (about 1 μsec) discharged by the high voltage switch HVSW into a saline container. The saline container may direct pressure waves to the tissue (e.g., through an acoustically transparent fluid tight membrane). A microcontroller (e.g., Arduino class) may be configured to control timing and PCT interfacing as well as monitoring safety interlocks.

Figure 73:
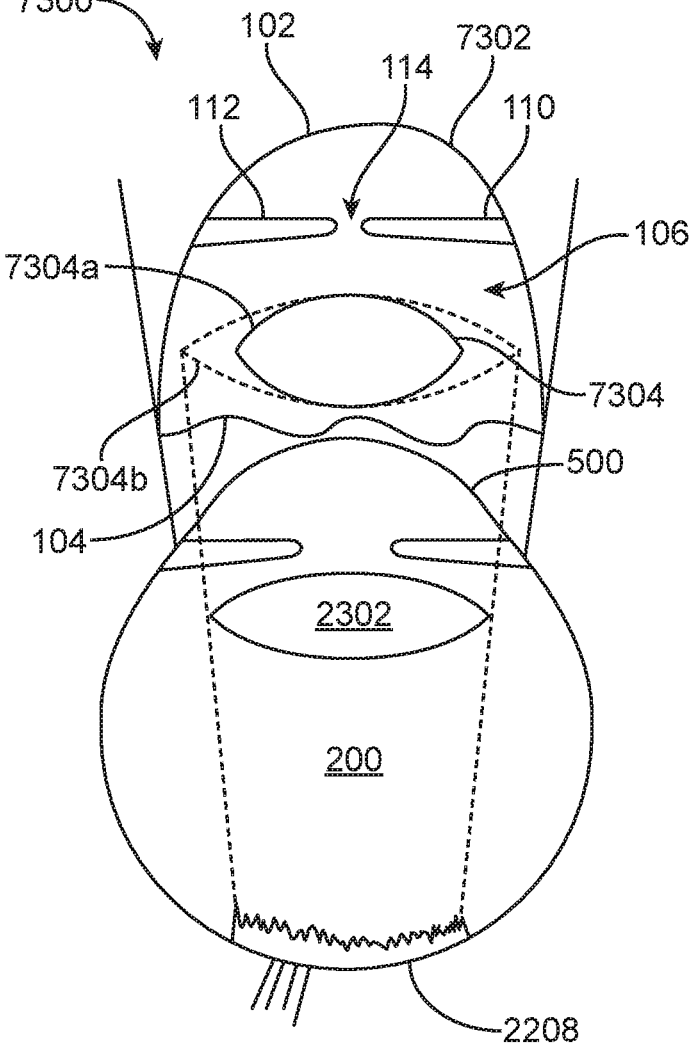
FIG. 73 shows a side cross-sectional view of an exemplary variable focus treatment system, in accordance with embodiments.

FIG. 73 shows a side cross-sectional view of an exemplary variable focus treatment system 7300. The system 7300 may be substantially similar to the system shown in FIG. 40 and may be used for treatment of the crystalline lens 2302 (or IOL), the retina 2208, and/or other target locations within the eye. The system 7300 may comprise a large diameter shockwave generator 7302 configured to deliver shockwaves onto the lens and/or retina. The shockwave generator 7302 may be substantially similar to any of the shockwave generators described herein. For example, the shockwave generator 7302 may comprise a first electrode 110 and a second electrode 112 disposed within a housing 102. The housing 102 may comprise a fluid-filled chamber 106 and an eye-contacting surface 104. The fluid-filled chamber 106 may be configured to act as a parabolic reflector in order to focus the planar shockwaves towards a desired pre-determined location. Alternatively, or in combination, one or more reflectors may be coupled to an internal surface of the fluid-filled chamber 106 in order to focus the shockwaves. The one or more reflectors may, for example, comprise an electronically variable acoustic lens 7304, which may enable variable or adjustable focusing of the shockwaves along the z-plane on the crystalline lens 2302 (or IOL) and/or the macular of the retina 2208. An inner wall of the fluid filled chamber 106 may be ellipsoidal in shape. The eye-contacting surface 104 may be configured to be coupled to a surface of an eye of a patient. A coupling fluid or gel, for example a water column, may be on or under the eye-contacting surface 104 in order to facilitate contact between the eye-contacting surface 104 and the surface 500 of the eye and/or in order to facilitate transmission of the shockwave from the shockwave generator 7302 to the eye. A suction ring may be disposed on an outer edge of the shockwave generator in order to couple the shockwave generator to a cornea or sclera of the eye. The first and second electrodes 110, 112 may be co-axially aligned with one another such that a gap 114 is formed between the distal tips of the electrodes 110, 112. The shockwave generator 7302 may be configured to generate one or more shockwaves. The electronically variable acoustic lens 7304 may comprise a first shape 7304a configured to focus the shockwaves to a first location (e.g., the lens 2302 for softening) and a second shape 7304b configured to focus the shockwaves to a second location (e.g., the retina 2208 for sonostimulation). The electronically variable acoustic lens 7304 may be configured to electronically steer the shockwaves to any treatment location or combination of treatment locations desired.

Figure 74:
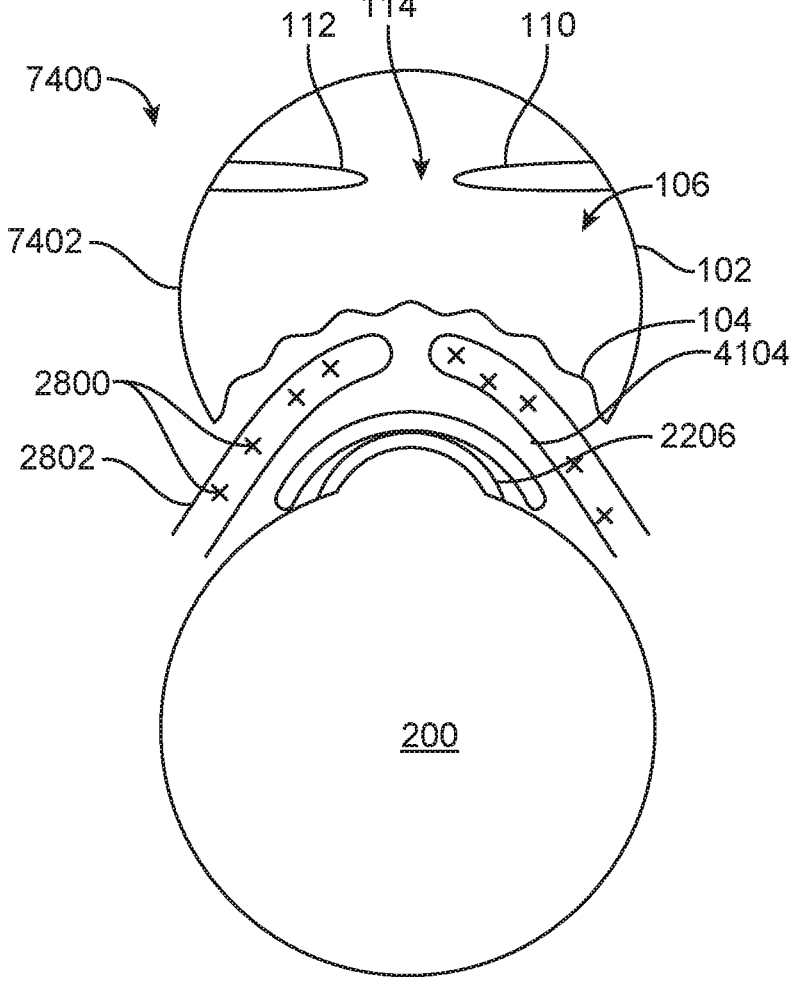
FIG. 74 shows a side cross-sectional view of an exemplary treatment system for dry eye disease, in accordance with embodiments.

FIG. 74 shows a side cross-sectional view of an exemplary treatment system 7400 for dry eye disease. The system 7400 may be substantially similar to the system shown in FIG. 41 and may be used to deliver shockwave therapy to the eyelids 2802 while protecting the cornea 2206 from the shockwaves. The system 7400 may comprise a large diameter shockwave generator 7402 configured to deliver shockwaves to the eyelid 2802 of the eye 200. The shockwave generator 7402 may be substantially similar to any of the shockwave generators described herein. For example, the shockwave generator 7402 may comprise a first electrode 110 and a second electrode 112 disposed within a housing 102. The housing 102 may comprise a fluid-filled chamber 106 and an eye-contacting surface 104. The fluid-filled chamber 106 may be configured to act as a parabolic reflector in order to focus the planar shockwaves towards a desired pre-determined location. Alternatively, or in combination, one or more reflectors may be coupled to an internal surface of the fluid-filled chamber 106 in order to focus the shockwaves. An inner wall of the fluid filled chamber 106 or a reflector coupled to an internal surface of the fluid-filled chamber 106 may be ellipsoidal in shape. The eye-contacting surface 104 may be configured to be coupled to an eyelid 2802 of a patient (e.g., when the patient's eye is closed). The eye-contacting surface 104 may comprise a highly compliant membrane material in order to facilitate coupling to the eyelids 2802. A corneal sparing contact lens 4104 may be disposed on the cornea 2206 of the patient under the eyelid 2802 and may act as an acoustic reflector in order to redirect shockwaves passing through the eyelid 2802 away from the cornea 2206. The heat spreading contact lens 4104 may be configured to act as an acoustic reflector and direct the shockwaves towards one or more meibomian glands 2800 in order to treat dry eye as described herein. A suction ring may be disposed on an outer edge of the shockwave generator in order to couple the shockwave generator to the eyelids. The first and second electrodes 110, 112 may be co-axially aligned with one another such that a gap 114 is formed between the distal tips of the electrodes 110, 112. The shockwave generator 7402 may be configured to generate one or more shockwaves.

Figure 75:
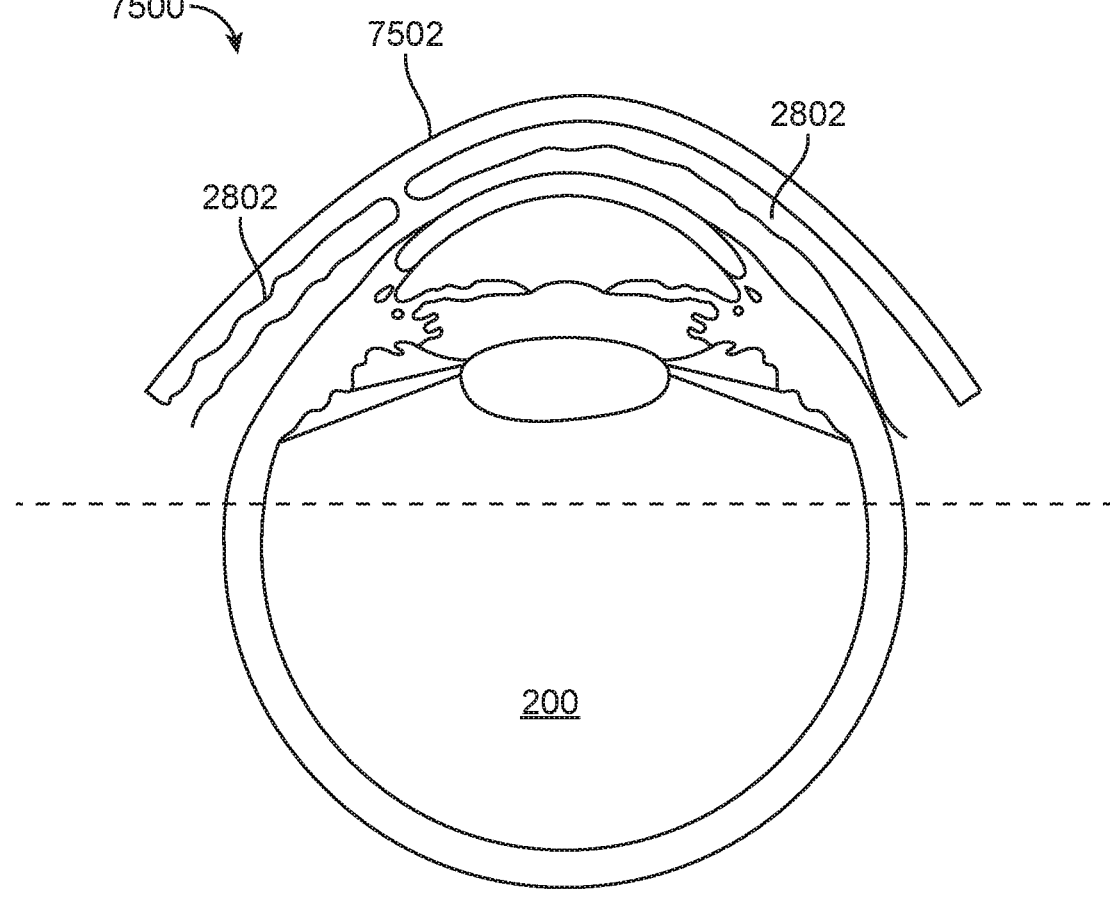
FIG. 75 shows a side cross-sectional view of an exemplary treatment system for trans-palpebral treatment, in accordance with embodiments.

FIG. 75 shows a side cross-sectional view of an exemplary treatment system 7500 for trans-palpebral treatment. The system 7500 may comprise any of the shockwave generators described herein. In some embodiments, the eye-contacting surface of the shockwave generator may be coupled to an eyelid 2802 of a patient when the patient's eye is closed. In some embodiments, the system 7500 may comprise a palpebral contact lens 7502 configured to be coupled to the eyelid 2802 of the patient. In some embodiments, the eye-contacting surface of the shockwave generator may comprise the palpebral contact lens 7502. In some embodiments, the eye-contacting surface of the shockwave generator may be configured to contact the palpebral contact lens 7502. In some embodiments, the shockwave generator may be configured to deliver shockwaves through the palpebral contact lens 7502 to a predetermined location on or below the surface of the eye (or eyelid). The shockwaves may travel through the eyelids 2802 to the predetermined treatment location.

Figure 76:
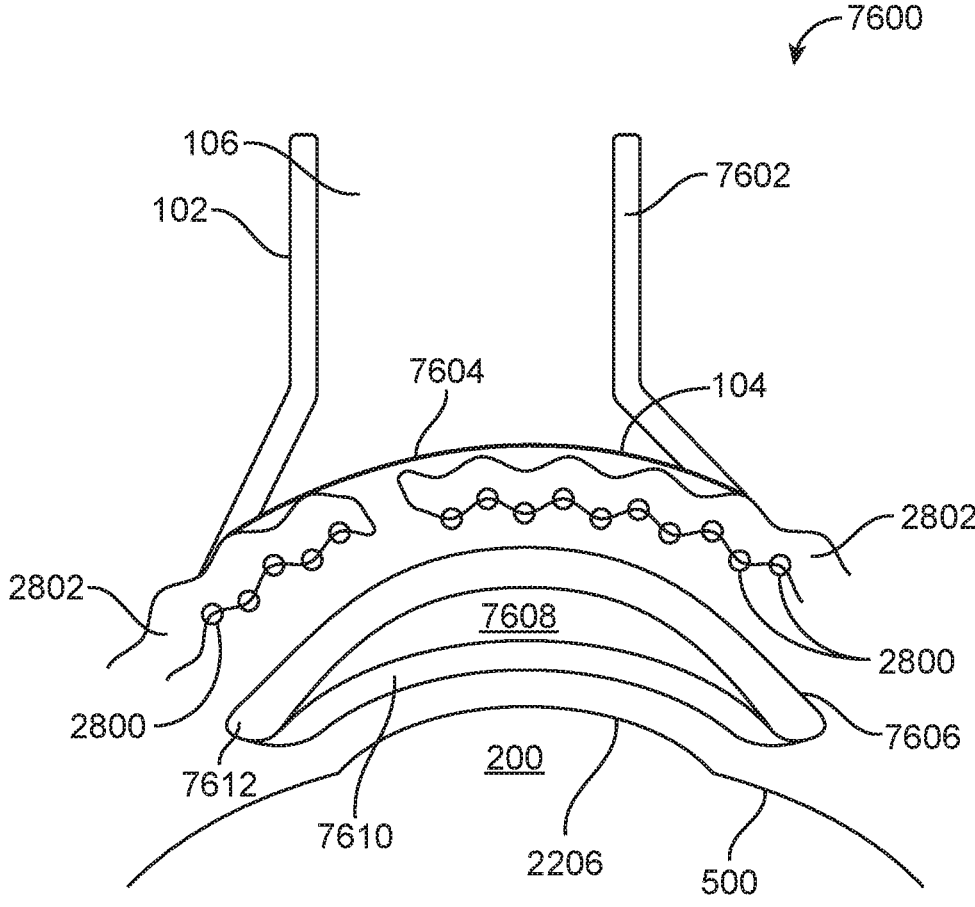
FIG. 76 shows a side cross-sectional view of an exemplary treatment system for dry eye disease, in accordance with embodiments.

FIG. 76 shows a side cross-sectional view of an exemplary treatment system 7600 for dry eye disease. The system 7600 may comprise any of the shockwave generators described herein. For example, the system may comprise a shockwave generator having a waveguide 7602 coupled to trial frames and a docking contact lens 7604. The system 7600 may be used to deliver shockwave therapy to the eyelids 2802 while protecting the cornea 2206 from shockwaves. The shockwave generator may be substantially similar to any of the shockwave generators described herein. For example, the shockwave generator may comprise a first electrode and a second electrode disposed within housing. The housing 102 may comprise a fluid-filled chamber 106 and an eye-contacting surface 104. The fluid-filled chamber 106 may be configured to act as a parabolic reflector in order to focus the planar shockwaves towards a desired pre-determined location. Alternatively, or in combination, one or more reflectors may be coupled to an internal surface of the fluid-filled chamber 106 in order to focus the shockwaves. An inner wall of the fluid filled chamber 106 or a reflector coupled to an internal surface of the fluid-filled chamber 106 may be ellipsoidal in shape. The eye-contacting surface 104 may be configured to be coupled to an eyelid 2802 of a patient (e.g., when the patient's eye is closed). The eye-contacting surface 104 may comprise a highly compliant membrane material in order to facilitate coupling to the eyelids 2802. A corneal sparing contact lens 7606 may be disposed on the cornea 2206 of the patient under the eyelid 2802 and may act as an acoustic reflector in order to redirect shockwaves passing through the eyelid 2802 away from the cornea. The acoustic reflective lens 7606 may direct the shockwaves towards one or more meibomian glands 2800 in order to treat dry eye as described herein. The acoustic reflective lens 7606 may be air-filled 7608 PET and/or PMMA scleral contact lens. A cornea-contacting surface 7610 of the lens may comprise PMMA and an eyelid-contacting surface 7612 of the lens may comprise PET. Alternatively, a cornea-contacting surface 7610 of the lens may comprise PET and an eyelid-contacting surface 7612 of the lens may comprise PMMA. The impedance mismatch between the fluid-filled chamber 106 and the air-filled reflective lens 7606 may be large enough (e.g., about 3500 times greater) to cause the energy directed towards the cornea 2206 to be reflected back to the eyelid 2802. A suction ring may be disposed on an outer edge of the shockwave generator in order to couple the shockwave generator to the eyelids 2802. The first and second electrodes may be co-axially aligned with one another such that a gap is formed between the distal tips of the electrodes. The shockwave generator may be configured to generate one or more shockwaves.

In some embodiments, the air-filled scleral contact lens 7606 may be sterilizable and/or disposable.

In some embodiments, the air-filled scleral contact lens 7606 may have a total thickness of about 300 μm. In some embodiments, the PET surface of the lens may have a thickness of about 12 μm. In some embodiments, the PMMA surface of the lens may have a thickness of about 200 μm. In some embodiments, the air chamber 7612 may have a thickness of about 100 μm.

In some embodiments, the air-filled scleral contact lens 7606 may have a diameter of about 19 mm.

In some embodiments, the air-filled scleral contact lens 7606 may have a dual curve with a vault.

Figure 77:
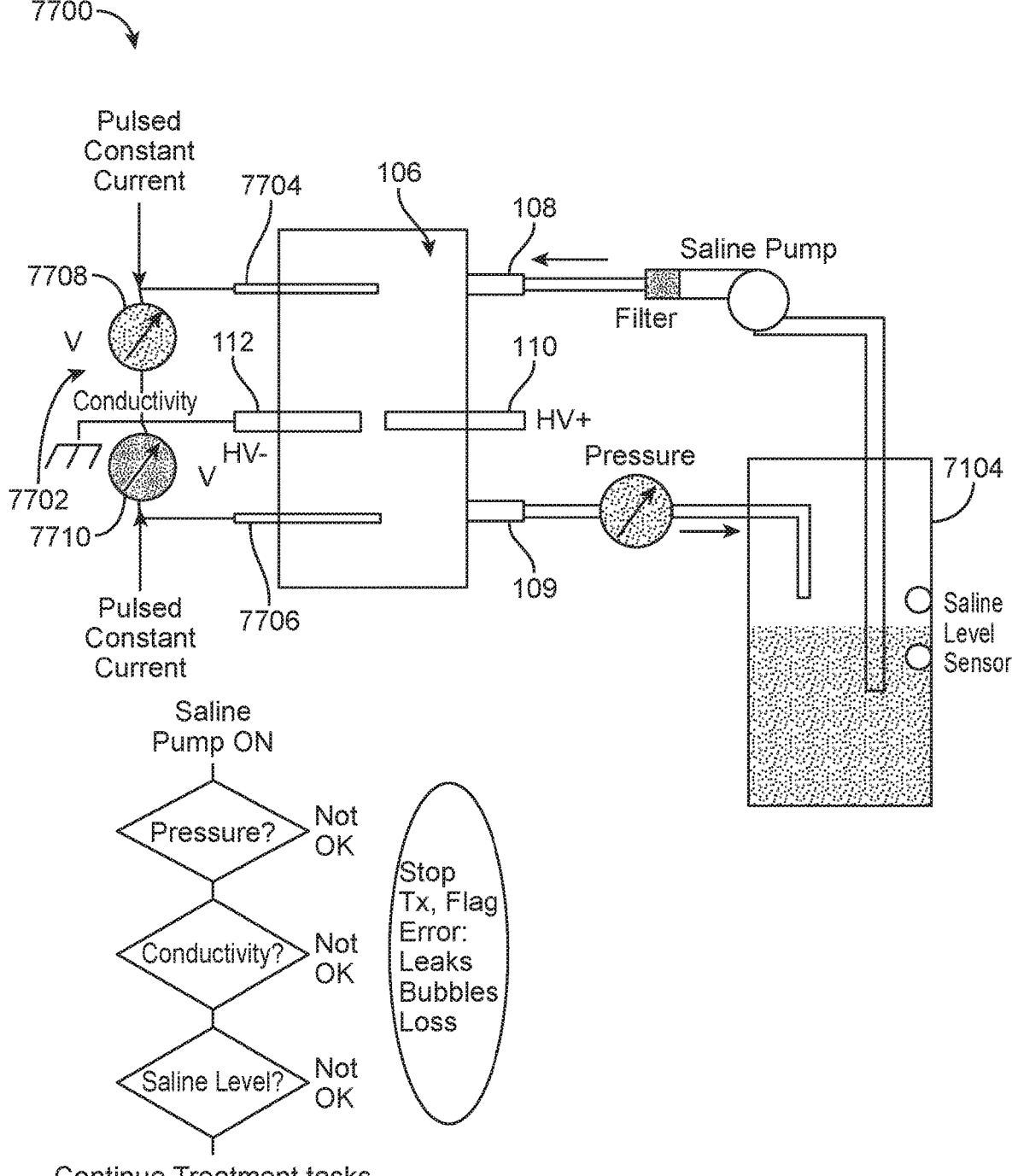
FIG. 77 shows a schematic of an exemplary system for conductivity measurement, in accordance with embodiments.

FIG. 77 shows a schematic of an exemplary system 7700 for conductivity measurement. Any of the systems described herein may comprise a conductivity sensor 7702 configured to measure a conductivity of the fluid flowing within or out of the fluid-filled chamber 106. In some embodiments, the conductivity sensor 7702 may be fluidly coupled to the fluid outlet 109 (which is fluidly coupled to a saline reservoir 7104) but not located in the fluid-filled chamber 106. In some embodiments, the conductivity sensor 7702 may be embedded in the fluid-filled chamber 106. The conductivity sensor 7702 may sample the conductivity of the fluid within the fluid-filled chamber 106 periodically or continuously in order to determine the extent of electrode erosion. For example, saline conductivity may be sampled (e.g., as a proxy for measuring the gap distance between the shockwave electrodes as the electrodes erode and metallic ions are released into the saline) and the voltage delivered to the shockwave electrodes 110, 112 may be adjusted to account for any changes in conductivity sensed. In some embodiments, the conductivity sensor 7702 may comprise a pair of platinum electrodes 7704, 7706 disposed at a fixed distance apart (e.g., 2 cm). Dual constant current sources 7708, 7710 (e.g., 1 mA) may inject known current at a known distance (e.g., 1 cm) from a ground electrode (e.g., electrode 112 in some embodiments). The cell constant can be calibrated using circulating solutions of known conductivity such as phosphate-buffered saline, potassium chloride, saline, or the like at fixed concentrations. For example, 0.9% sodium chloride has a conductivity of about 16 mS/cm (~K=1 cell calibration) and can be used for calibration of the conductivity sensor 7702. The cell constant is a multiplier constant specific to a conductivity sensor. The measured current is multiplied by the cell constant to determine the electrical conductivity of the solution. The cell constant, known as K, refers to a theoretical electrode consisting of two 1 cm square plates 1 cm apart. Increases in conductivity may be indicative of metal leaching into the fluid of the fluid-filled chamber 106. Decreases in conductivity may be indicative of bubble formation and retention within the fluid-filled chamber 160. In the event that the conductivity changes beyond an acceptable threshold, the treatment may be stopped and the system 7700 may be flushed with fresh fluid to remove metal/bubbles and/or the shockwave generating electrodes 110, 112 may be assessed.

In some embodiments, the dual current sources 7708, 7710 may be pulsed at about 10 KHz in sync (but 180 degree out of phase). The pulsing may have a duty cycle of about 20%. For example, the current sources may pulse "on" for about 20 microseconds and "off" for about 80 microseconds at 10 KHz. 80 microseconds may provide sufficient time to detect and/or compare the direct current voltage at the conductivity electrodes.

In some embodiments, the platinum conductivity electrodes 7704, 7706 may have a diameter of about 6 mm and a width of about 2 mm. The platinum conductivity electrodes 7704, 7706 may be insulated with about 0.1 mm thick stainless steel.

In some embodiments, the platinum conductivity electrodes 7704, 7706 may have a diameter of about 0.5 mm. The platinum conductivity electrodes 7704, 7706 may be insulated with parylene. In some embodiments, the platinum conductivity electrodes 7704, 7706 may have exposed tips synced (out of phase) to the high voltage pulsing of the shockwave generating electrodes 110, 112.

Figure 84:
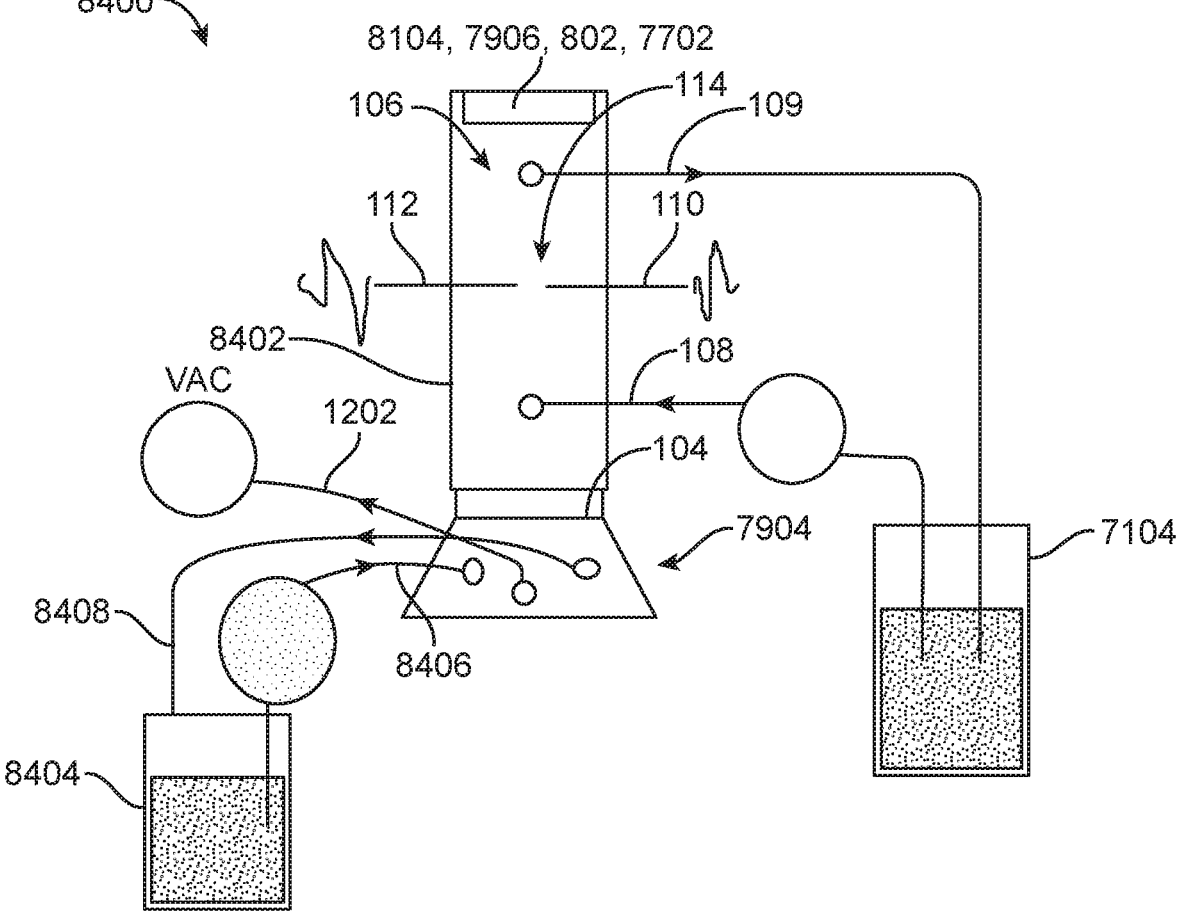
FIG. 84 shows a schematic of an exemplary treatment system including acoustic cross-linking or passive cavitation detection, in accordance with embodiments.

In some embodiments, the conductivity cell may further comprise a passive cavitation detector or an ultraviolet radiation source as described herein (e.g., as in FIGS. 84-85).

Figure 78:
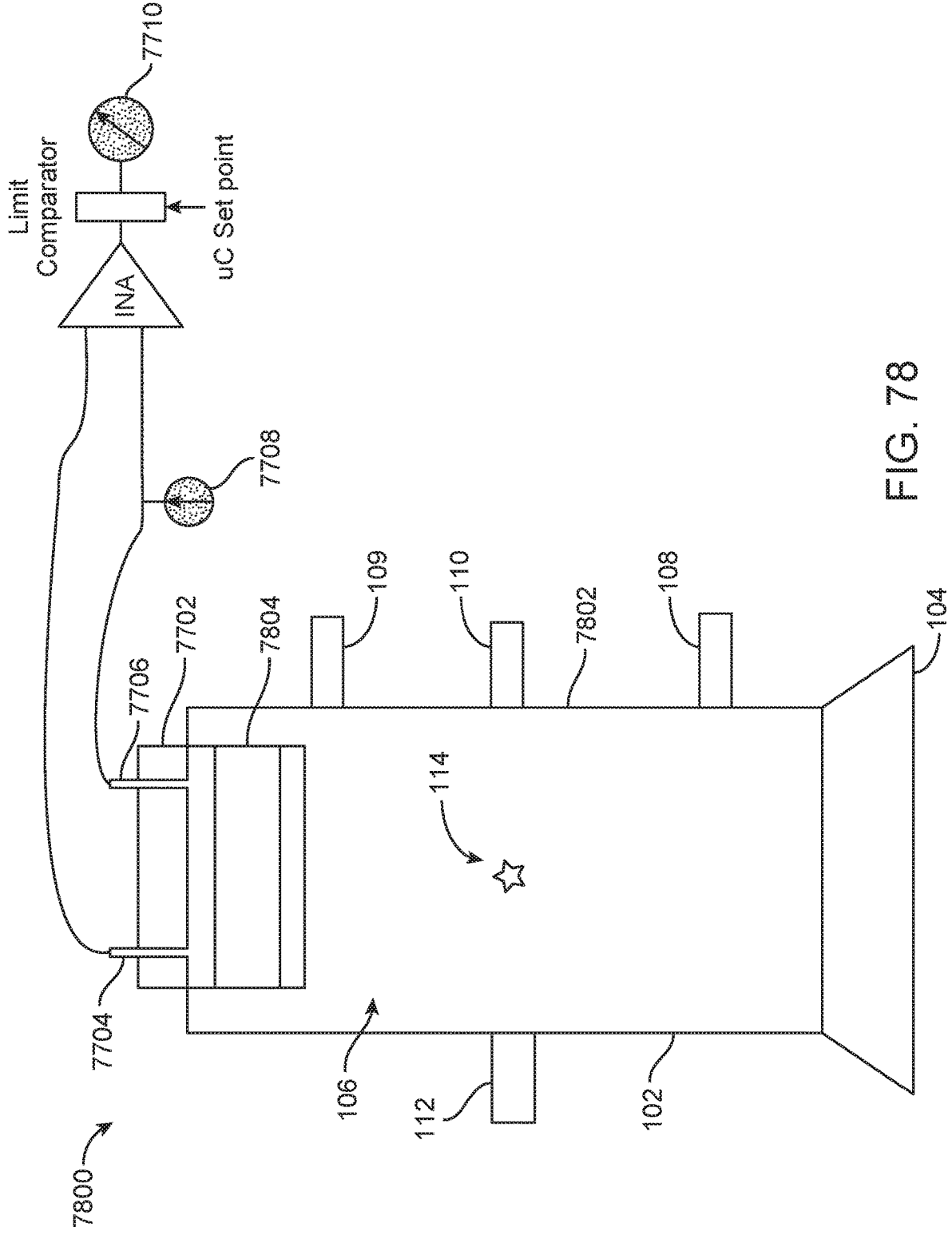
FIG. 78 shows a side view of an exemplary shockwave wave guide including embedded conductivity sensor, in accordance with embodiments.

FIG. 78 shows a side view of an exemplary shockwave generator 7800 comprising a wave guide 7802 and an embedded conductivity sensor 7702. The shockwave wave guide 7802 may be substantially similar to any of the shockwave wave guides described herein. The shockwave generator 7800 may be substantially similar to any of the shockwave generators described herein. For example, the shockwave generator 7802 may comprise a first electrode 110 and a second electrode 112 disposed within a housing 102. The housing 102 may comprise a fluid-filled chamber 106 and an eye-contacting surface 104. The housing 102 may be substantially tubular, with the electrodes disposed near a proximal end of the fluid-filled chamber 106 and the eye-contacting surface 104 disposed at a distal end of the fluid-filled chamber 106 with an elongated central portion 7802 providing a wave guide therebetween. The eye-contacting surface 104 may, for example, comprise a PET membrane as described herein. The eye-contacting surface 104 may be configured to be coupled to a surface of an eye of a patient. A coupling fluid or gel, for example a water column, may be on or under the eye-contacting surface in order to facilitate contact between the eye-contacting surface and the surface of the eye and/or in order to facilitate transmission of the shockwave from the shockwave generator to the eye as described herein. In some embodiments, the distal end of the fluid-filled chamber 106 may be referred to as an acoustic wave emitter. The proximal end of the fluid-filled chamber 106 may comprise a conductivity cell 7804 comprising a conductivity sensor 7702. The conductivity sensor 7702 may comprise a pair of platinum electrodes 7704, 7706 disposed at a fixed distance apart. The pair of platinum electrodes 7704, 7706 may be configured to periodically or continuously sample the conductivity of the fluid in the fluid-filled chamber 106 as described herein.

Figure 79:
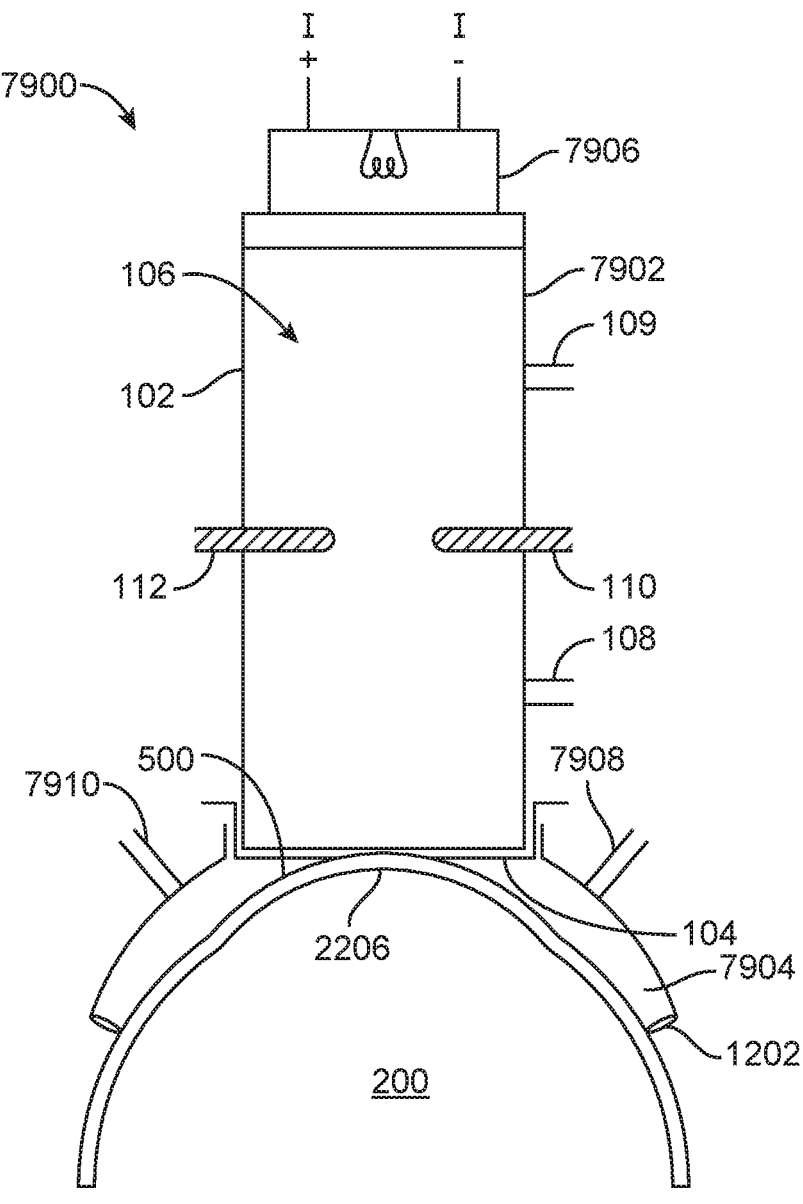
FIG. 79 shows a side view of an exemplary acoustic cross-linking shockwave wave guide, in accordance with embodiments.

FIG. 79 shows a side view of an exemplary acoustic cross-linking shockwave generator 7900 comprising a shockwave wave guide 7902. Acoustic cross-linking may be used to treat keratoconus or corneal ectasia. The shockwave wave guide 7902 may be substantially similar to any of the shockwave wave guides described herein. The shockwave generator 7900 may be substantially similar to any of the shockwave generators described herein. For example, the shockwave generator 7900 may comprise a first electrode 110 and a second electrode 112 disposed within a housing 102. The housing 102 may comprise a fluid-filled chamber 106 and an eye-contacting surface 104. The housing 102 may be substantially tubular, with the electrodes 110, 112 disposed near a proximal end of the fluid-filled chamber 106 and the eye-contacting surface 104 disposed at a distal end of the fluid-filled chamber 106 with an elongated central portion 7902 providing a wave guide therebetween. The eye-contacting surface 104 may, for example, comprise a PET membrane as described herein. The eye-contacting surface 104 may be configured to be coupled to a surface 500 of an eye 200 of a patient. A coupling fluid or gel, for example a water column, may be on or under the eye-contacting surface 104 in order to facilitate contact between the eye-contacting surface 104 and the surface 500 of the eye and/or in order to facilitate transmission of the shockwave from the shockwave generator to the eye as described herein. In some embodiments, a reservoir 7904 of oxygen and/or one or more therapeutic substances may disposed be on or under the eye-contacting surface 104 for drug delivery to the cornea 2206. The reservoir 7904 may be coupled to the eye 200 with a vacuum-sealed fixation ring 1202. Shockwaves generated by the shockwave generator may enhance drug delivery to the cornea 2206 (e.g., to the epithelium) by causing surface fragmentation and/or micro-poration of the corneal tissue of interest to improve drug permeability.

The PET membrane 104 may isolate the high-voltage fluidics from the eye and the drug/oxygen reservoir 7904. The PET membrane 104 may be acoustically transparent. The PET membrane 104 may have a thickness within a range of about 2.5 micrometers to about 12.5 micrometers. The PET film 104 may be configured to withstand at least about 100 PSI saline pressure within the fluid-filled chamber 106. In some embodiments, the PET membrane 104 may be replaced by focusing/defocusing acoustic lenses and/or planar wave meniscus lenses.

In some embodiments, the therapeutic substance may comprise a photosensitizing agent such as riboflavin, a riboflavin nanoparticle, or rose bengal.

Acoustic radiation force (i.e. the force from the shockwaves) may drive the therapeutic substance(s) into the tissue. Alternatively, or in combination, electrospraying via formation of a Taylor cone and coulombic fission may be used to disperse the therapeutic substance(s) onto the tissue surface.

In some embodiments, the reservoir 7904 may comprise a fluid inlet and 7908 a fluid outlet 7910 for circulation of oxygen and/or therapeutic substances from an outside source/reservoir(s) to the cornea 2206 below the eye-contacting surface 104. In some embodiments, the same fluid inlet 7908 and fluid outlet 7910 may be used for each substance. In some embodiments, each substance may have a dedicated fluid inlet and fluid outlet. In some embodiments, oxygen may be generated using electrochemical cells for electrolysis and delivery to the eye (e.g., 95% oxygen at 15 ml/min).

The proximal end of the fluid-filled chamber 106 may comprise or be coupled to a light source 7906. For example, the light source 7906 may be an ultraviolet light-emitting diode (LED) (e.g., 365 nm wavelength) or an optical fiber coupled to an external ultraviolet LED or laser or the like. In some embodiments, the light source 7096 may be a green LED (e.g., 525 nm wavelength) or an optical fiber coupled to an external green LED or laser of the like. During or following oxygen and/or riboflavin (or other UV-sensitive or photosensitizing therapeutic substance) delivery, the ultraviolet light source 7906 may be used to cross-link the cornea 2206 (e.g., for treatment of keratoconus). Oxygen delivery and/or photosensitization may accelerate cross-linking.

In some embodiments, the light source 7906 may have an intensity of about 20 mW/cm$^2$. In some embodiments, the light source 7906 may have an intensity of about 3 mW/cm$^2$. In some embodiments, the light source 7906 may have an intensity of about 9 mW/cm$^2$. In some embodiments, the light source 7906 may have an intensity of about 10 mW/cm$^2$. In some embodiments, the light source 7906 may have an intensity of about 15 mW/cm$^2$.

In some embodiments, oxygen and/or other therapeutic substances may be delivered to the eye 200 using a shockwave generator 7900 without concurrent or subsequent cross-linking.

In some embodiments, the shockwave generator 7900 may further comprise a fluid inlet 108 and a fluid outlet 109 in fluid communication with the fluid-filled chamber 106 as described herein. The fluid may be circulated within the fluid-filled chamber 106 via the fluid inlet 108 and the fluid outlet 109. The fluid inlet 108 may be configured to deliver fluid to a distal portion of the shockwave generator 7900 (e.g., a distal portion of the wave guide 7902) and the fluid outlet 109 may be configured to remove fluid from a proximal portion of the shockwave generator 7900 (e.g., near the electrodes 110, 112) such that fluid flows through the housing 102 in a direction opposite that of the direction of shockwave travel.

The shockwave wave guide 7902 may comprise stainless steel tube having an outer diameter within a range of about 1 mm to about 8 mm, for example about 1 mm, about 2 mm, about 3 mm, about 5 mm, or about 8 mm. The shockwave wave guide 7902 may comprise stainless steel tube having an outer diameter of about 7 mm. The wave guide 7902 may have a wall thickness of about 0.5 mm.

In some embodiments, the wave guide 7902 may have a length within a range of about 1 cm to about 2 cm. In some embodiments, the wave guide 7902 may be about 12 mm or more in length. For example, the wave guide may have a length within a range of about 12 mm to about 80 mm, for example about 20 mm. The shockwave wave guide 7902 may comprise stainless steel tube having length of about 40 mm.

In some embodiments, one or more acoustic cross-linking shockwave generators 7900 may be coupled to a fluid-filled contact lens as described herein.

In some embodiments, one or more acoustic cross-linking shockwave generators 7900 with wave guide 7902 may be mounted on a trial frame, such as an adjustable goggle, as described herein.

Figure 80:
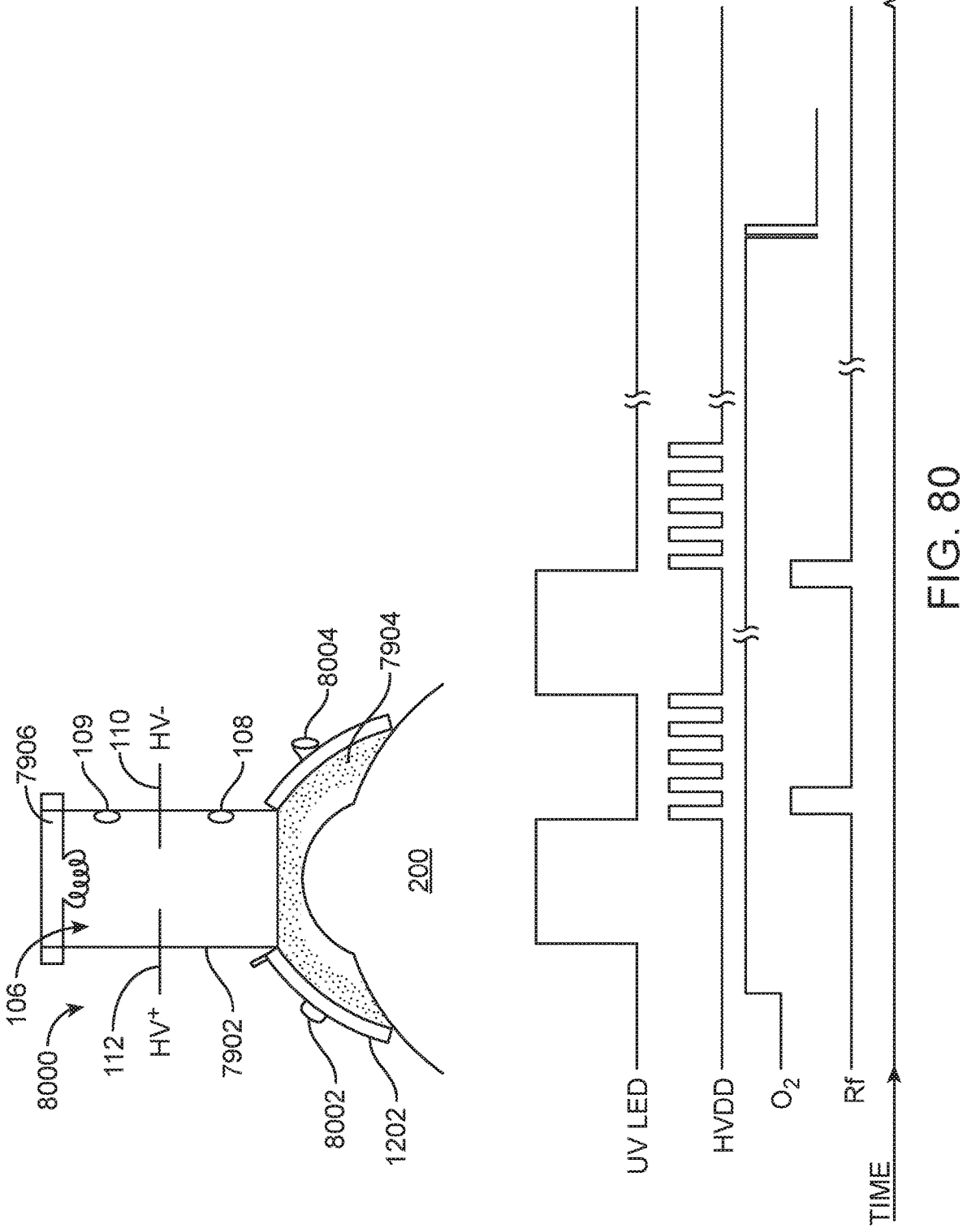
FIG. 80 shows a side view of an exemplary acoustic cross-linking shockwave wave guide, in accordance with embodiments.

FIG. 80 shows a side view of an exemplary acoustic cross-linking shockwave generator 8000 comprising a shockwave wave guide 7902. The acoustic cross-linking shockwave generator 8000 may be substantially similar to the shockwave generator shown in FIG. 79. The acoustic cross-linking shockwave generator 8000 may comprise a light source 7906 (e.g., a green or ultraviolet LED) as described herein. The light source 7906 may be cycled on and off. In some embodiments, the light source off cycle may correspond to an on cycle of the high voltage electrodes 110, 112 within the fluid-filled chamber 106 for concurrent shockwave-mediated drug (e.g., oxygen and riboflavin) delivery. The on/off cycle of the light source 7906 (and optionally the shockwave generating electrodes 110, 112) may be about every 5 seconds. Oxygen may be generated by an electrolyzer cell driven by a low power current source (e.g., a AA battery) from atmosphere and delivered to a fluid inlet 8002 of the suction ring 1202 at the patient interface. Riboflavin may be delivered to the same fluid inlet 8002 or a different fluid inlet 8004 as described herein. Oxygen (and riboflavin, etc.) may be pushed into the cornea 2206 with the shockwaves as described herein. The on/off light cycle may be repeated as needed to achieve the desired level of corneal cross-linking.

For example, the tissue may be soaked with 0.1% riboflavin for 30 minutes followed by ultraviolet irradiance at at least about 3 mW/cm² for 30 minutes per eye. In some embodiments, riboflavin delivery may be enhanced by acoustic radiation force shockwave therapy. Acoustic radiation force (i.e. the force from the shockwaves) may drive the therapeutic substance(s) into the tissue. 10 minutes of ultraviolet irradiance at 9 mW/cm² may then be applied with a simultaneous oxygen soak (e.g., with an electrochemical cell flow rate of about 16 ml/min). Shockwave therapy may be delivered with a system mounted on a pair of trial frame goggles.

In some examples, riboflavin delivery may be enhanced using cornea-targeted soundwaves in an epithelial-sparing 5-minute cycle followed by cell-generated (~90% pure) oxygen and ultraviolet irradiance at about 10 mW/cm² for about 10 minutes exposure. The total treatment time may be about 15 minutes per eye.

Figure 81:
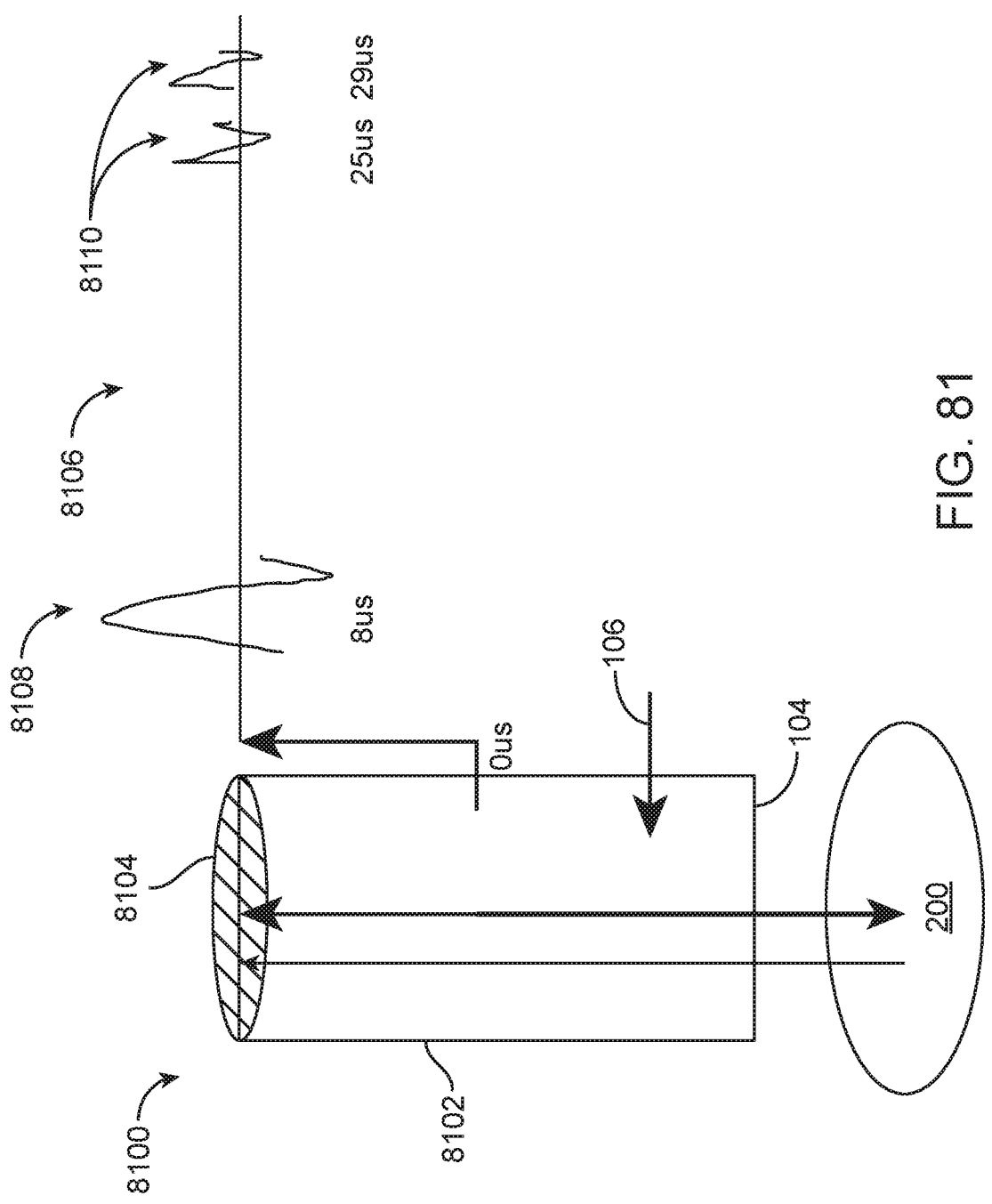
FIG. 81 shows a schematic of an exemplary system for passive cavitation detection, in accordance with embodiments.

FIG. 81 shows a schematic of an exemplary system 8100 for passive cavitation detection. Any of the shockwave generators described herein may comprise a passive cavitation detector 8104. During pulsing, the passive cavitation detector 8104 may be configured to detect shockwave generation (e.g., "main bang delay" 8108) by a shockwave generator 8102 and cavitation formation and collapse 8110 within the tissue 200. In some embodiments, the passive cavitation detector 8104 may comprise a piezo detector such as a hydrophone. In some embodiments, the passive cavitation detector 8104 may detect a signal 8106 indicating the formation and collapse 8110 of cavitational bubbles within the tissue 200. The signal 8106 may include timing and spectra information (e.g., rebound lag, intensity, etc.) about the bubbles which may be extracted intraoperatively. The rate of collapse of the bubbles may be related to intraocular pressure (TOP), thus passive cavitation detection may be utilized to indirectly measure IOP intraoperatively without invasiveness. IOP measurements may be particularly useful during glaucoma treatment and/or for improved safety and efficiency of selective shockwave therapy.

Steady state cavitation bubble dissolution time in aqueous of an anterior chamber of treated eye may be inversely related to IOP. The passive cavitation detector 8104 may be used to record tissue bubble signatures (e.g., reflected amplitude and time of flight) from the anterior chamber. Bubble sizes induced in tissue by the spark gap 114 in the fluid-filled shock chamber 106 can be set to two selected average cloud sizes (e.g., by pulse frequency and voltage adjustments) and the tissue steady state bubble dissolution rates may be extracted following averaging and filtering of the passive cavitation detector signatures 8106. This process may be entirely non-invasive and real time intraoperative.

The eye 200 (i.e., a pressure vessel) imposes forces on oscillating cavitation bubble sizes due to the native fluid pressure ("TOP"). A passive cavitation detector 8104 and high frequency shockwave generator 8102 may interact to extract a "stimulus-free" bubble cloud size maxima. Next a second known stimulus (e.g., ⅟₁₁th the primary high frequency resonance) may be applied by a small ultrasonic generator (e.g., 28 KHz) and the bubble cloud size maxima may be extracted by the PCD/PC software. The sequence may be repeated for improved accuracy of TOP extraction over hundreds of cycles (e.g., 0.1 secs-1 sec).

In some embodiments, TOP may be measured using other non-contact methods such as an air-puff tonometer instead of or in addition to a passive cavitation detector 8104.

In some embodiments, the passive cavitation detector 8104 may operate at a frequency of about 10 MHz and have a high acoustic impedance.

In some embodiments, it may be beneficial to characterize shockwave generation and repeatability prior to use to ensure uniform acoustic energy signatures (averages, standard deviations) are emitted for repeated treatments. Any of the systems described herein may have their acoustic emission footprint rapidly checked prior to intraocular use. For example, acoustic pressure color maps may be induced onto Prescale FujiFilm by shockwave exposure. The acoustic pressure color maps may be image processed and analyzed for comparison to a reference image utilizing typical treatment settings (e.g., voltage, frequency, etc.) for only a brief period (e.g., 10 msecs-1 sec) in saline. The precut Fuji Film (grade sensitive pressure range, enclosed in water resistant plastic sleeve pocket) may be a disposable. The highest acoustic pressure mapped onto film may be achieved by a color camera and white light illumination. Borescope-like fiber optics may be used to transport uniform illumination and color map to and from camera & Film. A +/−15% accuracy may be targeted at the start of the treatment.

Figure 82:
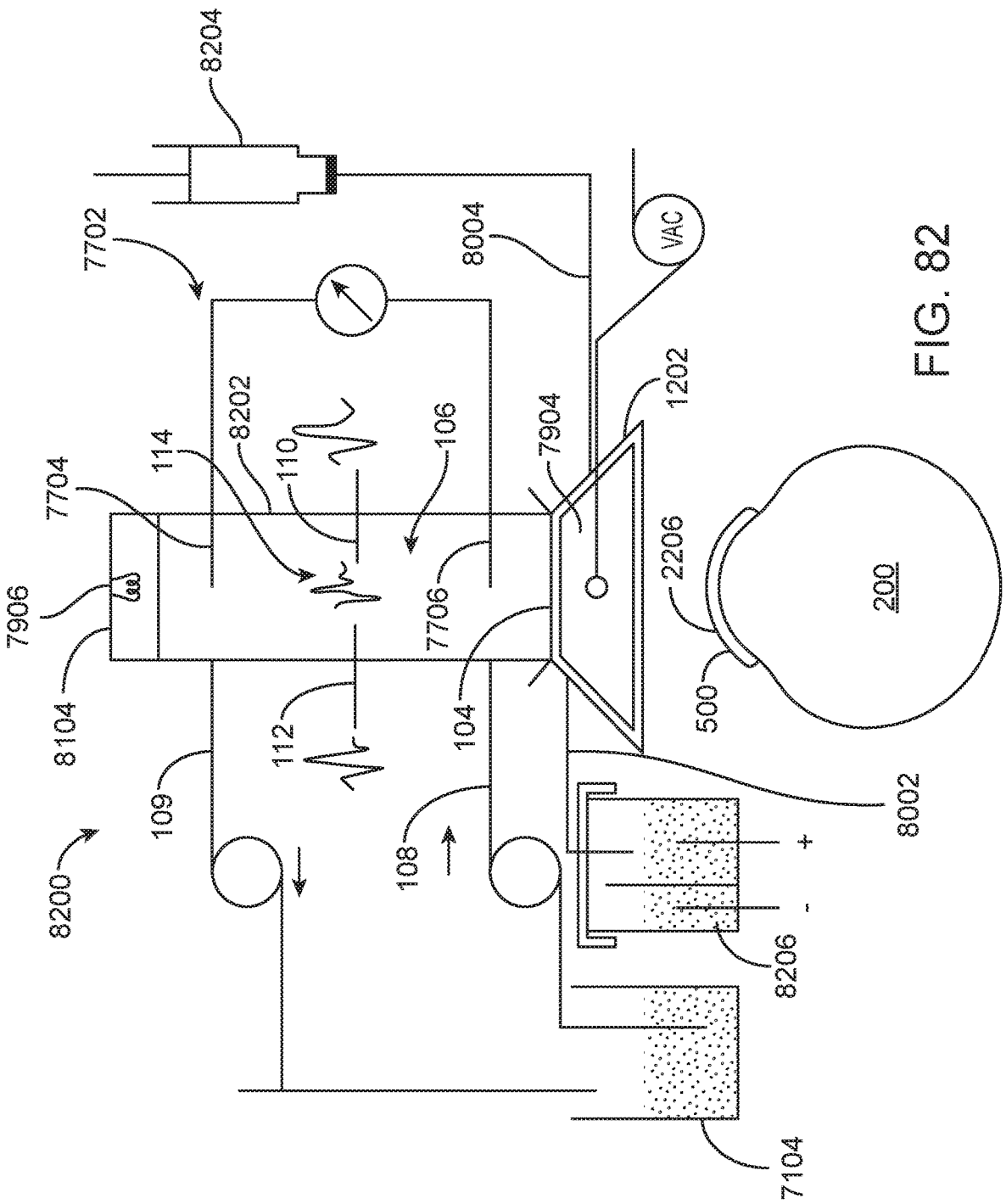
FIG. 82 shows an exemplary treatment system including passive cavitation detection, in accordance with embodiments.

FIG. 82 shows an exemplary treatment system 8200 including passive cavitation detection. The system 8200 may be substantially similar to any of the systems described herein. The system 8200 may be configured for treatment of presbyopia, glaucoma, dry eye disease, AMD, keratoconus, or the like as described herein. The system 8200 may comprise a shockwave generator 8202 which may be substantially similar to any of the shockwave generators described herein. For example, the shockwave generator 8202 may comprise a first electrode 110 and a second electrode 112 disposed within a housing 102. The housing 102 may comprise a fluid-filled chamber 106 and an eye-contacting surface 104. The housing 102 may be substantially tubular, with the electrodes 110, 112 disposed near a proximal end of the fluid-filled chamber 106 and the eye-contacting surface 104 disposed at a distal end of the fluid-filled chamber 106 with an elongated central portion 8202 providing a wave guide therebetween. The eye-contacting surface 104 may, for example, comprise a PET membrane as described herein. The eye-contacting surface 104 may be configured to be coupled to a surface 500 of an eye 200 of a patient. A coupling fluid or gel, for example a water column, may be on or under the eye-contacting surface in order to facilitate contact between the eye-contacting surface 104 and the surface 200 of the eye and/or in order to facilitate transmission of the shockwave from the shockwave generator 8200 to the eye 200 as described herein.

In some embodiments, the shockwave generator 8200 may further comprise a fluid inlet 108 and a fluid outlet 109 in fluid communication with the fluid-filled chamber 106 as described herein. The fluid may be circulated within the fluid-filled chamber 106 via the fluid inlet 108 and the fluid outlet 109. The fluid may be circulated a rate sufficient to remove bubbles and/or or heat formed during shockwave generation (e.g., about 100 ml/min). The fluid inlet 108 may be configured to deliver fluid to a distal portion of the shockwave generator 8200 (e.g., a distal portion of the wave guide 8202) and the fluid outlet 109 may be configured to remove fluid from a proximal portion of the shockwave generator 8200 (e.g., near the electrodes 110, 112) such that fluid flows through the housing 102 in a direction opposite that of the direction of shockwave travel.

The fluid-filled chamber 106 may comprise a conductivity sensor 7702. The conductivity sensor 7702 may comprise a pair of low voltage platinum electrodes 7704, 7706 disposed at a fixed distance apart (e.g., book-ending the high voltage shockwave generating electrodes 110, 112). The pair of platinum electrodes 7704, 7706 may be configured to periodically or continuously sample the conductivity of the fluid in the fluid-filled chamber 106 as described herein.

In some embodiments, a reservoir 7904 of oxygen and/or one or more therapeutic substances may disposed be on or under the eye-contacting surface 104 for drug delivery to the cornea 2206. The reservoir 7904 may be coupled to the eye with a vacuum-sealed fixation ring 1202. Shockwaves generated by the shockwave generator may enhance drug delivery to the cornea 2206 (e.g., to the epithelium) by causing surface fragmentation and/or micro-poration of the corneal tissue of interest to improve drug permeability. In some embodiments, the therapeutic substance may comprise a photosensitizing agent such as riboflavin, a riboflavin nanoparticle, or rose bengal.

In some embodiments, the reservoir 7904 may comprise a fluid inlet and optionally a fluid outlet for circulation of oxygen and/or therapeutic substances from an outside source/reservoir(s) to the cornea below the eye-contacting surface. In some embodiments, the same fluid inlet and fluid outlet may be used for each substance. In some embodiments, each substance may have a dedicated fluid inlet and fluid outlet. In some embodiments, oxygen may be generated using electrochemical cell(s) 8206 for electrolysis and delivery to the eye (e.g., >90% oxygen at 15 ml/min). For example, oxygen may be generated by an electrolyzer cell driven by a low power current source (e.g., a AA battery) from atmosphere and delivered to a fluid inlet 8002 of the suction ring 1202 at the patient interface. Riboflavin may be delivered to the same fluid inlet 8002 or a different fluid inlet 8004 from a reservoir 8204 as described herein. In some embodiments, the reservoir 8204 may be a sterile IV bag or a syringe or the like.

In some embodiments, oxygen and/or other therapeutic substances may be delivered to the eye using a shockwave generator 8200 without concurrent or subsequent cross-linking.

In some embodiments, the proximal end of the fluid-filled chamber 106 may comprise a passive cavitation detector 8104. The passive cavitation detector may be configured to intraoperatively monitor cavitation and/or IOP as described herein. The passive cavitation detector may be used to confirm cavitation intensity and onset is within bounds, ensuring bubble presence and extraction. The passive cavitation detector may also be used to detect tissue cavitation duration and intensity for estimating IOP.

In some embodiments, the proximal end of the fluid-filled chamber 106 may comprise or be coupled to a light source 7906. For example, the light source may be an ultraviolet light-emitting diode (LED) (e.g., 365 nm wavelength) or an optical fiber coupled to an external ultraviolet LED or laser or the like. In some embodiments, the light source may be a green LED (e.g., 525 nm wavelength) or an optical fiber coupled to an external green LED or laser of the like. During or following oxygen and/or riboflavin (or other UV-sensitive or photosensitizing therapeutic substance) delivery, the ultraviolet light source may be used to cross-link the cornea (e.g., for treatment of keratoconus).

The shockwave wave guide 8202 may comprise stainless steel tube having an outer diameter within a range of about 1 mm to about 8 mm, for example about 1 mm, about 2 mm, about 3 mm, about 5 mm, or about 8 mm. The shockwave wave guide may comprise stainless steel tube having an outer diameter of about 7 mm. The wave guide may have a wall thickness of about 0.5 mm.

In some embodiments, the wave guide may have a length within a range of about 1 cm to about 2 cm. In some embodiments, the wave guide may be about 12 mm or more in length. For example, the wave guide may have a length within a range of about 12 mm to about 80 mm, for example about 20 mm. The shockwave wave guide may comprise stainless steel tube having length of about 40 mm.

In some embodiments, one or more acoustic cross-linking shockwave generators may be coupled to a fluid-filled contact lens as described herein.

In some embodiments, one or more acoustic cross-linking shockwave generators with wave guide may be mounted on a trial frame, such as an adjustable goggle, as described herein.

Figure 83:
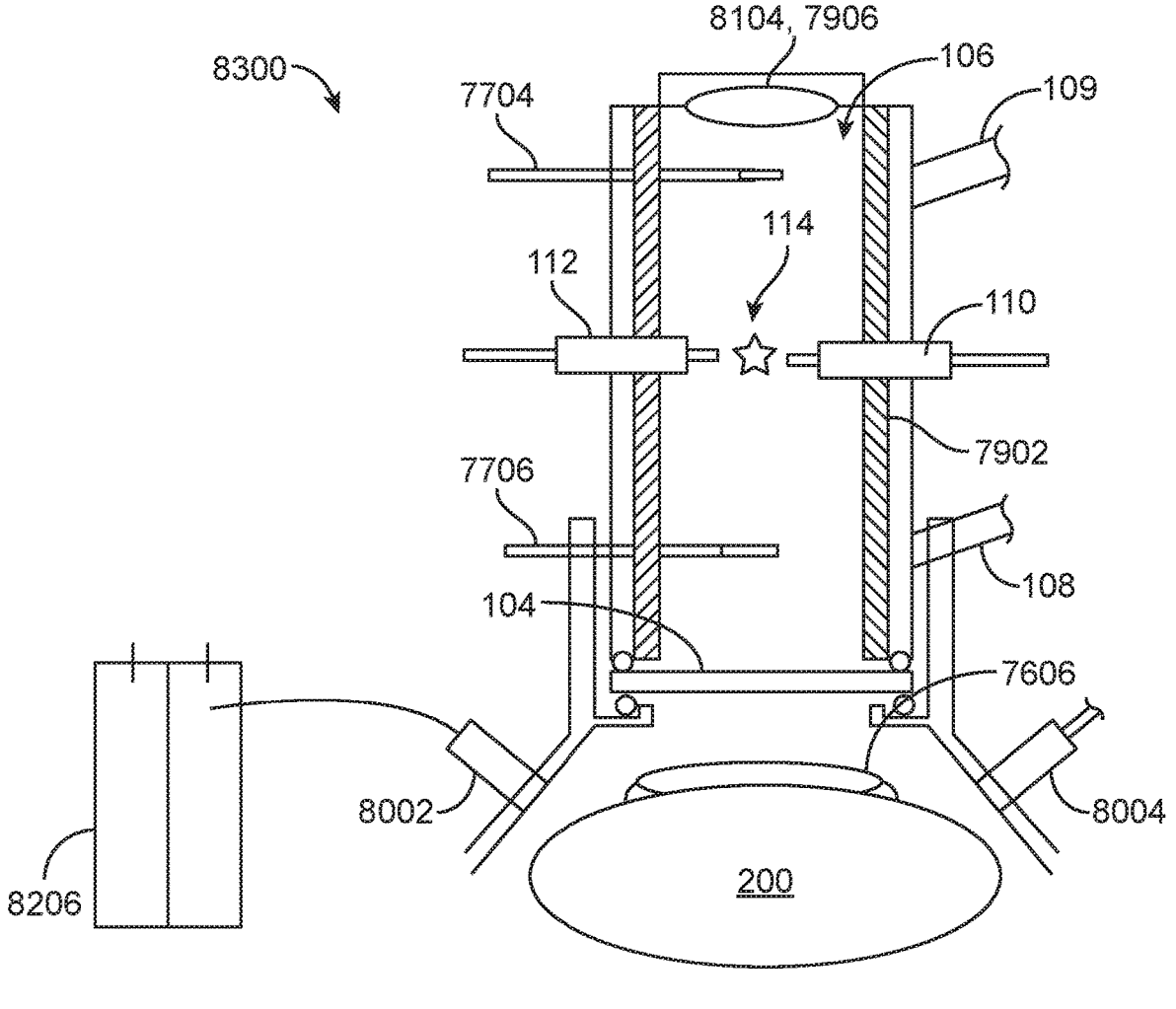
FIG. 83 shows a side view of an exemplary treatment system including a conductivity sensor, acoustic cross-linking, and/or passive cavitation detection, in accordance with embodiments.

FIG. 83 shows a side view of an exemplary treatment system 8300 comprising a conductivity sensor, acoustic cross-linking, and/or passive cavitation detection. The system 8300 may be substantially similar to the system shown in FIG. 82. The system 8300 may be configured to treat one or more conditions, and/or target one or more locations on or below the surface of the eye as described herein.

In some embodiments, the eye-contacting surface (e.g., PET film) 104 may be robustly sealed to the reservoir 7904 to fluidly isolate the shockwave fluid-filled chamber 106 from the oxygen/riboflavin reservoir 7904.

Figure 85A:
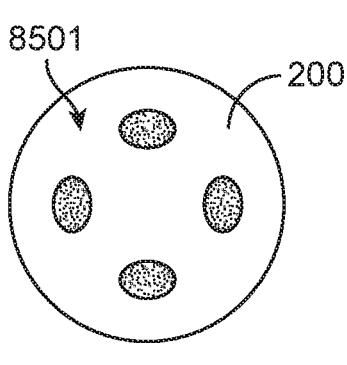
FIGS. 85A-85F show exemplary treatment patterns for various indications, in accordance with embodiments.
Figure 85B:
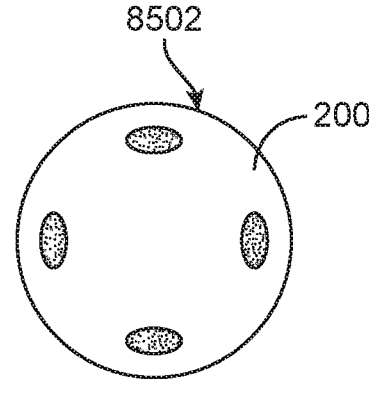

In some embodiments, the system 8300, or any of the systems described herein, may be used to fractionate the PVZ as described herein. For example, a clear aperture of a 3 mm focal length shockwave generator may be placed over the surface of the eye 200 above the PVZ using frame controls. Saline may be circulated within the fluid-filled chamber 106 and conductivity measurements and passive cavitation detection may be utilized during treatment. Treatment may be patterned in an annulus to about four locations along the meridians of the eye in each of four quadrants of the eye (e.g., as shown in FIG. 85B). The system 8300 may be positioned at a first location corresponding to a first quadrant and the PVZ may be treated for about 1 minute with shockwaves generated with a voltage of about 2 kV and a frequency of about 3 kHz. The system 8300 may be then be re-positioned to the second location corresponding the second quadrant for treatment, and so on. In some embodiments, eight locations or more may be treated along the annulus as described herein.

In some embodiments, the system 8300, or any of the systems described herein, may be used to disaggregate a crystalline lens as described herein. For example, a clear aperture of a planar 8 mm shockwave generator may be placed one the cornea of the eye 200. Saline may be circulated within the fluid-filled chamber 106 and conductivity measurements and passive cavitation detection may be utilized during treatment. The lens may be treated for about 1 minute with shockwaves generated with a voltage of about 0.5 kV and a frequency of about 4 kHz.

In some embodiments, the system 8300, or any of the systems described herein, may be used to dilate and/or clear the trabecular meshwork and/or Schlemm's Canal as described herein. For example, a clear aperture of a planar 3 mm shockwave generator may be placed over the surface of the eye 200 above the limbus using frame controls. Saline may be circulated within the fluid-filled chamber 106 and conductivity measurements and passive cavitation detection may be utilized during treatment. Treatment may be patterned in an annulus to four locations along the meridians of the eye in each of four quadrants of the eye (e.g., as shown in FIG. 85A). The system 8300 may be positioned at a first location corresponding to a first quadrant and the trabecular meshwork and/or Schlemm's Canal may be treated for about 30 seconds with shockwaves generated with a voltage of about 1 kV and a frequency of about 4 kHz. The system 8300 may be then be re-positioned to the second location corresponding the second quadrant for treatment, and so on. Treatment may be repeated if sufficient cavitation and/or sufficient IOP change is not detected using the passive cavitation detector 8104. In some embodiments, eight locations or more may be treated along the annulus as described herein.

In some embodiments, the system 8300, or any of the systems described herein, may be used to dilate and/or clear the meibomian glands as described herein. For example, an air-filed scleral contact lens 7606 may be placed on the eye 200 and the eyelids may be closed. Upper and lower shockwave generators may be placed on the eyelids over the meibomian glands. Saline may be circulated within the fluid-filled chamber 106 and conductivity measurements and passive cavitation detection may be utilized during treatment. The meibomian glands may be treated for about 1 minute with shockwaves generated with a voltage of about 2 kV and a frequency of about 4 kHz.

In some embodiments, the system 8300, or any of the systems described herein, may be used to cross-link the cornea as described herein. For example, riboflavin may be instilled into the cornea using shockwaves generated with a voltage of about 2 KV and a frequency of about 4 KHz delivered for 30 second intervals until sufficient riboflavin has permeated the cornea. Oxygen may then be instilled for 30 seconds before an ultraviolet laser 7906 (e.g., 365 nm laser at an intensity of about 10 mW/cm$^2$) is activated. Concurrent oxygen delivery and laser cross-linking may occur for about 10 minutes. Saline may be circulated within the fluid-filled chamber 106 and conductivity measurements and passive cavitation detection may be utilized during treatment.

FIG. 84 shows a schematic of an exemplary treatment system 8400 including acoustic cross-linking or passive cavitation detection. The system 8400 may be substantially similar to any of the systems described herein. The system 8400 may comprise a shockwave generator which may be substantially similar to any of the shockwave generators described herein. For example, the shockwave generator may comprise a first electrode 110 and a second electrode 112 disposed within a housing 102. The housing 102 may comprise a fluid-filled chamber 106 and an eye-contacting surface 104. The housing 102 may be substantially tubular, with the electrodes 110, 112 disposed near a proximal end of the fluid-filled chamber 106 and the eye-contacting surface 104 disposed at a distal end of the fluid-filled chamber 106 with an elongated central portion 8402 providing a wave guide therebetween. The eye-contacting surface 104 may, for example, comprise a PET membrane as described herein. The eye-contacting surface 104 may be configured to be coupled to a surface of an eye of a patient. A coupling fluid or gel, for example a water column, may be on or under the eye-contacting surface 104 in order to facilitate contact between the eye-contacting surface and the surface of the eye and/or in order to facilitate transmission of the shockwave from the shockwave generator to the eye as described herein.

In some embodiments, the shockwave generator may further comprise a fluid inlet 108 and a fluid outlet 109 in fluid communication with the fluid-filled chamber 106 as described herein. The fluid may be circulated within the fluid-filled chamber 106 via the fluid inlet 108 and the fluid outlet 109. The fluid may be circulated a rate sufficient to remove bubbles and/or or heat formed during shockwave generation (e.g., about 100 ml/min). The fluid inlet 108 may be configured to deliver fluid to a distal portion of the shockwave generator (e.g., a distal portion of the wave guide 8402) and the fluid outlet 109 may be configured to remove fluid from a proximal portion of the shockwave generator (e.g., near the electrodes 110, 112) such that fluid flows through the housing 102 in a direction opposite that of the direction of shockwave travel.

In some embodiments, the proximal end of the fluid-filled chamber 106 may be configured to act as a reflector in order to focus the shockwaves towards a desired pre-determined location via the wave guide. Alternatively, or in combination, one or more reflectors 802 may be coupled to an internal surface of the fluid-filled chamber 106 in order to focus the shockwaves. An inner wall of the fluid filled chamber 106 may be ellipsoidal in shape. Alternatively, or in combination, a distal portion of the wave guide 8402 may be configured to focus the shockwaves to a predetermined location on or below the surface of the eye.

Alternatively, or in combination, the proximal end of the fluid-filled chamber 106 may comprise a conductivity cell 7702 comprising a conductivity sensor configured to periodically or continuously sample the conductivity of the fluid in the fluid-filled chamber as described herein.

Alternatively, or in combination, the proximal end of the fluid-filled chamber 106 may comprise a passive cavitation detector 8104 as described herein.

Alternatively, or in combination, the proximal end of the fluid-filled chamber 106 may comprise a light source 7906 for acoustic cross-linking as described herein.

In some embodiments, a reservoir 7904 of oxygen and/or one or more therapeutic substances may disposed be on or under the eye-contacting surface 104 for drug delivery to the cornea as described herein. The reservoir 7904 may be coupled to the eye with a vacuum-sealed fixation ring 1202. Shockwaves generated by the shockwave generator may enhance drug delivery to the cornea (e.g., to the epithelium) by causing surface fragmentation and/or micro-poration of the corneal tissue of interest to improve drug permeability as described herein. In some embodiments, the therapeutic substance may comprise a photosensitizing agent such as riboflavin, a riboflavin nanoparticle, or rose bengal.

In some embodiments, the reservoir 7904 may comprise a fluid inlet 8406 and optionally a fluid outlet 8408 for circulation of oxygen and/or therapeutic substances from an outside source/reservoir(s) 8404 to the cornea below the eye-contacting surface. In some embodiments, the same fluid inlet 8406 and fluid outlet 8408 may be used for each substance. In some embodiments, each substance may have a dedicated fluid inlet and fluid outlet. In some embodiments, oxygen may be generated using electrochemical cell(s) 8206 for electrolysis and delivery to the eye (e.g., >90% oxygen at 15 ml/min). For example, oxygen may be generated by an electrolyzer cell driven by a low power current source (e.g., a AA battery) from atmosphere and delivered to a fluid inlet 8002 of the suction ring 1202 at the patient interface. Riboflavin may be delivered to the same fluid inlet 8002 or a different fluid inlet 8004 from a reservoir 8204 as described herein.

In some embodiments, oxygen and/or other therapeutic substances may be delivered to the eye using a shockwave generator without concurrent or subsequent cross-linking.

The shockwave wave guide 8402 may comprise stainless steel tube having an outer diameter within a range of about 1 mm to about 8 mm, for example about 1 mm, about 2 mm, about 3 mm, 5 mm, or about 8 mm. The shockwave wave guide may comprise stainless steel tube having an outer diameter of about 3 mm or 7 mm. The wave guide may have a wall thickness of about 0.5 mm.

In some embodiments, the wave guide 8402 may have a length within a range of about 1 cm to about 2 cm. In some embodiments, the wave guide may be about 12 mm or more in length. For example, the wave guide may have a length within a range of about 12 mm to about 80 mm, for example about 20 mm. The shockwave wave guide may comprise stainless steel tube having length of about 15 mm or about 30 mm.

FIGS. 85A-85F show exemplary treatment patterns for various targeted indications. Any of the shockwave generators or systems described herein may be used to treat the indications as shown. For example, one or more shockwave generators comprising a waveguide may be mounted on a pair of trial frame goggles as described herein in the pattern of interest for the targeted indication.

FIG. 85A shows a treatment pattern 8501 for glaucoma. Planar waves may be directed towards the limbus and/or sclera for micro-sonoporation thereof. Alternatively, or in combination, shockwaves can be used for non-thermal ciliary process fractionation in order to reduce aqueous production for glaucoma treatment. In some embodiments, microporation tracks may be generated to augment blood, oxygen, nutrient, and/or lymphatic flow and/or increase hydraulic conductivity in the tissue.

FIG. 85B shows a treatment pattern 8502 for presbyopia. Planar and/or focused waves may be directed towards the paralimbal sclera and/or posterior vitreous zonules for micro-sonoporation and/or fragmentation thereof.

Figure 85C:
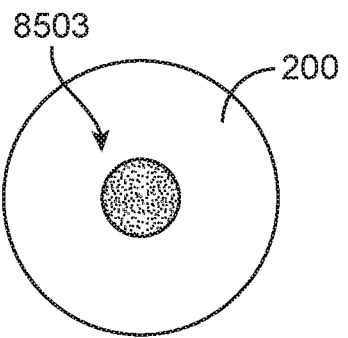

FIG. 85C shows a treatment pattern 8503 for corneal drug (e.g., riboflavin) delivery (without epi-fluorescent cross-linking). Low-power planar waves may be directed towards the cornea (e.g., epithelium) for surface fragmentation and micro-poration thereof in order to enhance drug delivery thereto.

Figure 85D:
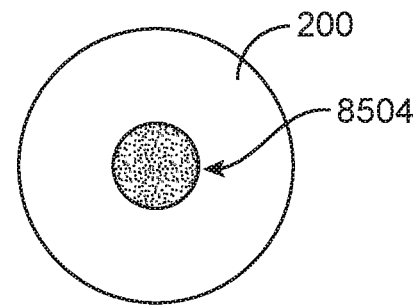

FIG. 85D shows a treatment pattern 8504 for acoustic crosslinking-accelerated cross-linking. Planar waves may be directed towards the cornea to enhance riboflavin and/or oxygen delivery as described herein. Ultraviolet light may then be used to irradiate and cross-link the cornea as described herein.

Figure 85E:
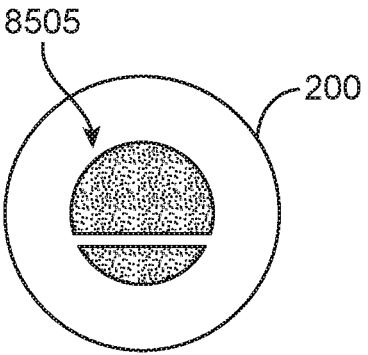

FIG. 85E shows a treatment pattern 8505 for dry eye disease. Planar waves may be directed towards the meibomian ducts/glands of the eyelid, optionally with the assistance of a contact lens for corneal protection, for vasodilation and/or decludication thereof.

Figure 85F:
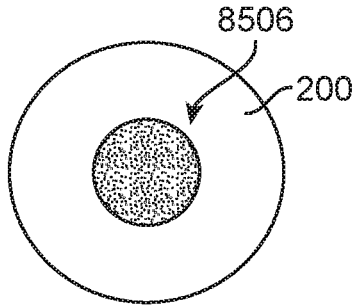

FIG. 85F shows a treatment pattern 8506 for AMD. Planar waves may be directed towards the retina for retinal/lymphatic plexus dilation and/or sono-stimulation thereof.

For dry AMD, non-selective low power treatment may be sufficient to induce sono-stimulation of the retina sufficient to induce vascular dilation and/or retinal senescent cell stimulation. For wet AMD, which exhibits neovascularization, it may be beneficial to preferentially enhance shockwave therapy at the sites of neovascularization in the retina in order to reduce or eliminate (e.g., fragment) the nascent leaky vasculature while sparing the surrounding tissue. In at least some instances, shockwave therapy may be locally enhanced by selective seeding of nanoparticles and/or microbubbles to the tissue. As described herein, low dose shockwave energy, which may have limited effects on unseeded tissue, may selectively fragment the microbubble-seeded tissue (e.g., the collapsing microbubbles may directly damage cells as described herein). In some embodiments, microbubbles or microbubble-formation augmenting particles may be injected into the blood stream and, due to the leaky nature of the retinal neovasculature, accumulate in the retinal tissue adjacent the neovasculature. Alternatively, or in combination, laser energy may be focused onto the retina at a desired treatment location(s) to order to induce microbubble formation at that location(s). Multiple ranges of wavelengths can be used to induce microbubble formation in tissue including 532 nm, 590 nm, femto-lasers, near-infrared, mid-infrared, or 6 μm-10 μm. The laser may be a pulsed picosecond, nanosecond, or microsecond laser. Once the microbubbles have been seeded, low energy shockwave therapy may be directed to the retina as described herein and therapy may be selectively enhanced at the seeded tissue via the microbubbles.

Any of the systems described herein may be used to perform a capsulorhexis or capsulotomy on the crystalline lens capsule of the eye. For example, sparged microbubbles emanating from a soft contact lens placed on an intraocular lens inserted during phaco/cataract treatment may emulsify the insonicated 5.5 mm central lens and soften the cataract. The treatment may allow capsulorhexis or capsulotomy depending on exposure and circulating microbubble interactions/patterning. Microbubbles and/or microparticles can selectively act as acoustic shields or cavitation seeding particles. Channeling these through a thin capsular IOL inserted during cataract surgery during en face ab externo shockwave insonication may deposit energies on the capsule and/or lens according to spatial patterns of the channels and timed flow of either (microparticle or microbubble) therein.

As will be understood by one of ordinary skill in the art, any of the shockwave generating devices and systems described herein may comprise may be combined with one another or substituted for another and thus any number of combinations may be used. For example, any of the devices and systems described has having a pair of electrodes for shockwave generation may instead utilize a piezo-electric, laser, or magneto-electric shockwave generation mechanism as described herein. Additionally, various features of the shockwave generating devices and systems have been described herein including corneal sparing contact lenses, contact lens balloons, shockwave wave guides, focused shockwave generators, reflectors, variable focus lenses, unfocused shockwave generators, conductivity sensors, current sensors, pressure sensors, passive cavitation detectors, imaging systems, drug delivery reservoirs, cross-linking laser energy sources, fluid recirculation systems for bubble removal, and the like. One of ordinary skill in the art will appreciate that these features may be combined with one another or substituted for one another and thus any number of combinations may be used.

Various methods, treatment patterns, and target locations have been described herein including a) treatment methods and patterns for presbyopia, glaucoma, dry eye disease, dry AMD, wet AMD, keratoconus, corneal ectasia, and the like, and b) target locations on or in the eye including one or more of the trabecular meshwork, Schlemm's canal, ciliary body (e.g., ciliary processes, muscle, selected parts anterior/posterior/equatorial of ciliary body, etc.), pars plana, pars plicata, cornea, sclera, lens, retina, fovea, perifovea, intermediate vitreous zonule (IVZ), posterior vitreous zonule (PVZ), vitreous, eyelids, and/or meibomian gland. One or ordinary skill in the art will appreciate that these treatment methods, patterns, and target locations may be selected based on the indication, or combination of indications, to be treated. Devices and systems may be configured to treat one or more target locations for one or more indications simultaneous or sequentially as desired. In some embodiments, a system may comprise a plurality of shockwave generators positioned at different locations adjacent the surface of the eye and focused (or not) onto different target locations on or under the eye to treat a plurality of indications without moving the system away from the patient's eye. One of ordinary skill in the art will appreciate that these treatment locations, methods, patterns may be combined with one another or substituted for one another and thus any number of combinations may be used.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for treating an eye, the apparatus comprising:

a housing comprising a fluid-filled chamber and an eye-contacting surface configured to contact a surface of an eye;

a first electrode disposed within the housing; and a second electrode disposed within the housing and coaxially aligned with the first electrode, wherein a distal tip of the first electrode and a distal tip of the second electrode are separated by a gap, wherein the first electrode and the second electrode are configured to generate an electric arc across the gap when energized and produce a shockwave in a fluid of the fluid-filled chamber, further comprising a fluid inlet and a fluid outlet in fluid communication with the fluid-filled chamber, wherein the apparatus further comprises a conductivity sensor at least partially disposed within the fluid-filled chamber and configured to measure a conductivity periodically or continuously of the fluid within the fluid-filled chamber wherein the conductivity sensor is configured to monitor changes in conductivity caused by release of metallic ions from the first and second electrodes during erosion of the electrodes.

2. The apparatus of claim 1, wherein an inner surface of the housing is configured to focus the shockwave to a predetermined location on or below the surface of the eye.

3. The apparatus of claim 1, further comprising a reflector disposed within the housing and configured to focus the shockwave to a predetermined location on or below the surface of the eye.

4. The apparatus of claim 1, further comprising one or more wires coupled to the first electrode or the second electrode and configured to provide energy thereto.

5. The apparatus of claim 1, wherein the first electrode and the second electrode comprise a first tip of a first wire and a second tip of a second wire.

6. The apparatus of claim 1, wherein the fluid comprises saline or water.

7. The apparatus of claim 1, wherein the first and second electrodes are coated with graphene to reduce erosion during shockwave production.

8. The apparatus of claim 1, wherein the housing is ellipsoidal.

9. The apparatus of claim 1, wherein the housing further comprises a fluid-filled wave guide disposed between the fluid-filled chamber and the eye-contacting surface and configured to fluidly couple the fluid-filled chamber and the eye-contacting surface.

10. The apparatus of claim 1, further comprising an acoustic lens disposed within the housing and configured to focus the shockwave to one or more predetermined locations on or below the surface of the eye.

11. The apparatus of claim 1, wherein the conductivity sensor comprises a pair of platinum electrodes.

12. The apparatus of claim 1, further comprising a light source at least partially disposed within the fluid-filled chamber and configured to emit light towards the surface of the eye.

13. A system for treating an eye, the system comprising:

the apparatus of claim 1; and an energy source operably coupled to the first electrode and the second electrode by one or more wires.

* * * * *